(12) United States Patent
Papeo et al.

(10) Patent No.: US 8,592,416 B2
(45) Date of Patent: Nov. 26, 2013

(54) ISOQUINOLIN-1 (2H)-ONE DERIVATIVES AS PARP-1 INHIBITORS

(75) Inventors: Gianluca Mariano Enrico Papeo, Cernusco Lombardone (IT); Jay Aaron Bertrand, Villa Cortese (IT); Giovanni Cervi, Como (IT); Barbara Forte, Milan (IT); Rosita Lupi, Legnano (IT); Alessia Montagnoli, Milan (IT); Alessandra Scolaro, Bresso (IT); Fabio Zuccotto, Milan (IT); Paolo Orsini, Legnano (IT); Helena Posteri, Travedona Monate (IT)

(73) Assignee: Nerviano Medical Sciences S.r.l., Nerviano (MI) (IT)

( * ) Notice: Subject to any disclaimer, the term of this patent is extended or adjusted under 35 U.S.C. 154(b) by 0 days.

(21) Appl. No.: 13/320,969

(22) PCT Filed: May 19, 2010

(86) PCT No.: PCT/EP2010/056921
§ 371 (c)(1),
(2), (4) Date: Mar. 5, 2012

(87) PCT Pub. No.: WO2010/133647
PCT Pub. Date: Nov. 25, 2010

(65) Prior Publication Data
US 2012/0157454 A1  Jun. 21, 2012

(30) Foreign Application Priority Data
May 21, 2009 (EP) .................... 09160869

(51) Int. Cl.
C07D 217/24 (2006.01)
C07D 401/04 (2006.01)
A61K 31/472 (2006.01)

(52) U.S. Cl.
USPC .......... 514/235.2; 514/309; 544/128; 546/77; 546/142

(58) Field of Classification Search
None
See application file for complete search history.

(56) References Cited

FOREIGN PATENT DOCUMENTS

| EP | 0 389 995 A2 | 10/1990 |
|---|---|---|
| EP | 0 591 937 A1 | 4/1994 |
| EP | 1 566 380 A1 | 8/2005 |
| WO | WO 02/090334 A1 | 11/2002 |
| WO | WO 2008/092292 A1 | 8/2008 |

OTHER PUBLICATIONS

International Search Report dated Oct. 1, 2010 issued in PCT/EP2010/056921.

*Primary Examiner* — Zinna Northington Davis
(74) *Attorney, Agent, or Firm* — Scully, Scott, Murphy & Presser, P.C.

(57) ABSTRACT

There are provided substituted isoquinolin-1(2H)-one derivatives which selectively inhibit the activity of poly (ADP-ribose) polymerase PARP-1 with respect to poly (ADP-ribose) polymerase PARP-2. The compounds of the present invention are therefore useful in treating diseases such as cancer, cardiovascular diseases, central nervous system injury and different forms of inflammation. The present invention also provides methods for preparing these compounds, pharmaceutical compositions comprising these compounds, and methods of treating diseases utilizing pharmaceutical compositions comprising these compounds. A screening method for the identification of compounds capable of binding several PARP proteins, as well the probes used in such method, are further objects of the invention.

9 Claims, No Drawings

ISOQUINOLIN-1 (2H)-ONE DERIVATIVES AS PARP-1 INHIBITORS

This application is a 371 of PCT/EP10/56921 filed May 19, 2010.

The present invention concerns substituted isoquinolin-1 (2H)-one derivatives which selectively inhibit the activity of poly (ADP-ribose) polymerase PARP-1 with respect to poly (ADP-ribose) polymerase PARP-2. The compounds of this invention are therefore useful in treating diseases such as cancer, cardiovascular diseases, central nervous system injury and different forms of inflammation. The present invention also provides methods for preparing these compounds, pharmaceutical compositions comprising these compounds, and methods of treating diseases utilizing pharmaceutical compositions comprising these compounds.

Poly (ADP-ribose) polymerases belong to a family of 17 members that catalyze the addition of ADP-ribose units to DNA or different acceptor proteins, which affect cellular processes as diverse as replication, transcription, differentiation, gene regulation, protein degradation and spindle maintenance. PARP-1 and PARP-2 are the only enzymes among the PARPs that are activated by DNA damage and are involved in DNA repair.

PARP-1 is a nuclear protein consisting of three domains: the N-terminal DNA-binding domain containing two zinc fingers, the auto modification domain, and the C-terminal catalytic domain. PARP-1 binds through the zinc-finger domain to single strand DNA breaks (SSB), cleaves NAD+, and attaches multiple ADP-ribose units to target proteins such as histones and various DNA repair enzymes. This results in a highly negatively charged target, which in turn leads to the unwinding and repair of the damaged DNA through the base excision repair pathway. In knock out mouse models, deletion of PARP-1 impairs DNA repair but it is not embryonic lethal. Double knock out PARP-1 and PARP-2 mice instead die during early embryogenesis, suggesting that the two enzymes display not completely overlapping functions. Enhanced PARP-1 expression and/or activity have been shown in different tumor cell lines, including malignant lymphomas, hepatocellular carcinoma, cervical carcinoma, colorectal carcinoma, leukemia. This may allow tumor cells to withstand genotoxic stress and increase their resistance to DNA-damaging agents. As a consequence, inhibition of PARP-1 through small molecules has been shown to sensitize tumor cells to cytotoxic therapy (e.g. temozolomide, platinums, topoisomerase inhibitors and radiation). A significant window seems to exist between the ability of a PARP inhibitor to potentiate therapeutic benefits and undesirable side effects. Whereas the therapeutic use of PARP inhibitors in combination with DNA damaging agents is not novel, the use of these agents as monotherapy, in particular tumor genetic backgrounds deficient in the homologous recombination DNA repair, represents a new approach. Individuals with heterozygous germ line mutations in either the BRCA-1 or BRCA-2 homologous recombination repair genes exhibit high life time risks of developing breast and other cancers. Tumors arising in mutation carriers have generally lost the wild type allele and do not express functional BRCA-1 and BRCA-2 proteins.

Therefore, loss of these two proteins leads to a tumor-specific dysfunction in the repair of double strand breaks by homologous recombination. It is known that when PARP-1 is inhibited, base excision repair is reduced and single strand breaks that are generated during the normal cell cycle persist. It has also been established that replication forks that encounter an unrepaired break can form double strand breaks, which are normally repaired by homologous recombination. Tumor cells that are deficient in homologous recombination repair such as BRCA-1 and BRCA-2 mutants are therefore highly sensitive to PARP inhibition compared with wild-type cells. This is in line with the concept of synthetic lethality, in which the two pathway defects alone are innocuous but combined become lethal: PARP inhibitors may be more effective in patients with tumors with specific DNA repair defects without affecting normal heterozygous tissues. Putative patient population includes, besides BRCA mutants that represent the majority of hereditary breast and ovarian cancer, also a substantial fraction of sporadic cancers with defects in homologous recombination repair, a phenomenon termed "BRCAness". For example, methylation of the promoters of the BRCA-1 or FANCF genes and amplification of the EMSY gene, which encodes a BRCA-2 interacting protein. By extending the rational of synthetic lethality of PARP and BRCA-1 and BRCA-2, it is likely that deficiencies in any gene that is not redundant in double strand break repair should be sensitive to PARP inhibition. For example, ATM deficiency, found in patients with T-cell prolymphocytic leukemia and B-cell chronic lymphocytic leukemia and breast cancer and CHK2 germ line mutations identified in sarcoma, breast cancer, ovarian cancer and brain tumors, have also been shown to be synthetically lethal in combination with PARP deficiency as well as deficiencies in other known HR pathway proteins (including RAD51, DSS1, RAD54, RPA1, NBS1, ATR, CHK1, CHK2, FANCD2, FANCA and FANCC).

Mutations in FANCC and FANCG have been shown in pancreatic cancer. Methylation of FANCF promoter has been found in ovarian, breast, cervical, lung carcinomas. The first clinical evidence that BRCA-mutated cancer may be sensitive to PARP inhibitor monotherapy comes from the preliminary data for the phase I trial of the oral, small molecule PARP inhibitor AZD2281. In an enriched Phase I population for BRCA mutation carriers, partial responses were seen in 4 out of 10 ovarian cancer patients with confirmed BRCA-1 mutations. Other PARP inhibitors, such as AG014699 and BSI-201, are currently known to be in phase II clinical trials both in combination with DNA damaging agents and as single agents in BRCA deficient tumors. Early indications are that these therapies show low toxicity. Anyway, compounds with high selectivity on PARP-1 are expected to be even less toxic in view of a chronic treatment schedule.

PARP-1 has also been implicated in angiogenesis. In particular, PARP-1 inhibition seems to result in decreased accumulation of the transcription hypoxia-inducible factor 1 important regulator of tumor cell adaptation to hypoxia. Pro-inflammatory stimuli trigger the release of pro-inflammatory mediators that induce the production of peroxynitrate and hydroxyl radicals, which in turn yield to DNA single strand breakage with consequent activation of PARP-1. Over activation of PARP-1 results in depletion of NAD+ and energy stores, culminating in cell dysfunction and necrosis. This cellular suicide mechanism has been implicated in the pathomechanism of stroke, myocardial ischemia, diabetes, diabetes-associated cardiovascular dysfunction, shock, traumatic central nervous system injury, arthritis, colitis, allergic encephalomyelitis and various other forms of inflammation. Of special interest is the enhancement by PARP-1 of nuclear factor kB-mediated transcription, which plays a central role in the expression of inflammatory cytokines, chemokines and inflammatory mediators.

The present invention concerns substituted isoquinolin-1 (2H)-one derivatives which selectively inhibit the activity of poly (ADP-ribose) polymerase PARP-1 with respect to poly (ADP-ribose) polymerase PARP-2. The compounds herein described are therefore useful in treating proliferative diseases such as cancer and in cardiovascular diseases, nervous system injury and inflammation.

In a study on nitrogen heterocycles in the Journal of the Chemical Society, Perkin Transactions 1, (1977), (9), 959-65, 3-phenyl-1(2H)-isoquinolinones are described. Isoquinolin-1(2H)-ones with pharmacological activity are described in Science of Synthesis (2005), 15, 839-906. Some patent applications describe isoquinoline derivatives for the treatment of glaucoma, EP389995, and of arteriosclerosis and hyperlipoproteinemia, EP591937. WO2002090334 in the name of KUDOS PHARM describes isoquinolinone derivatives used for inhibiting the PARP activity. WO2008092292 describes a method of treating pathological condition associated with a melatonin receptor using 2-substituted (2H)-isoquinolinones.

The present invention provides new 1(2H)-isoquinolinones which are endowed with selective inhibition activity to PARP-1 with respect to PARP-2 and are thus useful in therapy of cancer, cardiovascular diseases, nervous system injury and inflammation.

Accordingly, a first object of the present invention is to provide a compound of the formula (I):

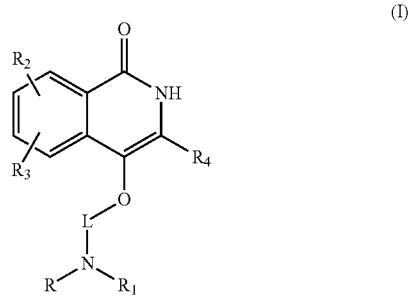

wherein L is an optionally substituted linear or branched $C_2$-$C_6$ alkyl, $C_3$-$C_7$ cycloalkyl group or, by including the nitrogen atom to which it is bonded, an optionally substituted heterocyclyl or heterocyclyl $C_1$-$C_6$ alkyl;

R and $R_1$ are independently hydrogen atom, an optionally substituted linear or branched $C_1$-$C_6$ alkyl, $C_3$-$C_7$ cycloalkyl, heterocyclyl, aryl, heteroaryl or $COR_5$ group or, taken together with the nitrogen atom to which they are bonded, form an optionally substituted heterocyclyl or heteroaryl group;

$R_2$ and $R_3$ are independently hydrogen or halogen atom; a cyano, nitro, $NHCOR_5$, $COR_5$, $NR_6R_7$, $NR_6COR_5$, $OR_8$, $SR_8$, $SOR_{11}$, $SO_2R_{11}$, $NHSOR_{11}$, $NHSO_2R_{11}$, $R_9R_{10}N$—$C_1$-$C_6$ alkyl, $R_9O$—$C_1$-$C_6$ alkyl group, or an optionally substituted linear or branched $C_1$-$C_6$ alkyl, $C_2$-$C_6$ alkenyl, $C_2$-$C_6$ alkynyl, $C_3$-$C_7$ cycloalkyl, heterocyclyl, aryl, or heteroaryl group;

$R_4$ is an optionally substituted linear or branched $C_1$-$C_6$ alkyl, $C_3$-$C_7$ cycloalkyl, $C_2$-$C_6$ alkenyl, $C_2$-$C_6$ alkynyl, aryl, aryl $C_1$-$C_6$ alkyl, aryl $C_3$-$C_7$ cycloalkyl, aryl $C_2$-$C_6$ alkenyl, aryl $C_2$-$C_6$ alkynyl, heterocyclyl, heterocyclyl $C_1$-$C_6$ alkyl, heterocyclyl $C_3$-$C_7$ cycloalkyl, heterocyclyl $C_2$-$C_6$ alkenyl, heterocyclyl $C_2$-$C_6$ alkynyl, heteroaryl, heteroaryl $C_1$-$C_6$ alkyl, heteroaryl $C_3$-$C_7$ cycloalkyl, heteroaryl $C_2$-$C_6$ alkenyl, heteroaryl $C_2$-$C_6$ alkynyl;

$R_5$ is hydrogen atom or $NR_6R_8$, $OR_8$, $SR_8$, $R_9R_{10}N$—$C_1$-$C_6$ alkyl, $R_9O$—$C_1$-$C_6$ alkyl, or an optionally substituted linear or branched $C_1$-$C_6$ alkyl, $C_2$-$C_6$ alkenyl, $C_2$-$C_6$ alkynyl, $C_3$-$C_7$ cycloalkyl, heterocyclyl, aryl or heteroaryl group;

$R_6$ and $R_7$ are independently hydrogen atom, an optionally substituted linear or branched $C_1$-$C_6$ alkyl, $C_2$-$C_6$ alkenyl, $C_2$-$C_6$ alkynyl, $C_3$-$C_7$ cycloalkyl, $R_9R_{10}N$—$C_2$-$C_6$ alkyl, $R_9O$—$C_2$-$C_6$ alkyl, heterocyclyl, aryl or heteroaryl group, or $R_6$ and $R_7$, taken together with the nitrogen atom to which they are bonded, may form an optionally substituted heterocyclyl group;

$R_8$ is hydrogen, a $COR_6$, $SOR_{11}$, $SO_2R_{11}$, $R_9R_{10}N$—$C_2$-$C_6$ alkyl or $R_9O$—$C_2$-$C_6$ alkyl group, or an optionally substituted linear or branched $C_1$-$C_6$ alkyl, $C_2$-$C_6$ alkenyl, $C_2$-$C_6$ alkynyl, $C_3$-$C_7$ cycloalkyl, heterocyclyl, aryl or heteroaryl group,
wherein $R_6$ is as defined above;

$R_9$ and $R_{10}$ are independently hydrogen, $COR_5$, or an optionally substituted linear or branched $C_1$-$C_6$ alkyl, $C_2$-$C_6$ alkenyl, $C_2$-$C_6$ alkynyl, $C_3$-$C_7$ cycloalkyl, heterocyclyl, aryl or heteroaryl group, or $R_9$ and $R_{10}$, taken together with the nitrogen atom to which they are bonded, may form an optionally substituted heterocyclyl group, wherein $R_5$ is as defined above;

$R_{11}$ is hydrogen atom, $NR_6R_7$, $OR_8$, $R_9R_{10}N$—$C_1$-$C_6$ alkyl, $R_9O$—$C_1$-$C_6$ alkyl, or an optionally substituted linear or branched $C_1$-$C_6$ alkyl, $C_2$-$C_6$ alkenyl, $C_2$-$C_6$ alkynyl, $C_7$-$C_7$ cycloalkyl, heterocyclyl, aryl or heteroaryl group, wherein $R_6$, $R_7$, $R_8$, $R_9$ and $R_{10}$ are as defined above;

or a pharmaceutically acceptable salt thereof.

A second object of the present invention relates to a screening method for the identification of compounds capable of binding several PARP proteins, as well the probes used in such method.

Therefore, there is provided also a screening method including the steps of:

a) providing a reaction mixture containing:
the PARP protein isoform under investigation,
a compound of formula (II):

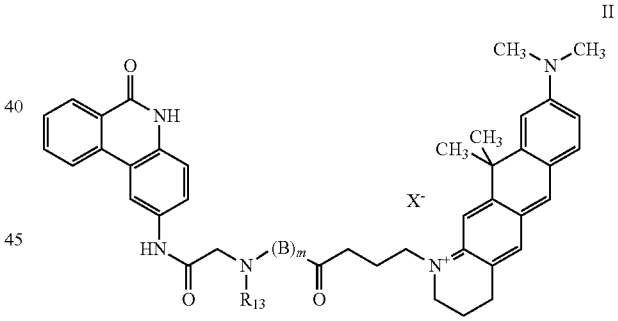

wherein $R_{13}$ is hydrogen atom or a methyl group, B is $(CH_2)_n$—NH group wherein n is 2 to 6; m is 0 or 1 and $X^-$ is a counterion, and
serial dilutions of the test compound;

b) comparing the polarization signal generated in the absence of the test compound with the one generated in the presence of different concentrations of the test compound, and c) evaluating the ability of the test compound to displace the compound of formula (II) as defined above indicated from a decreased fluorescence polarization level.

Compounds of formula (II) as defined above used as probes in the screening method, and a process for their preparation are also objects of the present invention.

The present invention also provides methods of synthesizing the isoquinolin-1(2H)-one derivatives of formula (I) as defined above through a process consisting of standard synthetic transformations.

As stated above, we have discovered that compounds of formula (I) as defined above are potent and selective PARP-1 inhibitors with respect to PARP-2 and are thus useful in the treatment of cancer, cardiovascular diseases, nervous system injury and for anti-inflammation therapy. Therefore, the present invention also provides methods for treating diseases mediated by the PARP-1 protein.

A preferred method of the present invention is to treat a disease mediated by PARP-1 protein selected from the group consisting of cancer, cardiovascular diseases, nervous system injury and inflammation.

Another preferred method of the present invention is to treat specific types of cancer including but not limited to: carcinoma such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage including leukaemia, acute lymphocytic leukaemia, acute lymphoblastic leukaemia, B-cell lymphoma, T-cell-lymphoma, Hodgkin's lymphoma, non-Hodgkin's lymphoma, hairy cell lymphoma and Burkitt's lymphoma; hematopoietic tumors of myeloid lineage, including acute and chronic myelogenous leukemias, myelodysplastic syndrome and promyelocytic leukaemia; tumors of mesenchymal origin, including fibrosarcoma and rhabdomyosarcoma; tumors of the central and peripheral nervous system, including astrocytoma neuroblastoma, glioma and schwannomas; other tumors, including melanoma, seminoma, teratocarcinoma, osteosarcoma, xeroderma pigmentosum, keratoxanthoma, thyroid follicular cancer and Kaposi's sarcoma.

Another preferred method of the present invention is to treat specific types of cardiovascular diseases including but not limited to: myocardial reperfusion injury, cardiomyopathy, diabetic cardiovascular dysfunction.

Another preferred method of the present invention is to treat specific types of central nervous system injury including but not limited to stroke, brain injury and neurodegenerative disorders.

The present invention further provides a method of treatment comprising a compound of formula (I) in combination with radiation therapy or chemotherapy regimen for simultaneous, separate or sequential use in anticancer therapy.

Moreover the invention provides a method for selectively inhibiting the PARP-1 protein activity which comprises contacting the said protein with an effective amount of a compound of formula (I).

The present invention also provides a pharmaceutical composition comprising one or more compounds of formula (I) or a pharmaceutically acceptable salt thereof and a pharmaceutically acceptable excipient, carrier or diluent.

The present invention also provides a pharmaceutical composition comprising a compound of formula (I) in combination with known cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrix metalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

Additionally, the invention provides a product or kit comprising a compound of formula (I) or a pharmaceutically acceptable salt thereof, as defined above, or pharmaceutical compositions thereof and one or more chemotherapeutic agents, as a combined preparation for simultaneous, separate or sequential use in anticancer therapy.

In yet another aspect, the invention provides a compound of formula (I) or a pharmaceutically acceptable salt thereof, as defined above, for use as a medicament.

Moreover the invention provides the use of a compound of formula (I) or a pharmaceutically acceptable salt thereof, as defined above, in the manufacture of a medicament for treating a disease mediated by PARP-1 protein.

Finally, the invention provides a compound of formula (I) or a pharmaceutically acceptable salt thereof, as defined above, for use in a method of treating a disease mediated by PARP-1 protein, preferably cancer, cardiovascular diseases, nervous system injury and inflammation.

The present invention also provides methods of synthesizing the substituted derivatives of formula (I) prepared through a process consisting of standard synthetic transformations.

If a chiral center or another form of an isomeric center is present in a compound of the present invention, all forms of such isomer or isomers, including enantiomers and diastereomers, are intended to be covered herein. Compounds containing a chiral center may be used as a racemic mixture, an enantiomerically enriched mixture, or the racemic mixture may be separated using well-known techniques and an individual enantiomer may be used alone. In cases in which compounds have unsaturated carbon-carbon double bonds, both the cis (Z) and trans (E) isomers are within the scope of this invention.

The term "pharmaceutically acceptable salt" of compounds of formula (I) refers to those salts that retain the biological effectiveness and properties of the parent compound. Such salts include acid addition salts with inorganic acids such as hydrochloric, hydrobromic, nitric, phosphoric, sulfuric, perchloric acid and the like, or with organic acids such as acetic, ascorbic, trifluoroacetic, propionic, glycolic, (D) or (L) lactic, (D) or (L) malic, oxalic, fumaric, maleic, methanesulphonic, ethanesulphonic, benzoic, p-toluenesulphonic, salicylic, cinnamic, mandelic, tartaric, citric, succinic, isethionic and malonic acid.

Pharmaceutically acceptable salts of the compounds of formula (I) also include the salts with inorganic or organic bases, e.g., alkali or alkaline-earth metals, especially sodium, potassium, calcium, ammonium or magnesium hydroxides, carbonates or bicarbonates, acyclic or cyclic amines, preferably methylamine, ethylamine, diethylamine, triethylamine, piperidine and the like.

In a preferred embodiment of the screening method that represents a second object of the present invention, the PARP protein and the compound of formula (II) as defined above are pre-mixed.

In another preferred embodiment of the screening method, the PARP protein and the test compound are pre-mixed. In a further preferred embodiment of the screening method, the PARP proteins are PARP-1, PARP-2 and PARP-3. The term "PARP protein" encompasses full-length native proteins as well as fragments thereof.

Unless otherwise specified, when referring to the compounds of formula (I) per se as well as to any pharmaceutical composition thereof or to any therapeutic treatment comprising them, the present invention includes all of the isomers, tautomers, hydrates, solvates, complexes, carriers, N-oxides and pharmaceutically acceptable salts of the compounds of this invention.

In cases wherein compounds may exist in tautomeric forms, such as keto-enol tautomers, each tautomeric form is contemplated as being included within this invention whether existing in equilibrium or predominantly in one form.

With the term halogen atom we intend a fluorine, chlorine, bromine or iodine atom.

With the term "linear or branched $C_1$-$C_6$ alkyl", we intend any of the groups such as, for instance, methyl, ethyl, n-propyl, isopropyl, n-butyl, isobutyl, tert-butyl, sec-butyl, n-pentyl, n-hexyl, and the like.

With the term "$C_2$-$C_6$ alkenyl" we intend an aliphatic $C_2$-$C_6$ hydrocarbon chain containing at least one carbon-carbon double bond which can be linear or branched. Representative examples include, but are not limited to, ethenyl, 1-propenyl, 2-propenyl, 1- or 2-butenyl, and the like.

With the term "$C_2$-$C_6$ alkynyl" we intend an aliphatic $C_2$-$C_6$ hydrocarbon chain containing at least one carbon-carbon triple bond and which can be linear or branched. Representative examples include, but are not limited to, ethynyl, 1-propynyl, 2-propynyl, 1- or 2-butynyl, and the like.

With the term "$C_3$-$C_7$ cycloalkyl" we intend, unless otherwise provided, a 3- to 7-membered all-carbon monocyclic ring, which may contain one or more double bonds but does not have a completely conjugated π-electron system. Examples of cycloalkyl groups, without limitation, are cyclopropane, cyclobutane, cyclopentane, cyclopentene, cyclohexane, cyclohexene and cyclohexadiene.

With the term "heterocyclyl" we intend a 3- to 8-membered, saturated or partially unsaturated carbocyclic ring where one or more carbon atoms are replaced by heteroatoms such as nitrogen, oxygen and sulfur. Non limiting examples of heterocyclyl groups are, for instance, pyrane, pyrrolidine, pyrroline, imidazoline, imidazolidine, pyrazolidine, pyrazoline, thiazoline, thiazolidine, dihydrofuran, tetrahydrofuran, 1,3-dioxolane, piperidine, piperazine, morpholine and the like.

The term "aryl" refers to a mono-, bi- or poly-carbocyclic hydrocarbon with from 1 to 4 ring systems, optionally further fused or linked to each other by single bonds, wherein at least one of the carbocyclic rings is "aromatic", wherein the term "aromatic" refers to completely conjugated π-electron bond system. Non limiting examples of such aryl groups are phenyl, α- or β-naphthyl or biphenyl groups.

The term "heteroaryl" as used herein refers to aromatic heterocyclic rings, typically 5- to 8-membered heterocycles with from 1 to 3 heteroatoms selected among N, O or S; the heteroaryl ring can be optionally further fused or linked to aromatic and non-aromatic carbocyclic and heterocyclic rings. Non limiting examples of such heteroaryl groups are, for instance, pyridyl, pyrazinyl, pyrimidinyl, pyridazinyl, indolyl, imidazolyl, thiazolyl, isothiazolyl, pyrrolyl, phenylpyrrolyl, furyl, phenyl-furyl, oxazolyl, isoxazolyl, pyrazolyl, thienyl, benzothienyl, isoindolinyl, benzoimidazolyl, indazolyl, quinolinyl, isoquinolinyl, 1,2,3-triazolyl, 1-phenyl-1,2,3-triazolyl, 2,3-dihydroindolyl, 2,3-dihydrobenzofuranyl, 2,3-dihydrobenzothiophenyl; benzopyranyl, 2,3-dihydrobenzoxazinyl, 2,3-dihydroquinoxalinyl and the like.

According to the present invention and unless otherwise provided, any of the above L, R—$R_{11}$ group may be optionally substituted, in any of their free positions, by one or more groups, for instance 1 to 6 groups, independently selected from: halogen, nitro, oxo groups (=O), cyano, $C_1$-$C_6$ alkyl, polyfluorinated alkyl, polyfluorinated alkoxy, $C_2$-$C_6$ alkenyl, $C_2$-$C_6$ alkynyl, hydroxyalkyl, aryl, arylalkyl, heteroaryl, heteroarylalkyl, heterocyclyl, heterocyclylalkyl, $C_3$-$C_7$ cycloalkyl, hydroxy, alkoxy, aryloxy, heterocyclyloxy, methylenedioxy, alkylcarbonyloxy, arylcarbonyloxy, cycloalkenyloxy, heterocyclylcarbonyloxy, alkylideneaminooxy, carboxy, alkoxycarbonyl, aryloxycarbonyl, cycloalkyloxycarbonyl, heterocyclylalkyloxycarbonyl, amino, ureido, alkylamino, dialkylamino, arylamino, diarylamino, heterocyclylamino, formylamino, alkylcarbonylamino, arylcarbonylamino, heterocyclylcarbonylamino, aminocarbonyl, alkylaminocarbonyl, dialkylaminocarbonyl, arylaminocarbonyl, heterocyclylaminocarbonyl, alkoxycarbonylamino, hydroxyaminocarbonyl alkoxyimino, alkylsulphonylamino, arylsulphonylamino, heterocyclylsulphonylamino, formyl, alkylcarbonyl, arylcarbonyl, cycloalkylcarbonyl, heterocyclylcarbonyl, alkylsulphonyl, arylsulphonyl, aminosulphonyl, alkylaminosulphonyl, dialkylaminosulphonyl, arylaminosulphonyl, heterocyclylaminosulphonyl, arylthio, alkylthio, phosphonate and alkylphosphonate. In their turn, whenever appropriate, each of the above substituent may be further substituted by one or more of the aforementioned groups.

Preferably, such substituents are selected from halogen, cyano, nitro, $NHCOR_5$, $COR_5$, $NR_6R_7$, $NR_6COR_5$, $OR_8$, $SR_8$, $SOR_{11}$, $SO_2R_{11}$, $NHSOR_{11}$, $NHSO_2R_{11}$, $R_9R_{10}N$—$C_1$-$C_6$ alkyl, $R_9O$—$C_1$-$C_6$ alkyl, an optionally further substituted linear or branched $C_1$-$C_6$ alkyl, $C_3$-$C_7$ cycloalkyl, heterocyclyl, aryl and heteroaryl group, wherein $R_5$, $R_6$, $R_7$, $R_8$, $R_9$, $R_{10}$ and $R_{11}$ are as above defined.

With the term polyfluorinated alkyl or polyfluorinated alkoxy we intend any of the above linear or branched $C_1$-$C_6$ alkyl or alkoxy groups which are substituted by more than one fluorine atom such as, for instance, trifluoromethyl, trifluoroethyl, 1,1,1,3,3,3-hexafluoropropyl, trifluoromethoxy and the like.

With the term hydroxyalkyl we intend any of the above $C_1$-$C_6$ alkyl, bearing an hydroxyl group such as, for instance, hydroxymethyl, 2-hydroxyethyl, 3-hydroxypropyl and the like.

From all of the above, it is clear to the skilled person that any group whose name is a composite name such as, for instance, arylamino, has to be intended as conventionally construed by the parts from which it derives, e.g. by an amino group which is further substituted by aryl, wherein aryl is as above defined.

Likewise, any of the terms such as, for instance, alkylthio, alkylamino, dialkylamino, alkoxycarbonyl, alkoxycarbonylamino, heterocyclylcarbonyl, heterocyclylcarbonylamino, cycloalkyloxycarbonyl and the like, include groups wherein the alkyl, alkoxy, aryl, $C_3$-$C_7$ cycloalkyl and heterocyclyl moieties are as above defined.

Preferably, the present invention provides compounds of the formula (I) as defined above characterized in that L represents an optionally substituted linear or branched $C_2$-$C_6$ alkyl or, by including the nitrogen atom to which it is bonded, an optionally substituted heterocyclyl or heterocyclyl $C_1$-$C_6$ alkyl;

R and $R_1$ are independently hydrogen atom, an optionally substituted linear or branched $C_1$-$C_6$ alkyl or $COR_5$ group or, taken together with the nitrogen atom to which they are bonded, form an optionally substituted heterocyclyl or heteroaryl group;

$R_2$ and $R_3$ are independently hydrogen or halogen atom; a nitro, amino, hydroxy, $COR_5$, or an optionally substituted linear or branched $C_1$-$C_6$ alkyl group;

$R_4$ is an optionally substituted aryl or heteroaryl group;

$R_5$ is an optionally substituted linear or branched $C_1$-$C_6$ alkyl;

or a pharmaceutically acceptable salt thereof.

More preferably, there are provided compounds of the formula (I) as defined above characterized in that L is an optionally substituted linear or branched $C_2$-$C_4$ alkyl group or, by including the nitrogen atom to which it is bonded, an optionally substituted heterocyclyl;

R and $R_1$ are independently hydrogen atom, an optionally substituted linear or branched $C_1$-$C_4$ alkyl or $COR_5$ group or, taken together with the nitrogen atom to which they are bonded, form an optionally substituted piperidinyl, pyrrolidinyl, piperazinyl, or pyrrolyl group;

$R_2$ and $R_3$ are independently hydrogen, chlorine or fluorine atom; or a nitro, amino, hydroxy, $COR_5$, or an optionally substituted linear or branched $C_1$-$C_4$ alkyl group;

$R_4$ is an optionally substituted phenyl or thienyl group;

$R_5$ is an optionally substituted linear or branched $C_1$-$C_4$ alkyl group;

or a pharmaceutically acceptable salt thereof.

Specifically preferred compounds according to the present invention are listed below:

1. 4-(2-Amino-ethoxy)-3-phenyl-2H-isoquinolin-1-one,
2. N-[2-(1-oxo-3-phenyl-1,2-dihydro-isoquinolin-4-yloxy)-ethyl]-acetamide,
3. 4-(3-Amino-propoxy)-3-phenyl-2H-isoquinolin-1-one,
4. N-[3-(1-Oxo-3-phenyl-1,2-dihydro-isoquinolin-4-yloxy)-propyl]-acetamide,
5. 3-Phenyl-4-(3-piperidin-1-yl-propoxy)-2H-isoquinolin-1-one,
6. 3-Phenyl-4-(2-piperazin-1-yl-ethoxy)-2H-isoquinolin-1-one,
7. 4-[2-(4-Acetyl-piperazin-1-yl)-ethoxy]-3-phenyl-2H-isoquinolin-1-one,
8. N-[3-(1-Oxo-3-phenyl-1,2-dihydro-isoquinolin-4-yloxy)-propyl]-benzamide,
9. 3-(3-Methoxy-phenyl)-4-(2-piperidin-1-yl-ethoxy)-2H-isoquinolin-1-one,
10. 3-(3-Methoxy-phenyl)-4-(3-piperidin-1-yl-propoxy)-2H-isoquinolin-1-one,
11. 4-(2-Amino-ethoxy)-3-(3-methoxy-phenyl)-2H-isoquinolin-1-one,
12. 4-(3-Methylamino-propoxy)-3-phenyl-2H-isoquinolin-1-one,
13. 3-Phenyl-4-(2-pyrrol-1-yl-ethoxy)-2H-isoquinolin-1-one,
14. 3-Phenyl-4-(3-piperazin-1-yl-propoxy)-2H-isoquinolin-1-one,
15. 3-Phenyl-4-(3-pyrrol-1-yl-propoxy)-2H-isoquinolin-1-one,
16. 4-(2-Methylamino-ethoxy)-3-phenyl-2H-isoquinolin-1-one,
17. 4-(2-Dimethylamino-ethoxy)-3-phenyl-2H-isoquinolin-1-one,
18. 4-(3-Diethylamino-propoxy)-3-phenyl-2H-isoquinolin-1-one,
19. 4-[2-(4-Methyl-piperazin-1-yl)-ethoxy]-3-phenyl-2H-isoquinolin-1-one,
20. 4-[3-(4-Methyl-piperazin-1-yl)-propoxy]-3-phenyl-2H-isoquinolin-1-one,
21. 3-Phenyl-4-(3-pyrrolidin-1-yl-propoxy)-2H-isoquinolin-1-one,
22. 4-(4-Amino-butoxy)-3-phenyl-2H-isoquinolin-1-one,
23. 3-(4-Methoxy-phenyl)-4-(3-piperidin-1-yl-propoxy)-2H-isoquinolin-1-one,
24. 4-(2-Amino-ethoxy)-3-(4-methoxy-phenyl)-2H-isoquinolin-1-one,
25. 4-(2-Amino-ethoxy)-7-fluoro-3-(4-methoxy-phenyl)-2H-isoquinolin-1-one,
26. 4-(2-Amino-ethoxy)-3-(4-hydroxy-phenyl)-2H-isoquinolin-1-one,
27. 3-(4-Hydroxy-phenyl)-4-(3-piperidin-1-yl-propoxy)-2H-isoquinolin-1-one,
28. 4-(2-Amino-ethoxy)-7-fluoro-3-(4-hydroxy-phenyl)-2H-isoquinolin-1-one,
29. 4-(2-Amino-ethoxy)-3-thiophen-3-yl-2H-isoquinolin-1-one,
30. 7-Acetyl-3-phenyl-4-(2-piperidin-1-yl-ethoxy)-2H-isoquinolin-1-one,
31. 6-Nitro-3-phenyl-4-(2-piperidin-1-yl-ethoxy)-2H-isoquinolin-1-one,
32. 4-(2-Amino-ethoxy)-3-(3-hydroxy-phenyl)-2H-isoquinolin-1-one,
33. 3-(3-Hydroxy-phenyl)-4-(3-piperidin-1-yl-propoxy)-2H-isoquinolin-1-one,
34. 6-Nitro-3-phenyl-4-(3-piperidin-1-yl-propoxy)-2H-isoquinolin-1-one,
35. 7-Nitro-3-phenyl-4-(3-piperidin-1-yl-propoxy)-2H-isoquinolin-1-one,
36. 7-Amino-3-phenyl-4-(3-piperidin-1-yl-propoxy)-2H-isoquinolin-1-one,
37. 7-Chloro-3-phenyl-4-(3-piperidin-1-yl-propoxy)-2H-isoquinolin-1-one,
38. 7-Fluoro-3-phenyl-4-(3-piperidin-1-yl-propoxy)-2H-isoquinolin-1-one,
39. 4-(2-Amino-ethoxy)-7-fluoro-3-phenyl-2H-isoquinolin-1-one,
40. 6-Amino-3-phenyl-4-(3-piperidin-1-yl-propoxy)-2H-isoquinolin-1-one,
41. 6-Chloro-3-phenyl-4-(3-piperidin-1-yl-propoxy)-2H-isoquinolin-1-one,
42. 6-Fluoro-3-phenyl-4-(3-piperidin-1-yl-propoxy)-2H-isoquinolin-1-one,
43. 7-Fluoro-3-(3-methoxy-phenyl)-4-(3-piperidin-1-yl-propoxy)-2H-isoquinolin-1-one,
44. 3-(3-Chloro-phenyl)-4-(3-piperidin-1-yl-propoxy)-2H-isoquinolin-1-one,
45. 7-Fluoro-3-(3-hydroxy-phenyl)-4-(3-piperidin-1-yl-propoxy)-2H-isoquinolin-1-one,
46. 4-(2-Amino-ethoxy)-7-fluoro-3-(3-methoxy-phenyl)-2H-isoquinolin-1-one,
47. 4-(2-Amino-ethoxy)-7-fluoro-3-(3-hydroxy-phenyl)-2H-isoquinolin-1-one,
48. 4-(2-Amino-ethoxy)-3-(3-chloro-phenyl)-2H-isoquinolin-1-one,
49. 4-(2-Amino-ethoxy)-5-methyl-3-phenyl-2H-isoquinolin-1-one,
50. 4-(2-Amino-ethoxy)-3-(3-chloro-phenyl)-7-fluoro-2H-isoquinolin-1-one,
51. 3-Phenyl-4-(2-piperidin-1-yl-ethoxy)-2H-isoquinolin-1-one,
52. 4-(2-Diethylamino-ethoxy)-3-phenyl-2H-isoquinolin-1-one,
53. 3-Phenyl-4-(2-pyrrolidin-1-yl-ethoxy)-2H-isoquinolin-1-one,
54. 4-(2-Morpholin-4-yl-ethoxy)-3-phenyl-2H-isoquinolin-1-one,
55. 5-Methyl-3-phenyl-4-(3-piperidin-1-yl-propoxy)-2H-isoquinolin-1-one,
56. 4-(2-Amino-ethoxy)-7-fluoro-5-methyl-3-phenyl-2H-isoquinolin-1-one
57. 7-Fluoro-5-methyl-3-phenyl-4-(3-piperidin-1-yl-propoxy)-2H-isoquinolin-1-one,
58. 4-(2-Amino-ethoxy)-3-(3-chloro-phenyl)-5-methyl-2H-isoquinolin-1-one,
59. 3-(3-Chloro-phenyl)-5-methyl-4-(3-piperidin-1-yl-propoxy)-2H-isoquinolin-1-one,
60. 4-(2-Amino-ethoxy)-3-(3-chloro-phenyl)-7-fluoro-5-methyl-2H-isoquinolin-1-one, 61. 3-(3-Chloro-phenyl)-7-fluoro-5-methyl-4-(3-piperidin-1-yl-propoxy)-2H-isoquinolin-1-one,
62. 4-(2-Amino-ethoxy)-7-fluoro-3-(4-methoxy-phenyl)-5-methyl-2H-isoquinolin-1-one,
63. 7-Fluoro-3-(4-methoxy-phenyl)-5-methyl-4-(3-piperidin-1-yl-propoxy)-2H-isoquinolin-1-one,
64. 4-(2-Amino-ethoxy)-7-fluoro-3-(3-methoxy-phenyl)-5-methyl-2H-isoquinolin-1-one,
65. 7-Fluoro-3-(3-methoxy-phenyl)-5-methyl-4-(3-piperidin-1-yl-propoxy)-2H-isoquinolin-1-one,
66. 4-(2-Amino-ethoxy)-3-(4-chloro-3-methoxy-phenyl)-7-fluoro-5-methyl-2H-isoquinolin-1-one,
67. 3-(4-Chloro-3-methoxy-phenyl)-7-fluoro-5-methyl-4-(3-piperidin-1-yl-propoxy)-2H-isoquinolin-1-one,
68. 4-(2-Amino-ethoxy)-3-(3-chloro-4-methoxy-phenyl)-7-fluoro-5-methyl-2H-isoquinolin-1-one,
69. 3-(3-Chloro-4-methoxy-phenyl)-7-fluoro-5-methyl-4-(3-piperidin-1-yl-propoxy)-2H-isoquinolin-1-one,
70. 4-(2-Amino-ethoxy)-3-(3-chloro-4-methoxy-phenyl)-5-methyl-2H-isoquinolin-1-one,
71. 3-(3-Chloro-4-methoxy-phenyl)-5-methyl-4-(3-piperidin-1-yl-propoxy)-2H-isoquinolin-1-one,
72. 4-(2-Amino-ethoxy)-3-(4-chloro-3-methoxy-phenyl)-5-methyl-2H-isoquinolin-1-one,
73. 3-(4-Chloro-3-methoxy-phenyl)-5-methyl-4-(3-piperidin-1-yl-propoxy)-2H-isoquinolin-1-one,
74. 4-(2-Amino-ethoxy)-3-(3-methoxy-phenyl)-5-methyl-2H-isoquinolin-1-one,
75. 3-(3-Methoxy-phenyl)-5-methyl-4-(3-piperidin-1-yl-propoxy)-2H-isoquinolin-1-one,
76. 4-(2-Amino-ethoxy)-3-(4-methoxy-phenyl)-5-methyl-2H-isoquinolin-1-one,
77. 3-(4-Methoxy-phenyl)-5-methyl-4-(3-piperidin-1-yl-propoxy)-2H-isoquinolin-1-one,
78. 4-(2-Amino-ethoxy)-7-fluoro-3-(4-phenoxy-phenyl)-2H-isoquinolin-1-one,
79. 7-Fluoro-3-(4-phenoxy-phenyl)-4-(3-piperidin-1-yl-propoxy)-2H-isoquinolin-1-one,
80. 4-(2-Amino-ethoxy)-3-benzyl-7-fluoro-2H-isoquinolin-1-one,
81. 3-Benzyl-7-fluoro-4-(3-piperidin-1-yl-propoxy)-2H-isoquinolin-1-one,
82. 4-(2-Amino-ethoxy)-8-fluoro-3-phenyl-2H-isoquinolin-1-one,
83. 8-Fluoro-3-phenyl-4-(3-piperidin-1-yl-propoxy)-2H-isoquinolin-1-one,
84. 4-[2-(dimethylamino)ethoxy]-7-fluoro-3-phenylisoquinolin-1(2H)-one,
85. 7-fluoro-3-phenyl-4-(piperidin-4-yloxy)isoquinolin-1(2H)-one,
86. 4-(3-aminopropoxy)-7-fluoro-3-phenylisoquinolin-1(2H)-one hydrochloride,
87. 4-[3-(benzylamino)propoxy]-7-fluoro-3-phenylisoquinolin-1(2H)-one,
88. 4-[2-(diethylamino)ethoxy]-7-fluoro-3-phenylisoquinolin-1(2H)-one,
89. 7-fluoro-4-[2-(4-methylpiperazin-1-yl)ethoxy]-3-phenylisoquinolin-1(2H)-one and
90. 7-fluoro-3-phenyl-4-[2-(phenylamino)ethoxy]isoquinolin-1(2H)-one.

The present invention also provides processes for the preparation of compounds of formula (I) as defined above. Accordingly, a process of the present invention comprises the following steps:

either
step 1) alkylating a compound of formula (III):

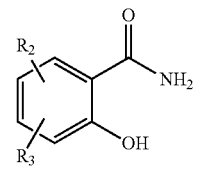

III wherein $R_2$ and $R_3$ are as defined above, with a compound of formula (IV):

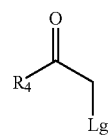

IV wherein $R_4$ is as defined above and Lg represents a suitable leaving group;
step 2) cyclodehydrating the resultant compound of formula (V):

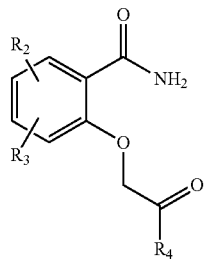

V wherein $R_2$, $R_3$ and $R_4$ are as defined above;
step 3) rearranging the resultant compound of formula (VI):

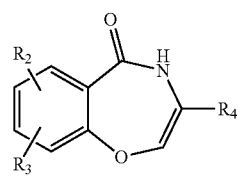

VI wherein $R_2$, $R_3$ and $R_4$ are as defined above, so as to obtain a compound of formula (VII):

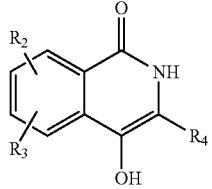

VII wherein $R_2$, $R_3$ and $R_4$ are as defined above;
or
step 4) reacting a compound of formula (VIII) with compound of formula (IX):

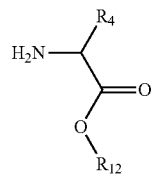

VIII

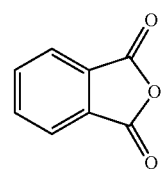

IX wherein $R_4$ is as defined above and $R_{12}$ is a $C_1$-$C_6$ alkyl or an aryl $C_1$-$C_6$ alkyl group;
step 3a) rearranging the resultant compound of formula (X):

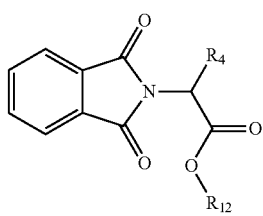

X wherein $R_4$ and $R_{12}$ are as defined above, so as to obtain a compound of formula (VII) as above defined wherein $R_2$ and $R_3$ are both hydrogen atoms;
and
step 5) alkylating a compound of formula (VII) as defined above with
either a compound of formula (XI):

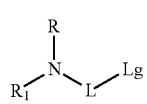

(XI)

wherein R, $R_1$, L and Lg are as defined above, so as to obtain a compound of formula (I) as defined above;

or with a compound of formula (XII) X'-L-Lg wherein L is an optionally substituted linear or branched $C_2$-$C_6$ alkyl or $C_3$-$C_7$ cycloalkyl group, Lg is as defined above and X' represents a suitable leaving group or a group wich can be converted in a suitable living group;
step 6) reacting the resultant compound of formula (XIII):

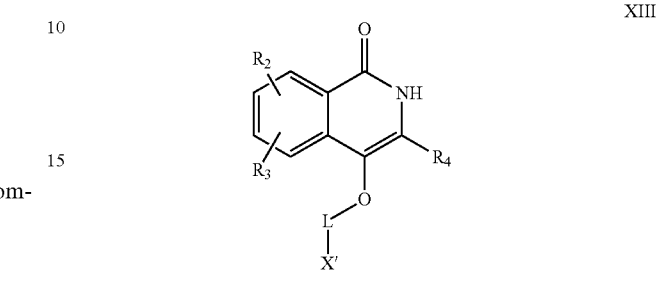

XIII wherein $R_2$, $R_3$, $R_4$, and X' are as defined above, L is an optionally substituted linear or branched $C_2$-$C_6$ alkyl or $C_3$-$C_7$ cycloalkyl group, with a compound of formula (XIV): R—NH—$R_1$ wherein R and $R_1$ are as defined above so as to obtain a compound of formula (I) as defined above.

If necessary or wanted, the process comprises converting a compound of formula (I) into a different compound of formula (I) by known chemical reactions; and/or, if desired, converting a compound of formula (I) into a pharmaceutically acceptable salt thereof or converting a salt into a free compound of formula (I).

The known chemical reactions for possible conversions of compounds of the formula (I) or formula (XIII) into a different compound of the formula (I) or formula (XIII) are for example:

Conversion A) Deprotection, if necessary, of a compound of formula (I) as defined above when R and/or $R_1$ contain a protective group so as to obtain the corresponding unprotected compound of formula (I) as defined above.

Conversion B) Conversion of a compound of formula (I) as defined above wherein $R_4$ is an aryl, aryl $C_1$-$C_6$ alkyl, heteroaryl or heteroaryl $C_1$-$C_6$ alkyl group substituted in any free positions of the ring by —$OR_{12}$, wherein $R_{12}$ is as defined above, into a compound of formula (I) as defined above wherein $R_4$ is an aryl, aryl $C_1$-$C_6$ alkyl, heteroaryl or heteroaryl $C_1$-$C_6$ alkyl group substituted in any free positions by —OH.

Conversion C) Conversion of a compound of formula (I) as defined above wherein $R_2$ or $R_3$ is a nitro group into a compound of formula (I) as defined above wherein $R_2$ or $R_3$ is an amino group.

Conversion D) Conversion of a compound of formula (I) as defined above wherein $R_2$ or $R_3$ is an amino group, into a compound of formula (I) as defined above wherein $R_2$ or $R_3$ is halogen atom such as Cl, Br, F or I through the corresponding diazo-derivative.

Conversion E) Conversion of a compound of formula (I) as above defined wherein R and/or $R_1$ are hydrogen atoms into a compound of formula (I) wherein R and $R_1$ are as defined above but not $COR_5$ or both hydrogen atoms.

Conversion F) Conversion of a compound of formula (I) as defined above wherein R and/or $R_1$ are hydrogen atoms into a compound of formula (I) as defined above wherein R or $R_1$ is $COR_5$ wherein $R_5$ is as defined above.

Conversion G) Conversion of a compound of formula (XIII) as defined above, into another compound of formula (XIII) by the procedures described under Conversion A to D or by converting the group X' into a suitable living group.

All the above processes are analogy processes which can be carried out according to well known methods and under suitable conditions known in the art.

Scheme 1 below illustrates the step sequence of the process according to the present invention.

romethane and the like, at a temperature ranging from 0° C. to reflux so as to obtain a compound of formula (V), as defined above.

According to step 2 of the process, a compound of formula (V), as defined above, is refluxed in an apparatus suitable for the continuous removal of water in the presence of a catalytic amount of acid, such as p-toluene sulphonic acid, camphorsulphonic acid and the like, in solvents such as ethyl acetate, benzene, toluene, xylene and the like, so as to afford a com-

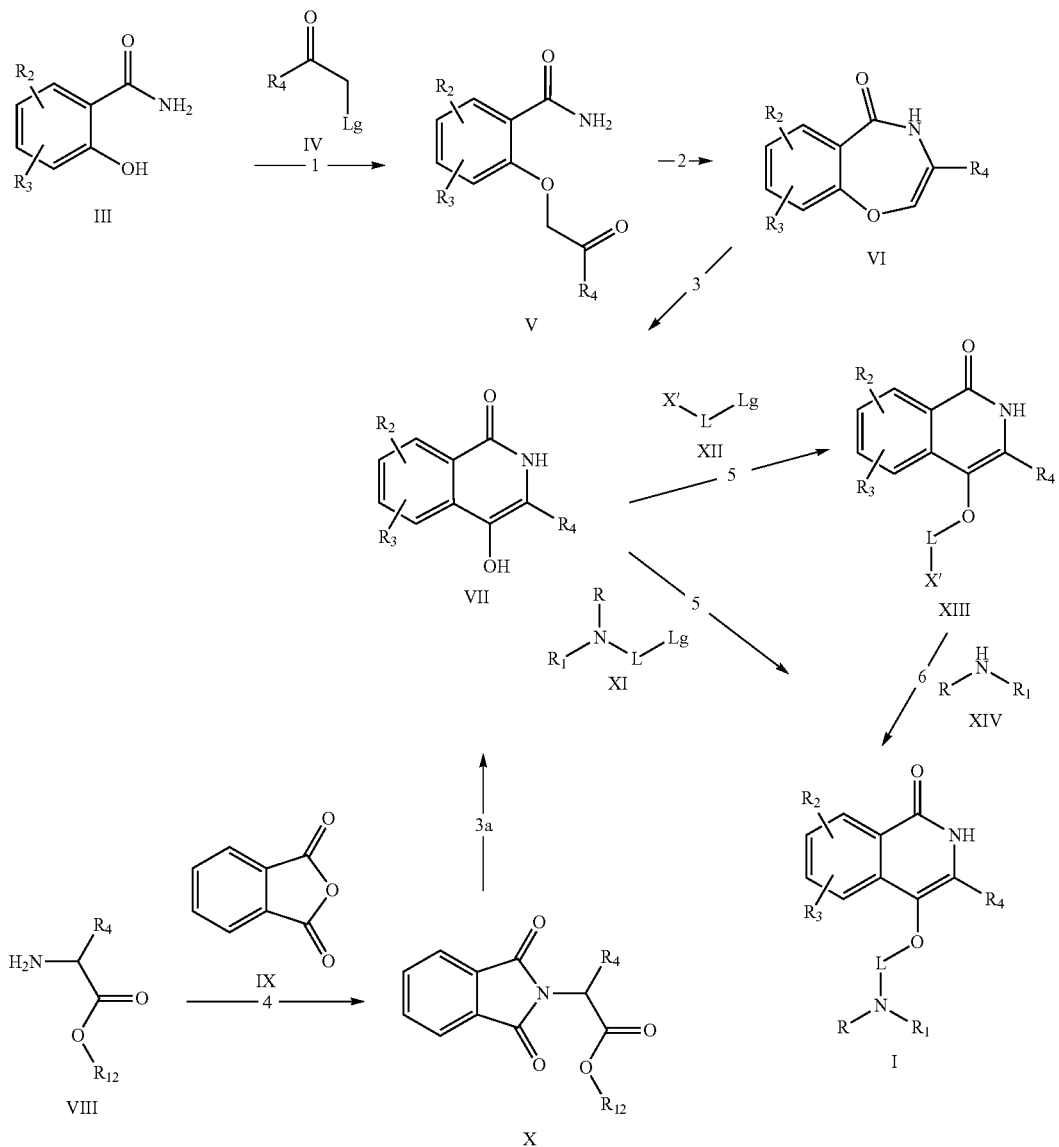

SCHEME 1

According to step 1 of the process, a compound of formula (III), as defined above, is reacted with a compound of formula (IV), wherein Lg is a leaving group such as halogen like bromine, chlorine or iodine, p-toluensulphonate, methanesulphonate or trifluoromethanesulphonate, in the presence of a base, such as sodium, potassium or cesium carbonate, sodium or potassium hydroxide, triethylamine, diisopropylethylamine and the like, in a suitable solvent, such as N,N-dimethylformamide, N,N-dimethylacetamide, acetonitrile, acetone, ethyl acetate, tetrahydrofuran, dioxane, dichlopound of formula (VI), as defined above. The cyclodehydration can be carried out as described in Wang, S. et al, J. Bioorg. Med. Chem. Lett. 2002, 12, 2367-2370.

According to step 3 of the process, a compound of formula (VI), as defined above, is warmed in a suitable solvent, such as N,N-dimethylformamide, N,N-dimethylacetamide, tetrahydrofuran, dioxane and the like, in the presence of a base, such as sodium hydride, sodium amide and the like under an inert atmosphere to give a compound of formula (VII), as defined above. The rearrangement can be carried out as described in Schenker, K. Helv. Chim. Acta 1968, 51, 413-21; or in Wang, S. et al., J. Bioorg. Med. Chem. Lett. 2002, 12, 2367-2370.

According to step 4 of the process, a compound of formula (VIII), as defined above, used as a racemic mixture, an enantiomerically enriched mixture, or as individual enantiomer, can be reacted neat with a compound of formula (IX) as defined above, under microwave irradiations, to give a compound of formula (X), as defined above, as described in Peukert, S. et al., Synthesis 2005, 9, 1550-1554.

According to step 3a of the process, treatment of the resultant compound (X), as defined above, obtained in step 4 as a racemic mixture, an enantiomerically enriched mixture, or as individual enantiomer, with a base, such as sodium methoxide, sodium ethoxide and the like, in a solvent such as methanol or ethanol at reflux resulted in the formation of compound (VII), as defined above. The rearrangement can be carried out as described in Peukert, S. et al. Synthesis 2005, 9, 1550-1554.

According to step 5 of the process, a compound of formula (VII), as defined above, is reacted with a compound of formula (XI), as defined above, in the presence of a suitable base, such as sodium, potassium or cesium carbonate, sodium or potassium hydrogencarbonate, triethylamine, diisopropylethylamine, pyridine, sodium or potassium hydride and the like, in a suitable solvent, such as N,N-dimethylformamide, N,N-dimethylacetamide, acetonitrile, acetone, methanol, ethanol, tetrahydrofuran, dioxane, dichloromethane and the like, at a temperature ranging from 0° C. to reflux to give a compound of formula (I), as defined above. When Lg is bromine the reaction is preferentially carried out at room temperature in N,N-dimethylacetamide as the solvent, using cesium carbonate as the base. When Lg is chlorine, potassium iodide is added and the reaction is preferentially carried out under microwave irradiations using potassium carbonate as the base and methanol as the solvent.

A compound of formula (VII), as defined above, is also reacted with a compound of formula (XII), as defined above, wherein Lg and X' are as defined above, in the presence of a suitable base, such as, for instance, sodium, potassium or cesium carbonate, sodium or potassium hydrogencarbonate, triethylamine, diisopropylethylamine, pyridine, sodium or potassium hydride and the like, in a solvent like, for instance, N,N-dimethylformamide, N,N-dimethylacetamide, acetonitrile, acetone, methanol, ethanol, tetrahydrofuran, dioxane, dichloromethane and the like, at a temperature ranging from 0° C. to reflux to give a compound of formula (XIII), as defined above.

According to step 6 of the process, a compound of formula (XIII), as defined above, is then reacted with a compound of formula (XIV), as defined above, in the presence of a base such as, for instance, sodium, potassium or cesium carbonate, sodium or potassium hydrogencarbonate, triethylamine, diisopropylethylamine, pyridine and the like, in a suitable solvent such as acetonitrile, dioxane, methanol, ethanol or N,N-dimethylformamide at a temperature ranging from 0° C. to reflux, or, alternatively, using microwave conditions, to give a compound of formula (I), as defined above.

According to conversion A of the process, when R or $R_1$ in a compound of formula (I) contain nitrogen protective groups such as tert-butoxycarbonyl, 4-methoxybenzyl, 2,4-dimethoxybenzyl and triphenylmethyl protective groups, a different compound of formula (I) as defined above can be obtained by removing these protective groups under acidic conditions, preferably in the presence of an inorganic or organic acid such as hydrochloric, trifluoroacetic or methanesulphonic acid, boron tribromide or aluminium trichloride in a suitable solvent such as dichloromethane, dichloroethane, dioxane, a lower alcohol, such as methanol or ethanol, at a temperature ranging from room temperature to reflux.

When R or $R_1$ in a compound of formula (I) contain nitrogen protective groups such as benzyloxycarbonyl and the like, a different compound of formula (I) as defined above can be obtained by removing these protective groups under reducing conditions, such as, for instance, in the presence of hydrogen and a hydrogenation catalyst in a suitable solvent such as ethanol, methanol, ethyl acetate, or a mixture thereof. The catalyst is usually a metal, most often a palladium derivative such as, for instance, palladium on carbon, palladium hydroxide or palladium black.

When R or $R_1$ in a compound of formula (I) contain nitrogen protective groups such as methoxycarbonyl, ethoxycarbonyl, 9-fluorenylmethoxycarbonyl and the like, a different compound of formula (I) as defined above can be obtained by removing these protective groups under basic conditions such as, for instance, sodium, potassium or cesium carbonate, sodium, potassium or barium hydroxide, hydrazine, piperidine, morpholine and the like in a suitable solvent such as methanol, ethanol, water, N,N-dimethylformamide, N,N-dimethylacetamide and the like, at a temperature ranging from room temperature to reflux.

According to conversion B of the process, a compound of formula (I) as defined above, wherein $R_4$ is an aryl, aryl $C_1$-$C_6$ alkyl, heteroaryl or heteroaryl $C_1$-$C_6$ alkyl group substituted in any free positions of the ring by —$OR_{12}$, wherein $R_{12}$ is as defined above, can be converted into a different compound of formula (I) wherein $R_4$ is an aryl, aryl $C_1$-$C_6$ alkyl, heteroaryl or heteroaryl $C_1$-$C_6$ alkyl group is substituted in any free positions by —OH by using an acid such as hydrobromic acid, boron tribromide, aluminium chloride and the like, in a suitable solvent such as acetonitrile, dichloromethane, dichloroethane, acetic acid, acetic anhydride and the like, at a temperature ranging from 0° C. to reflux.

According to conversion C of the process, a compound of formula (I) as defined above, wherein $R_2$ or $R_3$ is a nitro group, can be converted into a different compound of formula (I) wherein $R_2$ or $R_3$ is an amino group, by reaction with a suitable reducing agent such as molecular hydrogen, cyclohexene, cyclohexadiene, formic acid, ammonium formate and the like, in the presence of a hydrogenation catalyst such as, for instance, palladium on carbon, palladium hydroxide, palladium black, Ni Raney and the like, in a suitable solvent, such as methanol, ethanol, dioxane and the like, at a temperature ranging from room temperature to reflux. Alternatively, this conversion can be accomplished with metals such as tin, iron, zinc and the like in the presence of a protic acid such as hydrochloric, acetic acid and the like optionally in a suitable solvent such as methanol, ethanol at a temperature ranging from room temperature to reflux.

According to conversion D of the process, a compound of formula (I) as defined above, wherein $R_2$ or $R_3$ is an amino group, can be converted into a different compound of formula (I) wherein $R_2$ or $R_3$ is a halogen such as chlorine or bromine atom, by reaction with alkyl nitrite and copper(II) chloride or copper(II) bromide in a suitable solvent, such as acetonitrile, tetrahydrofuran and the like, at a temperature ranging from 0° C. to room temperature. Alternatively, the same conversion can be carried out by employing sodium or potassium nitrite and copper(I) chloride or copper(I) bromide in the presence of hydrochloric or hydrobromic acid at a temperature ranging from 0° C. to room temperature. Moreover, a compound of formula (I), as defined above, wherein $R_2$ or $R_3$ is a $NH_2$ group, can be converted into a different compound of formula (I) wherein $R_2$ or $R_3$ is fluorine by reaction with nitrosonium tetrafluoroborate in a solvent such as o-dichlorobenzene at a temperature ranging from 0° C. to reflux. Alternatively, the same conversion can be accomplished with alkyl nitrite and boron trifluoride in a solvent such as o-dichlorobenzene, or with silicon tetrafluoride in dichloromethane or with sodium or potassium nitrite and hydrogen fluoride pyridine complex at a temperature ranging from 0° C. to reflux.

According to conversion E of the process, a compound of formula (I), wherein R and/or $R_1$ are hydrogen atom(s), can be converted into a different compound of formula (I), wherein R and/or $R_1$ are as not $COR_5$ or both hydrogen atoms, by reacting the starting material with the suitable aldehyde or ketone in the presence of a reducing agent, such as sodium triacetoxyborohydride, tetramethylammonium triacetoxyborohydride, sodium cyanoborohydride, sodium borohydride, zinc, optionally in the presence of protic acid, such as hydrochloric, acetic, trifluoroacetic, formic acid and the like, or in the presence of a Lewis acid, such as zinc chloride, zinc bromide, tin(IV) chloride, titanium(IV) chloride, boron trifluoride and the like, in a suitable solvent, such as methanol, ethanol, dichloromethane, acetic acid, N,N-dimethylformamide and the like, at a temperature ranging from 0° C. to room temperature. Alternatively, the conversion can be accomplished by using the suitable R or $R_1$ derivatives such as the corresponding iodide, bromide, chloride, methanesulphonate, trifluoromethanesulphonate and the like, in the presence of a suitable base such as, for instance, sodium, potassium or cesium carbonate, sodium or potassium hydrogencarbonate, triethylamine, diisopropylethylamine, pyridine and the like, at a temperature ranging from 0° C. to reflux.

According to conversion F of the process, a compound of formula (I), as defined above, wherein R and/or $R_1$ are hydrogen atoms, can be converted into a different compound of formula (I), wherein R and/or $R_1$ is $COR_5$, by reaction with $R_5COCl$, wherein $R_5$ is as defined above, in the presence of a suitable base such as triethylamine, diisopropylethylamine, pyridine and the like, in a solvent such as dichloromethane, tetrahydrofuran and the like, at a temperature ranging from 0° C. to reflux. Alternatively, the conversion can be accomplished by reaction with a compound of formula $R_5COOH$, wherein $R_5$ is as defined above, in presence of a suitable coupling agent, such as an alkyl chloroformate, a suitable carbodiimide, such as, for instance, dicyclohexylcarbodiimide, 1-ethyl-3-(3-dimethylaminopropyl)carbodiimide and the like, optionally in the presence of HOBt (1-hydroxybenzotriazole), or other coupling agents, such as, for instance, carbonyldiimidazole, BOP (Benzotriazol-1-yloxy)tris(dimethylamino)phosphonium hexafluorophosphate), TBTU (2-(1H-benzotriazol-1-yl)-1,1,3,3-tetramethyluronium tetrafluoroborate), HATU (O-(7-Azabenzotriazol-1-yl)-N,N,N',N'-tetramethyluronium hexafluorophosphate), and the like in the presence of a base such as triethylamine, diisopropylethylamine, pyridine, 4-N,N-dimethylaminopyridine and the like, sodium or potassium carbonate in a solvent, such as dichloromethane, N,N-dimethylformamide, tetrahydrofuran, acetonitrile and the like, at a temperature ranging from 0° C. to reflux.

According to conversion G of the process, a compound of formula (XIII), as defined above wherein X' is an OH can be converted into a different compound of formula (XIII) wherein X' is a different living group. This transformation can be achieved in the presence of a suitable halogenating system such $I_2/Ph_3P$ or $CBr_4$ with imidazole in a suitable solvent such as, for instance, dichloromethane, N,N-dimethylformamide, tetrahydrofuran, acetonitrile and the like, at a temperature ranging from 0° C. to reflux. All the above processes are analogy processes which can be carried out according to well known methods and under suitable conditions known in the art as reported, for instance, in: Smith, Michael—March's Advanced Organic Chemistry: reactions mechanisms and structure—6th Edition, Michael B. Smith and Jerry March, John Wiley & Sons Inc., New York (NY), 2007.

Any of the intermediates of the above described processes can be converted into a different intermediate by operating in an analogous way as in any conversion reaction here above described.

From all of the above it is clear to the skilled person that any compound of formula (I) bearing a functional group, which can be further elaborated to another functional group, by working according to methods well known in the art, thus leading to other compounds of formula (I), is intended to be comprised within the scope of the present invention. According to any variant of the process for preparing the compounds of formula (I), the starting materials and any other reactants are known or easily prepared according to known methods. Compounds of formula (III), (IV), (VIII), (IX), (XI) and (XII) are commercially available or can be prepared according to known methods.

From all of the above, it is clear to the skilled person that when preparing compounds of formula (I) according to any of the aforementioned process variants, optional functional groups within the starting materials or intermediates thereof that could give rise to unwanted side reactions, need to be properly protected according to conventional techniques. Likewise, the conversion of these latter into the unprotected compounds may be carried out according to known procedures described, for instance, in: Greene, Theodora W. and Wuts, Peter G. M.—Protective Groups in Organic Synthesis, Third Edition, John Wiley & Sons Inc., New York (NY), 1999.

As it will be easily appreciated, if compounds of formula (I), prepared according to the process described above, are obtained as a mixture of isomers, their separation using conventional techniques into the single isomers of formula (I) is within the scope of the present invention.

Conventional techniques for racemate resolution include, for instance, partitioned crystallization of diastereoisomeric salt derivatives or preparative chiral HPLC and the like. General methods for separation of compounds containing one or more asymmetric centers are reported, for instance, in: Jacques, Jean; Collet, André; Wilen, Samuel H.,—Enantiomers, Racemates, and Resolutions, John Wiley & Sons Inc., New York (NY), 1981.

In addition, the compounds of formula (I) of the invention may be also prepared according to combinatorial chemistry techniques widely known in the art, for instance by accomplishing the aforementioned reactions between intermediates in a parallel and/or serial manner and by working under solid-phase-synthesis (SPS) conditions.

As stated above, the probes used in the screening method are the compounds of formula (II) as defined above. Preferably, the present invention provides probes of formula (II) as defined above characterized in that the counterion represented by $X^-$ is a perchlorate, trifluoroacetate and the like, $R_{13}$ is hydrogen atom or methyl, m is 0 or 1; when m is 1, n is preferably 6; more preferably $X^-$ is trifluoroacetate.

Compounds of formula (II), as defined above, are very efficient probes in the binding to the PARP proteins, encompassing both full-length native proteins and fragments thereof.

The polarization signal can be measured, e.g., by a plate reader such as the Saphire2 (Tecan). The displacement ability of the test compound is in correlation with the compound affinity for the NAD pocket of the enzyme. Affinity binding constant (KD) and DC$_{50}$s of the test compound can be determined as explained in the Example section.

The assay of the invention is based on the use as probes of compounds of formula (II) as defined above that provide the fluorescent signal.

Preferred compounds of the formula (II) as defined above of the present invention are:

P1 9-dimethylamino-11,11-dimethyl-1-(3-{methyl-[(6-oxo-5,6-dihydro-phenanthridin-2-ylcarbamoyl)-methyl]-carbamoyl}-propyl)-2,3,4,11-tetrahydro-naphtho[2,3-g]quinolinium trifluoroacetate;

P2 9-dimethylamino-11,11-dimethyl-1-[3-(3-{[(6-oxo-5,6-dihydro-phenanthridin-2-ylcarbamoyl)-methyl]-amino}-propylcarbamoyl)-propyl]-2,3,4,11-tetrahydro-naphtho[2,3-g]quinolinium trifluoroacetate and P3 9-Dimethylamino-11,11-dimethyl-1-[3-(6-{[(6-oxo-5,6-dihydro-phenanthridin-2-ylcarbamoyl)-methyl]-amino}-hexylcarbamoyl)-propyl]-2,3,4,11-tetrahydro-naphtho[2,3-g]quinolinium trifluoroacetate.

The present invention also provides a process for preparing a compound of formula (II), as defined above, which process comprises:

step i) either reacting a compound of formula (XV):

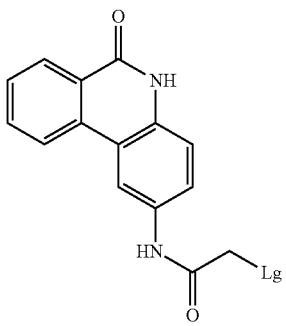

XV wherein Lg is as defined above, with a compound of formula (XVI) $R_{13}$—NH$_2$, wherein $R_{13}$ is as defined above, to give a compound of formula (XVII):

XVII wherein $R_{13}$ and B are as defined above and m is 0;

or step i$_a$) reacting a compound of formula (XV), as defined above, with a compound of formula (XVIa):

XVIa wherein $R_{13}$ and B are as defined above, m is 1 and $R_{14}$ is hydrogen atom, methoxycarbonyl, ethoxycarbonyl, tert-butoxycarbonyl, benzyloxycarbonyl, 9-fluorenylmethoxycarbonyl or the like; and step i$_b$) converting, if necessary, the resultant compound of formula (XVIIa):

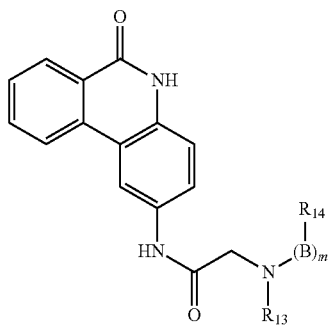

XVIIa wherein $R_{13}$ and B are as defined above, m is 1 and $R_{14}$ is a methoxycarbonyl, ethoxycarbonyl, tert-butoxycarbonyl, benzyloxycarbonyl, 9-fluorenylmethoxycarbonyl group or the like, into a compound of formula (XVII) wherein $R_{14}$ is hydrogen atom;

step ii) coupling the resultant compound of formula (XVII), as defined above, with a compound of formula (XVIII):

XVIII wherein X$^-$ is as defined above, so as to obtain the final compound of formula (II) as defined above; and, if necessary, converting a compound of formula (II) into another compound of formula (II) wherein X$^-$ is different. The starting compound of formula (XV) can be prepared as extensively described, see, for instance WO 2001042219; the compounds of formula (XVIII) are described in Cha, J. H. et al., J. Med. Chem. 2005, 48, 7513-7516 and ATTO 610 fluorescent moiety, activated as its NHS ester, is commercially available (ATTO-TEC GmbH, Siegen, Germany).

Scheme 2 below shows the preparation of compounds of formula (II), wherein $R_{13}$, $R_{14}$, B and m have the meanings defined above.

be removed under acidic conditions, preferably in the presence of an inorganic or organic acid, such as hydrochloric, trifluoroacetic or methanesulphonic acid, in a suitable solvent, such as dichloromethane, dichloroethane, dioxane, a lower alcohol, such as methanol or ethanol, at a temperature ranging from room temperature to reflux. Protective groups, such as benzyloxycarbonyl and the like, can be removed with a suitable reducing agent, such as molecular hydrogen, cyclohexene, cyclohexadiene, formic acid, ammonium formate

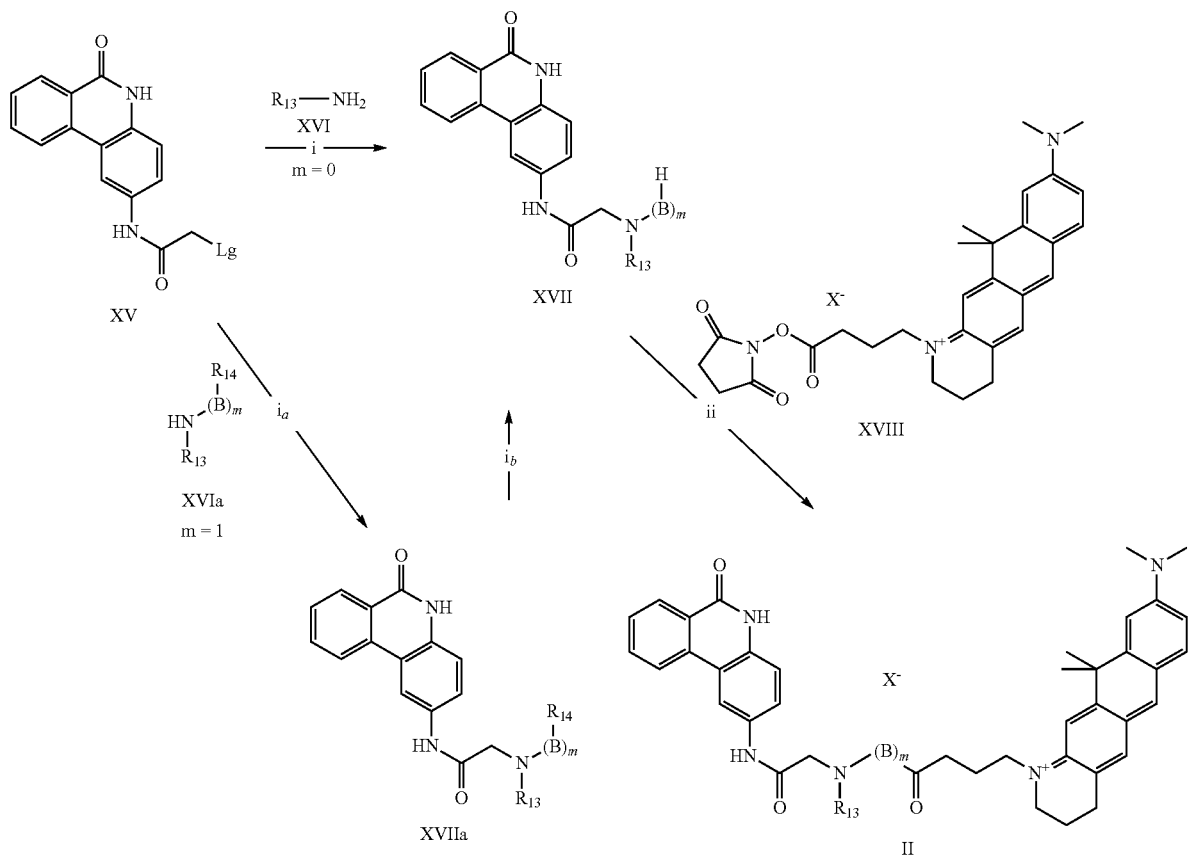

SCHEME 2

According to steps i and $i_a$ of the process, a compound of formula (XV), as defined above, is reacted with a compound of formula (XVI) or (XVIa), as defined above, in the presence of a base, such as, for instance, sodium or potassium hydroxide, sodium, potassium or cesium carbonate, sodium or potassium hydrogencarbonate, triethylamine, diisopropylethylamine, pyridine and the like, in a suitable solvent such as acetonitrile, dioxane, methanol, ethanol or N,N-dimethylformamide, at a temperature ranging from 0° C. to reflux to give, starting from compound (XVI), as defined above, a compound of the formula (XVII), as defined above or, starting from compound (XVIa), as defined above, a compound of formula (XVIIa), as defined above;

According to step $i_b$ of the process, a compound of formula (XVIIa), wherein m=1, $R_{14}$ is a methoxycarbonyl, ethoxycarbonyl, tert-butoxycarbonyl, benzyloxycarbonyl, 9-fluorenylmethoxycarbonyl group or the like, is converted into a compound of formula (XVI), as defined above, by removing the corresponding nitrogen protective group. In particular, protective groups, such as tert-butoxycarbonyl and the like, can and the like, in the presence of a hydrogenation catalyst, such as, for instance, palladium on carbon, palladium hydroxide, palladium black, Ni Raney and the like, in a suitable solvent, such as methanol, ethanol, dioxane and the like, at a temperature ranging from room temperature to reflux.

Protective groups such as methoxycarbonyl, ethoxycarbonyl, 9-fluorenylmethoxycarbonyl and the like could be removed under basic conditions such as, for instance, sodium, potassium or cesium carbonate, sodium, potassium or barium hydroxide, hydrazine, piperidine, morpholine and the like, in a suitable solvent, such as methanol, ethanol, water, N,N-dimethylformamide, N,N-dimethylacetamide and the like, at a temperature ranging from room temperature to reflux.

According to step ii of the process, a compound of formula (XVII), as defined above, is reacted with a compound of formula (XVIII) in the presence of a suitable base, such as triethylamine, diisopropylethylamine, pyridine and the like, in a solvent, such as N,N-dimethylformamide, N,N-dimethylacetamide and the like, at a temperature ranging from 0° C. to room temperature so as to obtain the desired compounds of formula (II).

Pharmacology

Compounds potencies were evaluated by measuring the inhibition of poly (ADP-ribose) (PAR) chains formation as a marker for PARP-1 inhibition.

PARP-1 is a DNA damage-induced polymerase that catalyzes the cleavage of NAD+ into nicotinamide and ADP-ribose and then uses the latter to synthesize branched nucleic-acid like polymers poly(ADP-ribose). In vivo, the most abundant poly (ADP-ribosylated) protein is PARP-1 itself, followed by histones. PARP-1 is responsible for 90% of this DNA damage-induced activity while the remaining 10% is due to PARP-2.

The short forms and abbreviations used herein have the following meaning:

PAR (poly (ADP-ribose))
MEM (Minimal Essential Medium)
FCS (Fetal Calf Serum)
FBS (Fetal Bovine Serum)
PBS (Phosphate Buffered Saline)
LC-MS (Liquid Chromatography-Mass Spectrometry)
HPLC (High Performance Liquid Chromatography)
DC50 (The half maximal Displacement Concentration)
IC50 (The half maximal Inhibitory Concentration)
STD (Standard Deviation)
Cellular Assay Cellular activity of PARP-1 inhibitors was assessed by measuring the inhibition of the hydrogen peroxide induced PAR formation in HeLa cells (ECACC). Cellular PAR levels were measured by immunocytochemistry and quantified using an ArrayScan vTi instrument (Cellomics Thermo Scientific).

Studies were performed as follows: 6000 cells/well were seeded in 96 well plates (Perkin Elmer) in MEM/10% FCS and incubated for 24 hours at 37° C., 5% carbon dioxide. Test compounds were then added at the required concentration for 30'. DNA damage was then induced adding hydrogen peroxide at the concentration of 0.1 mM for 15 min. Concentration curves were prepared in MEM/10% FCS from compound stocks in DMSO and final DMSO concentration was 0.002% (v/v). Duplicate wells for each concentration point were prepared with a typical highest compound concentration of 20 µM and serial dilution 1:3. Plates were dried and fixed adding cold methanol/acetone (70:30) solution for 15 min at room temperature, fixing solution was aspired and wells were air dried for 5 min and then dehydrated in PBS. Non-specific binding sites were blocked by incubating wells for 30 min in PBS containing 5% (w/v) FBS 0.05% tween20. Wells were then incubated for 1 hour at room temperature in PBS containing anti PAR mouse monoclonal antibody (Anti-PAR, Mouse mAb 10H, Tulip Cat No 1020) diluted 1:200 in blocking solution. After 3 washes in PBS, wells were incubated in PBS (w/v) 5% FBS 0.05% Tween20 containing 2 µg/ml Cy2-conjugated Goat anti mouse secondary antibody (Amersham Pharmacia Biotech cat. No PA 42002) (Absorption maximum 489 nm fluorescence maximum 506 nm) and 1 µg/ml DAPI (Absorption maximum 359 nm fluorescence maximum 461 nm) (4',6-Diamidino-2-phenyindole dilactate) (Sigma cat. No D9564), a high sensitivity dye for nucleic acid staining. After washing further 3 times in PBS, cellular PAR immunoreactivity was assessed using the ArrayScan vTi instrument, with a Zeiss 10×0.5 N.A. objective, and applying the Cytotoxicity.V3 algorithm (Cellomics/Thermo Fisher) with a XF100 filter. At least 10 fields, corresponding to at least 900 cells, were read for each well. $IC_{50}$ values represent the compound concentration at which cellular PAR signal is diminished by 50% compared with untreated controls.

The following formula is used:

$IC_{50}$=Bottom+(Top−Bottom)/(1+10^((Log EC50−X))); X is the logarithm of concentration. $IC_{50}$ is the response; $IC_{50}$ starts at Bottom and goes to Top with a sigmoid shape.

Given the above assays, the compounds of formula (I) resulted to inhibit PAR formation with $IC_{50}$ values lower than 10 µM (table 3).

Biochemical Assay

Affinity of the tested compounds and their selectivity with respect to the different PARP isoforms of interest was quantified in a displacement assay.

The assay is based on the use of a probe of formula (II) that binds to the NAD binding pocket and takes advantage of the significant change in the polarization signal observed upon binding of the probe to PARP-1, -2 and -3.

The probe (II) was tested for its ability to bind FL PARP-1, -2 and -3 in a titration experiment. The assay performances were then evaluated (Z' factor) as well as the displacement of the probe by its scaffold and known commercially available PARP inhibitors. In all of the experiments, the polarization signal was measured using a Saphire2 plate reader (Tecan). Data analysis was performed using Dynafit software. In particular, titration data were fitted to the following equilibria: Enzyme+probe <==>Complex Enzyme-probe, while displacement data were fitted to the following equilibria: Enzyme+probe <==>Complex Enzyme-probe, Enzyme+Compound <==>Complex Enzyme-Compound, whereby binding of probe and compound on the enzyme are mutually exclusive (pure competitive mechanism). Displacement data were also fitted using Excel spreadsheet (Microsoft Inc. Seattle, USA) to a four parameter logistic model (4PL), or Hill-Slope model to calculate $DC_{50}$s where the $DC_{50}$ value represents the compound concentration at which the polarization signal is diminished by 50% compared to untreated controls.

The titration experiment was performed as follows: 50 nM probe (compound P1), FL PARP-1, 2 and 3 at concentrations from 5 µM to 0, with dilution steps 1:1.5 in 50 mM TrisHCl, pH 7.8, 150 mM NaCl, 10 mM $MgCl_2$, 0.001% Triton X100, 1% DMSO (buffer 1). A similar procedure was followed for compound P3 titration.

The obtained results (shown in Table 1 below) indicated that the probe (compound P1) is capable to bind all of the tested isoforms of PARP. For compound P3 only PARP-1 KD is reported. The Z' factor (Z'=1−(3*(SDprobe+protein+SDprobe)/(Meanprobe+protein−Meanprobe))) was determined as follows: 50 nM probe (compound P1), 250 nM of PARP-1 and 2, 200 nM of PARP-3. PARP-1 concentration was equal to 100 nM when compound P3 was used as probe. In all cases, the Z's were higher than 0.7 indicating that the assays were robust (table 1).

TABLE 1

|  | KD (µM) | STD (µM) | Z' |
| --- | --- | --- | --- |
| PARP-1 FL (compound P3) | 0.4 | 0.07 | 0.75 |
| PARP-1 FL (compound P1) | 1.04 | 0.14 | 0.73 |
| PARP-2 FL (compound P1) | 1.05 | 0.2 | 0.78 |
| PARP-3 FL (compound P1) | 0.18 | 0.016 | 0.9 |

The assay was validated using 3-aminobenzamide (3-AB) and PJ-34 in a displacement assay performed as follows: serial dilutions of test compounds were first prepared in 100% DMSO and further diluted in assay buffer 1 in order to have a 1% final DMSO concentration. 3-AB were tested at 100 µM as highest concentration, while 10 µM was PJ-34 highest concentration. The enzymes were present at a final concentration of 250 nM for PARP-1 (100 nM when compound P3 was used as probe) and PARP-2, while 200 nM was used for PARP-3. Probe (compound P1 or compound P3) final concentration was 50 nM. The mixture of enzyme and probe (compound P1 or compound P3) was added to the previously diluted compounds. Results (Table 2) indicated that the probe (compound P1 or compound P3) could be fully displaced by 3-AB and PJ-34 from all of the tested PARP isoforms, indicating that the probes (compound P1 or compound P3) binding is specific. In agreement, affinity binding constants (KD) were determined by fitting with a pure competitive mechanism. KD values are the average of three independent experiments.

3-AB, as expected, was not selective among the PARP isoforms and showed a lower affinity with respect to PJ-34.

TABLE 2

|  | PJ34 KD ($\mu$M) | STD ($\mu$M) | 3-AB KD ($\mu$M) | STD ($\mu$M) |
|---|---|---|---|---|
| PARP-1 FL (compound P3) | <0.01* |  | 5.56 | 0.55 |
| PARP-1 FL (compound P1) | <0.03* |  | 6.68 | 1.2 |
| PARP-2 FL (compound P1) | <0.03* |  | 7.4 | 1.04 |
| PARP-3 FL (compound P1) | 0.15 | 0.026 | 17.7 | 4.25 |

*assay sensitivity limits based on a fitting error <50%

Taken together, these results show that the displacement assay is specific. Moreover it allows quantitative potency evaluation of standard PARP inhibitors tested, and therefore selectivity evaluation among assays.

The same assay, by using either compound P1 or P3, was used to evaluate some representative compounds of formula (I) as reported in table 3.

TABLE 3

| Compounds | PARP-1 (DC$_{50}$ $\mu$M) | PARP-1 (Kd $\mu$M) | PARP-2 (DC$_{50}$ $\mu$M) | PARP-2 (Kd $\mu$M) | PARP-3 (DC$_{50}$ $\mu$M) | PAR assay (IC$_{50}$ $\mu$M) |
|---|---|---|---|---|---|---|
| 1 | <0.25 | <0.03 | 2.89 | 3.07 |  | 0.79 |
| 2 | 0.32 | 0.20 | 337.96 | 6.28 |  | 6.72 |
| 3 | <0.25 | <0.03 | 4.1 | 3.92 |  | 3.26 |
| 4 | 0.31 | 0.19 | 0.91 | 0.95 |  |  |
| 5 | <0.25 | <0.03 | 4.34 | 4.59 |  | 1.44 |
| 6 | <0.25 | <0.03 | >10 | >10 |  | 0.86 |
| 7 | <0.25 | <0.03 | >10 | >10 |  |  |
| 8 | 0.82 |  | 4.29 |  |  |  |
| 9 | 0.37 |  | 0.86 |  |  |  |
| 10 | 0.35 | 0.05 | 147.78 | 4.39 |  | 0.33 |
| 11 | <0.25 | <0.03 | 668.20 | 625.78 | 0.35 | 0.18 |
| 12 | <0.25 | 0.05 | 2.91 | 1.65 |  | 0.42 |
| 14 | <0.25 | <0.03 | 4.29 | 6.13 |  | 4.20 |
| 16 | <0.25 | <0.03 | 204.31 | 2.44 |  | 0.48 |
| 17 | <0.25 | <0.03 | 3.28 | 1.01 |  | 0.34 |
| 18 | <0.25 | <0.03 | 339.05 | 8.65 |  | 0.85 |
| 19 | <0.25 | <0.03 | 337.79 | 7.29 |  |  |
| 20 | <0.25 | 0.05 | 5.52 | 5.35 |  | 6.50 |
| 21 | <0.25 | 0.04 | 1.58 | 1.36 |  | 8.30 |
| 22 | <0.25 | <0.03 | 4.08 | 1.34 |  | 9.50 |
| 23 | <0.25 | <0.03 | 336.07 | 501.65 | 0.48 | 0.17 |
| 24 | 0.32 | <0.03 | 750.05 | 501.58 | 0.37 | 0.06 |
| 25 | <0.25 | <0.01* | 2.29 | 0.61 | 0.21 | 0.06 |
| 26 | <0.25 | <0.01* | 0.68 | 0.33 | 0.35 | 0.23 |
| 27 | <0.25 | <0.03 | 0.77 | 0.33 | 0.55 | 0.25 |
| 28 | <0.25 | <0.03 | 1.10 |  | 0.47 | 0.40 |
| 29 | <0.25 | <0.03 | 0.54 |  | 0.2 |  |
| 32 | <0.25 | <0.03 | 0.79 | 0.45 | 0.28 | 0.20 |
| 33 | <0.25 | <0.03 | 0.58 | 0.25 | 0.34 | 0.41 |
| 37 | <0.25 |  | 337.93 |  |  | 0.62 |

TABLE 3-continued

| Compounds | PARP-1 (DC$_{50}$ $\mu$M) | PARP-1 (Kd $\mu$M) | PARP-2 (DC$_{50}$ $\mu$M) | PARP-2 (Kd $\mu$M) | PARP-3 (DC$_{50}$ $\mu$M) | PAR assay (IC$_{50}$ $\mu$M) |
|---|---|---|---|---|---|---|
| 38 | <0.25 |  | 3.78 |  |  | 0.30 |
| 39 | <0.25 | <0.01* | 3.32 | 4.38 | 0.28 | 0.06 |
| 43 | <0.25 | 0.04 | 4.21 | 2.02 | 2.52 | 0.09 |
| 44 | <0.25 | <0.03 | 0.70 | 0.40 | 1.23 | 0.13 |
| 45 | <0.25 | <0.03 | 0.42 | 0.12 | 0.25 | 0.28 |
| 46 | <0.25 | <0.01* | 5.99 | 3.61 | 0.37 | 0.06 |
| 47 | <0.25 | <0.03 | 0.51 |  | 0.22 | 0.10 |
| 48 | <0.25 | <0.01* | 1.16 | 0.51 | 0.33 | 0.11 |
| 49 | <0.25 | <0.01* | 0.97 |  | 0.2 | 0.09 |
| 50 | <0.25 | <0.03 | 3.30 |  | 0.33 | 0.08 |
| 84 | <0.25 |  | 3.86 |  | 1.11 | 0.57 |
| 85 | 0.38 |  | 4.35 |  | 0.54 |  |
| 86 | <0.25 |  | 4.72 |  | 0.33 | 0.54 |
| 87 | <0.25 |  | >10 |  | 1.11 | 0.40 |
| 88 | 1.59 |  | 5.85 |  | >10 | 3.44 |
| 89 | 0.4 |  | >10 |  | 6.45 | 7.55 |

*Assay performed with compound P3 as the probe. In all other cases compound P1 was used as the probe. From the above, it is clear to the person skilled in the art that compounds of formula (I) are potent and selective PARP-1 inhibitors both in biochemical and cellular assays.

Pharmacokinetics

The pharmacokinetic profile and the oral bioavailability of the compounds have been investigated in the mouse (Balb, Nu/Nu, Harlan, Italy) in ad hoc pharmacokinetic studies. The compounds were formulated in 10% tween 80/dextrose for intravenous bolus administration while oral administrations were performed using the compounds formulated in 0.5% methylcellulose. A single administration at the dose of 10 mg/kg was given and three male animals for each route were used. All blood samples were taken from saphenous vein at 5 min, 30 min, 1 h, 6 h, 24 h after intravenous administration and 15 min, 30 min, 1 h, 6 h, 24 h after oral administration. Plasma samples were prepared by plasma proteins precipitation adding 200 l of methanol to 10 l of plasma in a 96 well plate. After capping and vortex mixing, the plate was centrifuged for 15 min at 3700 rpm at 6° C. The supernatant was considered as final extract and injected onto the LC-MS-MS system (HPLC system: Hewlett Packard 1100 series using Atlantis HILIC Silica 50*2.1 mm 5.0 M analytical column; MS instrument: Perkin Elmer SCIEX API 2000 and ionization performed with Turbo Ion Spray in positive ion mode). Lower limit of quantification is 5.0 ng/ml, upper limit of quantification is 10000 ng/ml. Analysis was performed using the Watson package (version 6.4.0.04) and Excel spreadsheet (Microsoft Inc. Seattle, USA). Non-compartmental method (linear trapezoidal rule and linear regression analysis of natural log-transformed plasma concentrations vs. time data) was used. After intravenous dosing, $C_0$ was set equal to $C_{0.083}$. Absolute bioavailability (F) was calculated from the ratio of average oral to IV (intravenous) dose-normalized plasma AUC (area under curve) values.

The abbreviations used herein have the following meaning:

AUC (area under the plasma concentration vs. time curve up to the last detectable concentration)

Cl (plasma clearance)

Cmax (maximum plasma concentration)

T½ (terminal half life)

Vdss (volume of distribution at steady state)

Some representative compounds of formula (I) were evaluated for their pharmacokinetic parameters as reported in table 4 as mean value.

TABLE 4

| Compounds | CL(IV bolus) ml/min/kg | Vdss (IV bolus) L/Kg | AUC (oral) M. hours | C-max(oral) M | T1/2 (oral) hours | F on AUC % |
|---|---|---|---|---|---|---|
| 33 | 176 | 2.9 | 0.64 | 0.37 | 1.11 | 24 |
| 12 | 177 | 3.3 | 0.52 | 0.49 | 1.19 | 17 |
| 24 | 41.1 | 3.0 | 6.97 | 2.88 | 2.71 | 50 |
| 48 | 59.9 | 4.1 | 2.39 | 1.93 | 1.11 | 27 |
| 25 | 42.2 | 2.3 | 8.32 | 2.91 | 2.17 | 71 |
| 39 | 37.9 | 1.7 | 11.0 | 3.78 | 1.06 | 72 |
| 11 | 120 | 2.6 | 2.94 | 1.84 | 1.01 | 64 |

From the above, it is clear to the person skilled in the art that compounds of formula (I) possess good to excellent pharmacokinetics profiles and oral bioavailability.

In Vivo Efficacy Studies

Balb, athymic Nu/Nu male mice, from Harlan (Italy), were maintained in agreement with the European Communities Council Directive no. 86/609/EEC concerning the protection of animals used for experimental or other scientific purposes, in cages with paper filter cover, food and bedding sterilized and acidified water. Fragments of Capan-1 human pancreatic cancer tumors were implanted subcutaneously. Mice bearing a palpable tumor (100-200 mm$^3$) were selected and randomized into control and treated groups. Each group included seven animals. The treatment started one day after randomization. Compound of formula (I) was administered by oral route as a methocel suspension at the doses of 100 mg/kg daily or twice a day for the indicated times. Tumor dimension was measured regularly by calipers during the experiments and tumor mass was calculated as described in Simeoni M. et al., Cancer Res 64, 1094-1101 (2004). The tumor growth inhibition (TGI, %) was calculated according to the equation:

% TGI=100−(mean tumor weight of treated group/mean tumor weight of control group)*100.

Some representative compounds of formula (I), compound (25), compound (39) and compound (II), were evaluated for their anti-tumor activity as single agent on Capan-1 BRCA-2 mutated mouse model. Toxicity was evaluated on the basis of body weight reduction and animal survival rate. The results are reported in table 5.

TABLE 5

| Compounds | Dose | Schedule | Max TGI (%) | Toxicity |
|---|---|---|---|---|
| 25 | 100 mg/kg | 1-20 once a day | 18% | 0/7 |
| 39 | 100 mg/kg | 1-10 twice a day | 48% | 0/7 |
| 11 | 150 mg/kg | 1-14 twice a day | 31% | 0/7 |

A representative compound of formula (I), compound (39), was evaluated for its anti-tumor activity on Capan-1 BRCA-2 mutated mouse model in combination with temozolomide. Compound (39) was administered by oral route at the dose of 100 mg/kg twice a day for ten consecutive days (days 1 to 10). Temozolomide was administered by oral route at the dose of 50 mg/kg on days 3, 4, 5, 6 and 7. Tumor growth and body weight were measured every 3 days. Tumor growth was assessed by caliper. The two diameters were recorded and the tumor weight was calculated according to the following formula: length (mm)×width$^2$/2. The effect of the antitumor treatment was evaluated as the delay in the onset of an exponential growth of the tumor (see for references Anticancer drugs 7:437-60, 1996). This delay (T-C value) was defined as the difference of time (in days) required for the treatment group (T) and the control group (C) tumors to reach a predetermined size (1 g). Toxicity was evaluated on the basis of body weight reduction and animal survival rate. The results are reported in table 6.

TABLE 6

| Treatment | T-C (days) | Toxicity |
|---|---|---|
| Compound (39) 100 mg/kg* | 3 | 0/7 |
| temozolomide 50 mg/kg** | 3 | 0/7 |
| temozolomide 50 mg/kg+ Compound (39) 100 mg/kg*** | 21 | 0/7 |

*Oral treatments made on day 1 to 10 on days 1 to 10 twice a day
**Treatments made by oral route once a day at days 3, 4, 5, 6 and 7
***Compound (39) treatments days 1 to 10, temozolomide treatments, days 3, 4, 5, 6, 7.

The T-C observed when compound (39) was combined with temozolomide was superior to the expected by the simple addition of T-C obtained by the single treatments indicating strong synergism.

From the above, it is clear to the person skilled in the art that compounds of formula (I) possess good tumor growth inhibition activities as single agent and synergic tumor growth inhibition activities in combination with cytotoxic agents.

EXPERIMENTAL SECTION

For a reference to any specific compound of formula (I) of the invention, optionally in the form of a pharmaceutically acceptable salt, see the experimental section and claims. Referring to the examples that follow, compounds of the present invention were synthesized using the methods described herein, or other methods, which are well known in the art.

The short forms and abbreviations used herein have the following meaning:
min (minutes)
mmol (millimoles)
DMSO (dimethylsulphoxide)
ESI (electrospray ionization)

With the aim to better illustrate the present invention, without posing any limitation to it, the following examples are now given.

As used herein the symbols and conventions used in the processes, schemes and examples are consistent with those used in the contemporary scientific literature, for example, the Journal of the American Chemical Society or the Journal of Biological Chemistry.

Unless otherwise noted, all materials were obtained from commercial suppliers, of the best grade and used without further purification. Anhydrous solvent such as N,N-dimethylformamide, tetrahydrofuran, dichloromethane and toluene were obtained from the Aldrich Chemical Company. All reactions involving air- or moisture-sensitive compounds were performed under nitrogen or argon atmosphere.

General Purification and Analytical Methods

Flash Chromatography was performed on silica gel (Merck grade 9395, 60A). HPLC was performed on Waters X Terra RP 18 (4.6×50 mm, 3.5 µm) column using a Waters 2790 HPLC system equipped with a 996 Waters PDA detector and Micromass mod. ZQ single quadrupole mass spectrometer, equipped with an electrospray (ESI) ion source. Mobile phase A was ammonium acetate 5 mM buffer (pH 5.2 with acetic acid-acetonitrile 95:5), and Mobile phase B was water-acetonitrile (5:95). Gradient from 10 to 90% B in 8 min, hold 90% B 2 min. UV detection at 220 nm and 254 nm. Flow rate 1 mL/min. Injection volume 10 µL. Full scan, mass range from 100 to 800 amu. Capillary voltage was 2.5 KV; source temperature was 120° C.; cone was 10 V. Masses are given as m/z ratio.

When necessary, compounds were purified by preparative HPLC on a Waters Symmetry C18 (19×50 mm, 5 m) column or on a Waters X Terra RP 18 (30×150 mm, 5 μm) column using a Waters preparative HPLC 600 equipped with a 996 Waters PDA detector and a Micromass mod. ZMD single quadrupole mass spectrometer, electron spray ionization, positive mode. Mobile phase A was water-0.01% trifluoroacetic acid, and mobile phase B was acetonitrile. Gradient from 10 to 90% B in 8 min, hold 90% B 2 min. Flow rate 20 mL/min. In alternative, mobile phase A was water-0.1% $NH_3$ and mobile phase B was acetonitrile. Gradient from 10 to 100% B in 8 min, hold 100% B 2 min. Flow rate 20 mL/min.

$^1$H NMR spectrometry was performed on a Mercury VX 400 operating at 400.45 MHz equipped with a 5 mm double resonance probe [1H (15N-31P) ID_PFG Varian].

Example 1

Step 1

2-[2-(3-Methoxy-phenyl)-2-oxo-ethoxy]-benzamide

To a suspension of 5 g (36.5 mmol) of salicylamide in 60 mL of N,N-dimethylformamide, 8.36 g (36.5 mmol) of 2-bromo-1-(3-methoxy-phenyl)-ethanone and 7.57 g (54.7 mmol) of potassium carbonate were added. The mixture was stirred at room temperature overnight. Water was added under stirring and the precipitate was filtered, washed with water and dried in vacuo to yield 9 g of the title compound (90%).

$^1$H NMR (DMSO-$d_6$) δ (ppm): 8.41 (br. s., 1H), 7.99 (dd, J=7.8, 1.8 Hz, 1H), 7.69 (br. s., 1H), 7.67 (ddd, J=7.7, 1.5, 0.9 Hz, 1H), 7.57 (dd, J=2.5, 1.5 Hz, 1H), 7.52 (t, J=8.0 Hz, 1H), 7.51 (ddd, J=8.4, 7.3, 2.0 Hz, 1H), 7.29 (ddd, J=8.3, 2.6, 0.9 Hz, 1H), 7.29 (dd, J=8.3, 0.9 Hz, 1H), 7.09 (ddd, J=7.8, 7.3, 1.0 Hz, 1H), 5.77 (s, 2H), 3.85 (s, 3H).

According to this same methodology, but employing suitably substituted starting materials, the following compounds were prepared:

2-(2-Oxo-2-phenyl-ethoxy)-benzamide $^1$H NMR (DMSO-$d_6$) δ (ppm): 8.41 (br. s., 1H), 8.08 (dd, J=8.4, 1.2 Hz, 2H), 7.99 (dd, J=7.7, 1.8 Hz, 1H), 7.72 (t, J=7.4 Hz, 1H), 7.69 (br. s., 1H), 7.60 (t, J=7.7 Hz, 2H), 7.51 (ddd, J=8.2, 7.4, 2.0 Hz, 1H), 7.28 (d, J=8.2 Hz, 1H), 7.09 (t, J=7.5 Hz, 1H), 5.78 (s, 2H).

5-Acetyl-2-(2-oxo-2-phenyl-ethoxy)-benzamide $^1$H NMR (DMSO-$d_6$) δ (ppm): 8.56 (d, J=2.4 Hz, 1H), 8.35 (br. s., 1H), 8.08 (dd, J=8.2, 1.5 Hz, 2H), 8.09 (dd, J=8.8, 2.4 Hz, 1H), 7.86 (br. s., 1H), 7.73 (t, J=7.4 Hz, 1H), 7.61 (t, J=7.6 Hz, 2H), 7.40 (d, J=8.8 Hz, 1H), 5.90 (s, 2H), 2.57 (s, 3H).

2-[2-(4-Methoxy-phenyl)-2-oxo-ethoxy]-benzamide $^1$H NMR (DMSO-$d_6$) δ (ppm): 3.88 (s, 3H) 5.71 (s, 2H) 7.06-7.09 (m, 1H) 7.09-7.14 (m, 2H) 7.24-7.29 (m, 1H) 7.47-7.53 (m, 1H) 7.66 (d, J=1.46 Hz, 1H) 7.98 (dd, J=7.75, 1.77 Hz, 1H) 8.02-8.10 (m, 2H) 8.46 (br. s., 1H).

5-Chloro-2-(2-oxo-2-phenyl-ethoxy)-benzamide $^1$H NMR (DMSO-$d_6$) δ (ppm): 8.39 (br. s., 1H), 8.07 (dd, J=7.8, 1.2 Hz, 2H), 7.91 (d, J=2.8 Hz, 1H), 7.87 (br. s., 1H), 7.72 (t, J=7.4 Hz, 1H), 7.60 (t, J=8.0 Hz, 2H), 7.57 (dd, J=8.8, 2.9 Hz, 1H), 7.34 (d, J=8.9 Hz, 1H), 5.80 (s, 2H).

5-Fluoro-2-(2-oxo-2-phenyl-ethoxy)-benzamide $^1$H NMR (DMSO-$d_6$) δ (ppm): 8.47 (br. s., 1H), 8.07 (dd, J=8.4, 1.3 Hz, 2H), 7.87 (br. s., 1H), 7.72 (t, J=7.6 Hz, 1H), 7.69 (dd, J=9.6, 3.2 Hz, 1H), 7.60 (t, J=7.7 Hz, 2H), 7.39 (ddd, J=9.0, 7.6, 3.3 Hz, 1H), 7.34 (dd, J=9.1, 4.5 Hz, 1H), 5.78 (s, 2H).

4-Nitro-2-(2-oxo-2-phenyl-ethoxy)-benzamide $^1$H NMR (DMSO-$d_6$) δ (ppm): 8.42 (br. s., 1H), 8.15 (d, J=8.7 Hz, 1H), 8.13 (d, J=2.1 Hz, 1H), 8.12 (dd, J=7.7, 1.3 Hz, 2H), 8.02 (br. s., 1H), 7.94 (dd, J=8.5, 2.1 Hz, 1H), 7.75 (tt, J=7.4, 1.3 Hz, 1H), 7.62 (t, J=7.7 Hz, 2H), 5.97 (s, 2H).

5-Nitro-2-(2-oxo-2-phenyl-ethoxy)-benzamide $^1$H NMR (DMSO-$d_6$) δ (ppm): 8.76 (d, J=3.0 Hz, 1H), 8.38 (dd, J=9.1, 3.0 Hz, 1H), 8.36 (br. s., 1H), 8.08 (dd, J=8.3, 1.1 Hz, 2H), 8.05 (br. s., 1H), 7.74 (tt, J=7.4, 1.3 Hz, 1H), 7.61 (t, J=7.7 Hz, 2H), 7.52 (d, J=9.3 Hz, 1H), 5.97 (s, 2H).

3-Methyl-2-(2-oxo-2-phenyl-ethoxy)-benzamide $^1$H NMR (DMSO-$d_6$) δ (ppm): 7.96 (dd, J=8.4, 1.2 Hz, 2H), 7.93 (br. s., 1H), 7.68 (tt, J=7.3, 1.3 Hz, 1H), 7.55 (t, J=8.0 Hz, 2H), 7.51 (ddd, J=7.7, 1.7, 0.4 Hz, 1H), 7.48 (br. s., 1H), 7.35 (ddd, J=7.5, 1.7, 0.7 Hz, 1H), 7.13 (t, J=7.6 Hz, 1H), 5.42 (s, 2H), 2.31 (s, 3H).

2-[2-(3-Chloro-phenyl)-2-oxo-ethoxy]-benzamide $^1$H NMR (DMSO-$d_6$) δ (ppm): 8.35 (br. s., 1H), 8.13 (t, J=1.8 Hz, 1H), 8.02 (ddd, J=7.7, 1.5, 1.0 Hz, 1H), 7.98 (dd, J=7.8, 1.8 Hz, 1H), 7.79 (ddd, J=8.1, 2.2, 1.0 Hz, 1H), 7.70 (br. s., 1H), 7.63 (t, J=7.9 Hz, 1H), 7.51 (ddd, J=8.4, 7.3, 2.0 Hz, 1H), 7.31 (dd, J=8.4, 0.7 Hz, 1H), 7.09 (ddd, J=7.8, 7.3, 1.0 Hz, 1H), 5.78 (s, 2H).

5-Fluoro-2-[2-(3-methoxy-phenyl)-2-oxo-ethoxy]-benzamide $^1$H NMR (DMSO-$d_6$) δ (ppm): 8.47 (br. s., 1H), 7.87 (br. s., 1H), 7.69 (dd, J=9.5, 3.1 Hz, 1H), 7.66 (ddd, J=7.7, 1.6, 1.0 Hz, 1H), 7.56 (dd, J=2.4, 1.6 Hz, 1H), 7.51 (t, J=7.9 Hz, 1H), 7.39 (ddd, J=9.0, 7.6, 3.2 Hz, 1H), 7.34 (dd, J=9.1, 4.5 Hz, 1H), 7.29 (ddd, J=8.3, 2.7, 0.8 Hz, 1H), 5.76 (s, 2H), 3.85 (s, 3H).

5-Fluoro-2-[2-(4-methoxy-phenyl)-2-oxo-ethoxy]-benzamide $^1$H NMR (DMSO-$d_6$) δ (ppm): 8.53 (br. s., 1H), 8.04 (d, J=9.0 Hz, 2H), 7.85 (br. s., 1H), 7.68 (dd, J=9.6, 3.2 Hz, 1H), 7.38 (ddd, J=9.1, 7.6, 3.3 Hz, 1H), 7.32 (dd, J=9.1, 4.4 Hz, 1H), 7.11 (d, J=8.9 Hz, 2H), 5.71 (s, 2H), 3.87 (s, 3H).

2-[2-(3-Chloro-phenyl)-2-oxo-ethoxy]-5-fluoro-benzamide $^1$H NMR (DMSO-$d_6$) δ (ppm): 8.41 (br. s., 1H), 8.12 (t, J=1.8 Hz, 1H), 8.01 (dt, J=8.0, 1.2 Hz, 1H), 7.88 (br. s., 1H), 7.79 (ddd, J=8.0, 2.2, 1.0 Hz, 1H), 7.69 (ddd, J=9.6, 3.0, 0.5

Hz, 1H), 7.63 (t, J=7.9 Hz, 1H), 7.39 (ddd, J=9.1, 7.4, 3.2 Hz, 1H), 7.36 (ddd, J=9.1, 4.6, 0.5 Hz, 1H), 5.77 (s, 2H).

2-(2-Oxo-2-thiophen-3-yl-ethoxy)-benzamide $^1$H NMR (DMSO-d$_6$) δ (ppm): 1.31-1.40 (m, 2H) 1.40-1.52 (m, 4H) 1.67 (quin, J=6.59 Hz, 2H) 2.24 (br. s., 6H) 3.51 (t, J=6.23 Hz, 2H) 6.85 (d, J=8.79 Hz, 2H) 7.51 (ddd, J=8.00, 7.08, 1.28 Hz, 3H) 7.51 (d, J=8.67 Hz, 2H) 7.77 (ddd, J=8.18, 7.02, 1.28 Hz, 1H) 7.86 (d, J=7.95 Hz, 1H) 8.20 (ddd, J=7.93, 1.10, 0.49 Hz, 1H) 9.75 (s, 1H) 11.05 (s, 1H).

Step 2

3-(3-Methoxy-phenyl)-4H-benzo[f][1,4]oxazepin-5-one

A well stirred suspension of 9 g (31.5 mmol) of 2-[2-(3-Methoxy-phenyl)-2-oxo-ethoxy]-benzamide and 0.3 g (1.58 mmol) of p-toluensulphonic acid in toluene (0.3 L) was refluxed with a Dean-Stark apparatus for 2 hours. After concentration of the solvent under reduced pressure, the residue was treated with ethyl acetate and diethyl ether and the resulting solid was filtered, washed with a mixture of the aforementioned solvents, dried in vacuo, affording 7.55 g of the title compound (83%).

$^1$H NMR (DMSO-d$_6$) δ (ppm): 9.76 (s, 1H), 7.78 (dd, J=7.8, 1.6 Hz, 1H), 7.57 (ddd, J=8.1, 7.3, 1.8 Hz, 1H), 7.30 (t, J=8.0 Hz, 1H), 7.29 (td, J=7.5, 1.2 Hz, 1H), 7.14 (dd, J=8.1, 0.8 Hz, 1H), 7.05 (ddd, J=7.7, 1.6, 0.9 Hz, 1H), 7.01 (dd, J=2.3, 1.8 Hz, 1H), 6.94 (ddd, J=8.3, 2.5, 0.8 Hz, 1H), 6.91 (d, J=0.4 Hz, 1H), 3.78 (s, 3H).

According to this same methodology, but employing suitably substituted starting materials, the following compounds were prepared:

3-Phenyl-4H-benzo[f][1,4]oxazepin-5-one $^1$H NMR (DMSO-d$_6$) δ (ppm): 9.77 (s, 1H), 7.78 (dd, J=7.7, 1.6 Hz, 1H), 7.57 (ddd, J=8.2, 7.4, 1.8 Hz, 1H), 7.36-7.50 (m, 5H), 7.29 (td, J=7.6, 0.9 Hz, 1H), 7.14 (dd, J=8.2, 0.7 Hz, 1H), 6.87 (s, 1H).

7-Acetyl-3-phenyl-4H-benzo[f][1,4]oxazepin-5-one $^1$H NMR (DMSO-d$_6$) δ (ppm): 9.97 (s, 1H), 8.36 (d, J=2.2 Hz, 1H), 8.13 (dd, J=8.5, 2.4 Hz, 1H), 7.38-7.52 (m, 5H), 7.28 (d, J=8.5 Hz, 1H), 6.90 (s, 1H), 2.61 (s, 3H).

3-(4-Methoxy-phenyl)-4H-benzo[f][1,4]oxazepin-5-one $^1$H NMR (DMSO-d$_6$) δ (ppm): 3.76 (s, 3H) 6.77 (s, 1H) 6.94 (d, J=8.91 Hz, 3H) 7.13 (dd, J=8.06, 0.73 Hz, 1H) 7.28 (td, J=7.54, 1.04 Hz, 1H) 7.39 (d, J=8.91 Hz, 2H) 7.56 (ddd, J=8.06, 7.32, 1.83 Hz, 1H) 7.77 (dd, J=7.81, 1.71 Hz, 1H) 9.72 (s, 1H).

7-Chloro-3-phenyl-4H-benzo[f][1,4]oxazepin-5-one $^1$H NMR (DMSO-d$_6$) δ (ppm): 9.95 (s, 1H), 7.75 (d, J=2.7 Hz, 1H), 7.63 (dd, J=8.7, 2.8 Hz, 1H), 7.37-7.52 (m, 5H), 7.20 (d, J=8.7 Hz, 1H), 6.90 (s, 1H).

7-Fluoro-3-phenyl-4H-benzo[f][1,4]oxazepin-5-one $^1$H NMR (DMSO-d$_6$) δ (ppm): 9.93 (s, 1H), 7.51 (dd, J=9.0, 3.2 Hz, 1H), 7.38-7.49 (m, 6H), 7.20 (dd, J=8.9, 4.5 Hz, 1H), 6.90 (s, 1H).

8-Nitro-3-phenyl-4H-benzo[f][1,4]oxazepin-5-one $^1$H NMR (DMSO-d$_6$) δ (ppm): 10.15 (s, 1H), 8.12 (dd, J=8.5, 2.2 Hz, 1H), 8.04 (d, J=8.5 Hz, 1H), 7.94 (d, J=2.2 Hz, 1H), 7.48-7.52 (m, 2H), 7.38-7.44 (m, 3H), 6.95 (s, 1H).

7-Nitro-3-phenyl-4H-benzo[f][1,4]oxazepin-5-one $^1$H NMR (DMSO-d$_6$) δ (ppm): 10.13 (s, 1H), 8.55 (d, J=2.8 Hz, 1H), 8.40 (dd, J=9.0, 3.0 Hz, 1H), 7.48-7.53 (m, 2H), 7.41 (s, 4H), 6.92 (s, 1H).

9-Methyl-3-phenyl-4H-benzo[f][1,4]oxazepin-5-one $^1$H NMR (DMSO-d$_6$) δ (ppm): 9.76 (s, 1H), 7.58 (dd, 1H), 7.42-7.50 (m, 3H), 7.33-7.42 (m, 3H), 7.16 (t, J=7.6 Hz, 1H), 6.97 (s, 1H), 2.31 (s, 3H).

3-(3-Chloro-phenyl)-4H-benzo[f][1,4]oxazepin-5-one $^1$H NMR (DMSO-d$_6$) δ (ppm): 9.82 (s, 1H), 7.78 (dd, J=7.7, 1.7 Hz, 1H), 7.57 (td, 1H), 7.53-7.54 (m, 1H), 7.40-7.47 (m, 3H), 7.30 (td, J=7.6, 1.1 Hz, 1H), 7.14 (dd, J=8.1, 0.8 Hz, 1H), 6.97 (s, 1H).

7-Fluoro-3-(3-methoxy-phenyl)-4H-benzo[f][1,4]oxazepin-5-one $^1$H NMR (DMSO-d$_6$) δ (ppm): 9.91 (s, 1H), 7.51 (dd, J=8.9, 3.2 Hz, 1H), 7.43 (ddd, J=8.9, 8.1, 3.3 Hz, 1H), 7.30 (t, J=7.9 Hz, 1H), 7.20 (dd, J=8.9, 4.5 Hz, 1H), 7.04 (ddd, J=7.7, 1.6, 0.9 Hz, 1H), 7.01 (t, J=2.0 Hz, 1H), 6.93 (s, 1H), 6.94 (ddd, J=8.3, 2.6, 0.9 Hz, 1H), 3.78 (s, 3H).

7-Fluoro-3-(4-methoxy-phenyl)-4H-benzo[f][1,4]oxazepin-5-one $^1$H NMR (DMSO-d$_6$) δ (ppm): 9.87 (s, 1H), 7.50 (dd, J=9.0, 3.2 Hz, 1H), 7.42 (ddd, J=8.9, 8.1, 3.3 Hz, 1H), 7.39 (d, J=8.9 Hz, 2H), 7.19 (dd, J=8.9, 4.6 Hz, 1H), 6.95 (d, J=8.8 Hz, 2H), 6.79 (s, 1H), 3.76 (s, 3H).

3-(3-Chloro-phenyl)-7-fluoro-4H-benzo[f][1,4]oxazepin-5-one $^1$H NMR (DMSO-d$_6$) δ (ppm): 9.97 (s, 1H), 7.53-7.56 (m, 1H), 7.50 (dd, J=8.9, 3.2 Hz, 1H), 7.36-7.47 (m, 4H), 7.21 (dd, J=8.9, 4.5 Hz, 1H), 6.99 (s, 1H).

3-Thiophen-3-yl-4H-benzo[f][1,4]oxazepin-5-one $^1$H NMR (DMSO-d$_6$) δ (ppm): 7.10 (s, 1H) 7.14 (dd, J=8.12, 0.92 Hz, 1H) 7.28 (td, J=7.50, 1.15 Hz, 1H) 7.31 (dd, J=5.13, 1.34 Hz, 1H) 7.56 (ddd, J=8.39, 7.11, 1.83 Hz, 1H) 7.57 (dd, J=5.13, 2.93 Hz, 1H) 7.67 (dd, J=2.87, 1.28 Hz, 1H) 7.75 (dd, J=7.75, 1.65 Hz, 1H) 9.80 (s, 1H).

Step 3

4-Hydroxy-3-(3-methoxy-phenyl)-2H-isoquinolin-1-one

To a suspension of 1 g (3.74 mmol) of 3-(3-Methoxy-phenyl)-4H-benzo[f][1,4]oxazepin-5-one in dioxane (20 mL), 0.225 g (5.6 mmol) of sodium hydride (60% dispersion in mineral oil) were added under strictly oxygen-free atmosphere and the mixture was heated at 100° C. for 45 min. After cooling to room temperature, 2N hydrochloric acid was added till pH 1 then water was added until complete precipitation of the product was reached. The solid was filtered, washed with water and dried in vacuo, affording 0.82 g of the title compound (82%).

$^1$H NMR (DMSO-$d_6$) δ (ppm): 10.93 (br. s., 1H), 8.28 (s, 1H), 8.22 (ddd, J=8.0, 1.4, 0.6 Hz, 1H), 7.96 (d, J=8.0 Hz, 1H), 7.79 (ddd, J=8.3, 7.0, 1.5 Hz, 1H), 7.54 (ddd, J=8.0, 7.0, 1.2 Hz, 1H), 7.37 (t, J=7.9 Hz, 1H), 7.28 (dt, J=7.7, 1.2 Hz, 1H), 7.24 (dd, J=2.6, 1.6 Hz, 1H), 6.96 (ddd, J=8.2, 2.5, 1.0 Hz, 1H), 3.82 (s, 3H).

According to this same methodology, but employing a suitably substituted starting material, the following compounds were prepared:

4-Hydroxy-3-phenyl-2H-isoquinolin-1-one $^1$H NMR (DMSO-$d_6$) δ (ppm): 10.96 (s, 1H), 8.26 (s, 1H), 8.22 (dd, J=8.0, 0.8 Hz, 1H), 7.96 (d, J=7.8 Hz, 1H), 7.79 (td, J=7.6, 1.3 Hz, 1H), 7.66-7.71 (m, 2H), 7.54 (ddd, J=8.0, 7.1, 1.1 Hz, 1H), 7.43-7.49 (m, 2H), 7.36-7.41 (m, 1H).

7-Acetyl-4-hydroxy-3-phenyl-2H-isoquinolin-1-one $^1$H NMR (DMSO-$d_6$) δ (ppm): 11.27 (s, 1H), 8.77 (d, J=1.6 Hz, 1H), 8.44 (s, 1H), 8.28 (dd, J=8.5, 2.0 Hz, 1H), 8.04 (d, J=8.5 Hz, 1H), 7.71 (d, J=7.7 Hz, 2H), 7.49 (t, J=7.3 Hz, 2H), 7.42 (t, J=7.2 Hz, 1H), 2.69 (s, 3H).

4-Hydroxy-3-(4-methoxy-phenyl)-2H-isoquinolin-1-one $^1$H NMR (DMSO-$d_6$) δ (ppm): 3.81 (s, 3H) 7.02 (d, J=8.91 Hz, 2H) 7.51 (ddd, J=8.03, 7.05, 1.16 Hz, 1H) 7.63 (d, J=8.79 Hz, 2H) 7.77 (ddd, J=8.24, 7.02, 1.34 Hz, 1H) 7.93 (ddd, J=8.06, 0.98, 0.61 Hz, 1H) 8.14 (s, 1H) 8.20 (ddd, J=8.06, 1.34, 0.60 Hz, 1H) 10.90 (s, 1H).

7-Fluoro-4-hydroxy-3-phenyl-2H-isoquinolin-1-one $^1$H NMR (DMSO-$d_6$) δ (ppm): 11.13 (s, 1H), 8.38 (s, 1H), 8.02 (dd, J=9.1, 5.4 Hz, 1H), 7.87 (dd, J=9.5, 2.8 Hz, 1H), 7.66-7.71 (m, 1H), 7.65-7.68 (m, 2H), 7.44-7.49 (m, 2H), 7.37-7.41 (m, 1H).

4-Hydroxy-6-nitro-3-phenyl-2H-isoquinolin-1-one $^1$H NMR (DMSO-$d_6$) δ (ppm): 11.45 (s, 1H), 8.75 (d, J=2.2 Hz, 1H), 8.72 (s, 1H), 8.44 (d, J=8.7 Hz, 1H), 8.25 (dd, J=8.8, 2.3 Hz, 1H), 7.70 (d, J=7.8 Hz, 2H), 7.50 (t, J=7.3 Hz, 2H), 7.44 (t, J=7.3 Hz, 1H).

4-Hydroxy-7-nitro-3-phenyl-2H-isoquinolin-1-one $^1$H NMR (DMSO-$d_6$) δ (ppm): 11.55 (s, 1H), 8.93 (d, J=2.3 Hz, 1H), 8.64 (s, 1H), 8.54 (dd, J=9.0, 2.5 Hz, 1H), 8.14 (d, J=8.9 Hz, 1H), 7.71 (dd, J=7.3, 1.4 Hz, 2H), 7.43-7.54 (m, 3H).

3-(3-Chloro-phenyl)-4-hydroxy-2H-isoquinolin-1-one $^1$H NMR (DMSO-$d_6$) δ (ppm): 11.05 (s, 1H), 8.46 (s, 1H), 8.22 (ddd, J=8.1, 1.3, 0.5 Hz, 1H), 7.97 (d, J=8.1 Hz, 1H), 7.80 (ddd, J=8.2, 7.0, 1.3 Hz, 1H), 7.74 (t, J=1.6 Hz, 1H), 7.64 (dt, J=7.4, 1.4 Hz, 1H), 7.56 (ddd, J=8.0, 7.0, 1.2 Hz, 1H), 7.49 (td, J=7.8, 0.4 Hz, 1H), 7.45 (ddd, J=7.9, 2.0, 1.3 Hz, 1H).

4-Hydroxy-5-methyl-3-phenyl-2H-isoquinolin-1-one

MS calculated: 251.0946. MS found: 251.0950
ESI(+) MS: m/z 252 (MH$^+$).

7-Fluoro-4-hydroxy-3-(3-methoxy-phenyl)-2H-isoquinolin-1-one $^1$H NMR (DMSO-$d_6$) δ (ppm): 11.10 (s, 1H), 8.41 (s, 1H), 8.02 (dd, J=9.1, 5.3 Hz, 1H), 7.87 (dd, J=9.5, 2.7 Hz, 1H), 7.68 (td, J=8.8, 2.8 Hz, 1H), 7.37 (t, J=7.9 Hz, 1H), 7.27 (dt, J=7.8, 1.2 Hz, 1H), 7.23 (dd, J=2.4, 1.6 Hz, 1H), 6.96 (ddd, J=8.2, 2.6, 0.9 Hz, 1H), 3.82 (s, 3H).

7-Fluoro-4-hydroxy-3-(4-methoxy-phenyl)-2H-isoquinolin-1-one $^1$H NMR (DMSO-$d_6$) δ (ppm): 11.06 (s, 1H), 8.27 (s, 1H), 7.99 (dd, J=9.1, 5.2 Hz, 1H), 7.85 (dd, J=9.5, 2.7 Hz, 1H), 7.67 (td, J=8.8, 2.8 Hz, 1H), 7.62 (d, J=8.9 Hz, 2H), 7.02 (d, J=8.9 Hz, 2H), 3.81 (s, 3H).

3-(3-Chloro-phenyl)-7-fluoro-4-hydroxy-2H-isoquinolin-1-one $^1$H NMR (DMSO-$d_6$) δ (ppm): 11.20 (s, 1H), 8.58 (s, 1H), 8.03 (dd, J=8.9, 5.2 Hz, 1H), 7.88 (dd, J=9.4, 2.7 Hz, 1H), 7.73 (t, J=1.5 Hz, 1H), 7.70 (td, J=8.8, 2.8 Hz, 1H), 7.63 (dt, J=7.5, 1.3 Hz, 1H), 7.42-7.52 (m, 2H).

4-Hydroxy-3-thiophen-3-yl-2H-isoquinolin-1-one $^1$H NMR (DMSO-$d_6$) δ (ppm): 7.52 (ddd, J=7.99, 7.08, 1.16 Hz, 1H) 7.63 (dd, J=5.07, 2.99 Hz, 1H) 7.78 (ddd, J=8.24, 7.02, 1.34 Hz, 1H) 7.80 (dd, J=5.07, 1.28 Hz, 1H) 7.97 (ddd, J=8.18, 0.98, 0.60 Hz, 1H) 8.11 (dd, J=2.99, 1.28 Hz, 1H) 8.20 (ddd, J=8.00, 1.34, 0.49 Hz, 1H) 8.55 (s, 1H) 10.85 (s, 1H).

Step 5

{2-[3-(3-Methoxy-phenyl)-1-oxo-1,2-dihydro-isoquinolin-4-yloxy]-ethyl}-carbamic acid tert-butyl ester (I, L=CH$_2$—CH$_2$, R=R$_2$=R$_3$=H, R$_1$=t-butoxycarbonyl and R$_4$=3-methoxyphenyl)

To a solution of 3.79 g (14.19 mmol) of 4-hydroxy-3-(3-methoxy-phenyl)-2H-isoquinolin-1-one in N,N-dimethylacetamide (90 mL), 3.18 g (14.19 mmol) of (2-bromo-ethyl)-carbamic acid tert-butyl ester and 5.09 g (15.6 mmol) of cesium carbonate were added and the resulting mixture was stirred at room temperature for 2 hours under argon. Water was added to the reaction mixture and this was extracted twice with ethyl acetate. The combined organic layers were washed at least three times with water and then evaporated to dryness. The crude was purified by flash chromatography (eluant: ethyl acetate/hexane 1/1) to afford 3.2 g of the title compound (55%).

$^1$H NMR (DMSO-$d_6$) δ (ppm): 11.18 (s, 1H), 8.23 (ddd, J=7.9, 1.2, 0.6 Hz, 1H), 7.89 (d, J=8.0 Hz, 1H), 7.78 (ddd, J=8.1, 7.0, 1.3 Hz, 1H), 7.57 (ddd, J=8.0, 7.0, 1.2 Hz, 1H), 7.40 (t, J=7.9 Hz, 1H), 7.30 (dt, J=8.2, 1.2 Hz, 1H), 7.24 (dd, J=2.4, 1.5 Hz, 1H), 7.01 (ddd, J=8.2, 2.6, 0.9 Hz, 1H), 6.84 (t, J=5.4 Hz, 1H), 3.83 (s, 3H), 3.49 (t, J=5.8 Hz, 2H), 3.08 (q, J=6.0 Hz, 2H), 1.36 (s, 9H).

According to this same methodology, but employing suitably substituted starting materials, the following compounds were prepared:

[2-(1-Oxo-3-phenyl-1,2-dihydro-isoquinolin-4-yloxy)-ethyl]-carbamic acid tert-butyl ester (I, L=$CH_2$—$CH_2$, R=$R_2$=$R_3$=H, $R_1$=t-butoxycarbonyl and $R_4$=phenyl)

$^1$H NMR (DMSO-$d_6$) δ (ppm): 1.36 (s, 9H) 3.06 (q, J=5.61 Hz, 2H) 3.46 (t, J=5.79 Hz, 2H) 6.82 (t, J=5.55 Hz, 1H) 7.56 (ddd, J=8.08, 7.04, 1.22 Hz, 1H) 7.70 (dd, J=8.11, 1.52 Hz, 2H) 7.78 (ddd, J=8.17, 7.07, 1.34 Hz, 1H) 7.88 (d, J=7.92 Hz, 1H) 8.24 (ddd, J=7.92, 1.34, 0.61 Hz, 1H) 11.21 (s, 1H).

[3-(1-Oxo-3-phenyl-1,2-dihydro-isoquinolin-4-yloxy)-propyl]-carbamic acid tert-butyl ester (I, L=$CH_2$—$CH_2$—$CH_2$, R=$R_2$=$R_3$=H, $R_1$=t-butoxycarbonyl and $R_4$=phenyl)

$^1$H NMR (DMSO-$d_6$) δ (ppm): 1.35 (s, 9H) 1.61 (quin, J=6.70 Hz, 2H) 2.91 (q, J=6.40 Hz, 2H) 3.49 (t, J=6.22 Hz, 2H) 6.65 (t, J=5.97 Hz, 1H) 7.56 (ddd, J=8.01, 6.73, 1.46 Hz, 1H) 7.67 (dd, J=8.11, 1.52 Hz, 2H) 7.80 (ddd, J=8.05, 6.83, 1.22 Hz, 1H) 7.84 (dd, J=8.15, 1.40 Hz, 1H) 8.24 (ddd, J=8.05, 1.22, 0.70 Hz, 1H) 11.22 (s, 1H).

4-[2-(1-Oxo-3-phenyl-1,2-dihydro-isoquinolin-4-yloxy)-ethyl]-piperazine-1-carboxylic acid tert-butyl ester (I, L=$CH_2$—$CH_2$, $R_2$=$R_3$=H, R and $R_1$ together=N-t-butoxycarbonyl-piperazino and $R_4$=phenyl)

$^1$H NMR (DMSO-$d_6$) δ (ppm): 1.39 (s, 9H) 2.20 (t, J=5.00 Hz, 4H) 2.34 (t, J=5.00 Hz, 2H) 2.46 (t, J=5.73 Hz, 2H) 3.42 (t, J=5.79 Hz, 2H) 3.56 (t, J=5.42 Hz, 2H) 7.56 (ddd, J=8.05, 7.07, 1.10 Hz, 1H) 7.68 (dd, J=8.05, 1.46 Hz, 2H) 7.82 (ddd, J=8.17, 7.07, 1.34 Hz, 1H) 7.98 (d, J=8.17 Hz, 1H) 8.23 (dd, J=7.98, 0.79 Hz, 1H) 11.21 (s, 1H).

{2-[3-(4-Methoxy-phenyl)-1-oxo-1,2-dihydro-isoquinolin-4-yloxy]-ethyl}-carbamic acid tert-butyl ester (I, L=$CH_2$—$CH_2$, R=$R_2$=$R_3$=H, $R_1$=t-butoxycarbonyl and $R_4$=4-methoxyphenyl)

$^1$H NMR (DMSO-$d_6$) δ (ppm): 1.37 (s, 9H) 3.08 (q, J=5.25 Hz, 2H) 3.46 (t, J=5.74 Hz, 2H) 3.83 (s, 3H) 6.83 (t, J=5.61 Hz, 1H) 7.04 (d, J=8.91 Hz, 2H) 7.54 (ddd, J=8.03, 7.05, 1.16 Hz, 1H) 7.66 (d, J=8.91 Hz, 2H) 7.77 (ddd, J=8.12, 7.02, 1.34 Hz, 1H) 7.86 (d, J=7.93 Hz, 1H) 8.22 (ddd, J=7.93, 1.34, 0.50 Hz, 1H) 11.14 (s, 1H).

[2-(7-Fluoro-1-oxo-3-phenyl-1,2-dihydro-isoquinolin-4-yloxy)-ethyl]-carbamic acid tert-butyl ester (I, L=$CH_2$—$CH_2$, R=$R_3$=H, $R_2$=7-F, $R_1$=t-butoxycarbonyl and $R_4$=phenyl)

$^1$H NMR (DMSO-$d_6$) δ (ppm): 11.37 (s, 1H), 7.95 (dd, J=8.8, 5.3 Hz, 1H), 7.90 (dd, J=9.4, 2.7 Hz, 1H), 7.69 (dd, J=7.9, 1.5 Hz, 2H), 7.67 (td, J=8.9, 2.8 Hz, 1H), 7.44-7.53 (m, 3H), 6.81 (t, J=5.3 Hz, 1H), 3.45 (t, J=5.8 Hz, 2H), 3.05 (q, J=5.4 Hz, 2H), 1.36 (s, 9H).

{2-[3-(3-Chloro-phenyl)-1-oxo-1,2-dihydro-isoquinolin-4-yloxy]-ethyl}-carbamic acid tert-butyl ester (I, L=$CH_2$—$CH_2$, R=$R_2$=$R_3$=H, $R_1$=t-butoxycarbonyl and $R_4$=3-chlorophenyl)

$^1$H NMR (DMSO-$d_6$) δ (ppm): 11.29 (s, 1H), 8.24 (ddd, J=7.9, 1.1, 0.6 Hz, 1H), 7.89 (d, J=8.1 Hz, 1H), 7.80 (ddd, J=8.1, 7.0, 1.3 Hz, 1H), 7.71-7.75 (m, 1H), 7.66-7.70 (m, 1H), 7.59 (ddd, 1H), 7.50-7.54 (m, 2H), 6.84 (t, J=5.4 Hz, 1H), 3.49 (t, J=5.7 Hz, 2H), 3.08 (q, J=5.4 Hz, 2H), 1.36 (s, 9H).

[2-(5-Methyl-1-oxo-3-phenyl-1,2-dihydro-isoquinolin-4-yloxy)-ethyl]-carbamic acid tert-butyl ester (I, L=$CH_2$—$CH_2$, R=$R_2$=H, $R_3$=5-methyl, $R_1$=t-butoxycarbonyl and $R_4$=phenyl)

$^1$H NMR (DMSO-$d_6$) δ (ppm): 11.23 (s, 1H), 8.14 (ddd, J=8.1, 1.5, 0.5 Hz, 1H), 7.70 (dd, J=8.0, 1.5 Hz, 2H), 7.53-7.58 (m, J=7.4, 1.4, 0.5, 0.5, 0.5, 0.5 Hz, 1H), 7.44-7.52 (m, 3H), 7.41 (t, J=7.6 Hz, 1H), 6.55 (t, J=5.6 Hz, 1H), 3.28-3.31 (m, 2H), 2.92 (q, J=5.9 Hz, 2H), 2.75 (s, 3H), 1.34 (s, 9H).

{2-[7-Fluoro-3-(3-methoxy-phenyl)-1-oxo-1,2-dihydro-isoquinolin-4-yloxy]-ethyl}-carbamic acid tert-butyl ester (I, L=$CH_2$—$CH_2$, R=$R_3$=H, $R_2$=7-F, $R_1$=t-butoxycarbonyl and $R_4$=3-methoxyphenyl)

$^1$H NMR (DMSO-$d_6$) δ (ppm): 11.34 (s, 1H), 7.96 (dd, J=8.8, 5.2 Hz, 1H), 7.90 (dd, J=9.4, 2.7 Hz, 1H), 7.67 (td, J=8.8, 2.9 Hz, 1H), 7.40 (t, J=7.9 Hz, 1H), 7.29 (d, J=7.9 Hz, 1H), 7.21-7.25 (m, 1H), 7.01 (ddd, J=8.2, 2.6, 0.8 Hz, 1H), 6.77-6.87 (m, 1H), 3.83 (s, 3H), 3.48 (t, J=5.7 Hz, 2H), 3.08 (q, J=5.6 Hz, 2H), 1.36 (s, 9H).

{2-[7-Fluoro-3-(4-methoxy-phenyl)-1-oxo-1,2-dihydro-isoquinolin-4-yloxy]-ethyl}-carbamic acid tert-butyl ester (I, L=$CH_2$—$CH_2$, R=$R_3$=H, $R_2$=7-F, $R_1$=t-butoxycarbonyl and $R_4$=4-methoxyphenyl)

$^1$H NMR (DMSO-$d_6$) δ (ppm): 11.29 (s, 1H), 7.93 (dd, J=9.0, 5.3 Hz, 1H), 7.88 (dd, J=9.3, 2.7 Hz, 1H), 7.65 (d, J=8.8 Hz, 2H), 7.66 (ddd, J=9.0, 8.0, 2.8 Hz, 1H), 7.04 (d, J=8.9 Hz, 2H), 6.82 (t, J=5.2 Hz, 1H), 3.82 (s, 3H), 3.45 (t, J=5.6 Hz, 2H), 3.08 (q, J=5.7 Hz, 2H), 1.36 (s, 9H).

{2-[3-(3-Chloro-phenyl)-7-fluoro-1-oxo-1,2-dihydro-isoquinolin-4-yloxy]-ethyl}-carbamic acid tert-butyl ester (I, L=$CH_2$—$CH_2$, R=$R_3$=H, $R_2$=7-F, $R_1$=t-butoxycarbonyl and $R_4$=3-chlorophenyl)

$^1$H NMR (DMSO-$d_6$) δ (ppm): 11.43 (s, 1H), 7.96 (dd, J=8.8, 5.3 Hz, 1H), 7.90 (dd, J=9.3, 2.7 Hz, 1H), 7.70-7.74 (m, 1H), 7.64-7.71 (m, 2H), 7.50-7.53 (m, 2H), 6.83 (t, J=5.6 Hz, 1H), 3.49 (t, J=5.7 Hz, 2H), 3.07 (q, J=5.4 Hz, 2H), 1.36 (s, 9H).

[2-(1-Oxo-3-thiophen-3-yl-1,2-dihydro-isoquinolin-4-yloxy)-ethyl]-carbamic acid tert-butyl ester (I, L=$CH_2$—$CH_2$, R=$R_2$=$R_3$=H, $R_1$=t-butoxycarbonyl and $R_4$=thiophen-3-yl)

$^1$H NMR (DMSO-$d_6$) δ (ppm): 1.40 (s, 6H) 3.21-3.28 (m, 2H) 3.60 (t, J=5.55 Hz, 2H) 7.08 (br. s., 1H) 7.55 (td, J=7.54, 1.16 Hz, 1H) 7.67 (dd, J=5.07, 2.99 Hz, 1H) 7.74 (dd, J=5.13, 1.34 Hz, 1H) 7.78 (ddd, J=8.15, 6.99, 1.34 Hz, 1H) 7.84-7.88 (m, 1H) 8.17 (dd, J=2.81, 1.22 Hz, 1H) 8.22 (dd, J=7.99, 0.67 Hz, 1H) 11.09 (s, 1H).

7-Acetyl-3-phenyl-4-(2-piperidin-1-yl-ethoxy)-2H-isoquinolin-1-one (cmpd. 30) (I, L=CH$_2$—CH$_2$, R$_2$=7-acetyl, R$_3$=H, R and R$_1$ together=piperidino and R$_4$=phenyl)

$^1$H NMR (DMSO-d$_6$) δ (ppm): 11.49 (br. s., 1H), 8.77 (d, J=1.5 Hz, 1H), 8.27 (dd, J=8.5, 1.9 Hz, 1H), 8.13 (d, J=8.5 Hz, 1H), 7.71 (dd, J=8.0, 1.5 Hz, 2H), 7.44-7.57 (m, 3H), 3.54 (br. s., 2H), 2.69 (s, 3H), 2.40 (br. s., 2H), 2.21 (br. s., 4H), 1.43 (br. s., 4H), 1.34 (br. s., 2H).

6-Nitro-3-phenyl-4-(2-piperidin-1-yl-ethoxy)-2H-isoquinolin-1-one (cmpd. 31) (I, L=CH$_2$—CH$_2$, R$_2$=6-nitro, R$_3$=H, R and R$_1$ together=piperidino and R$_4$=phenyl)

$^1$H NMR (DMSO-d$_6$) δ (ppm): 11.67 (br. s., 1H), 8.80 (br. s., 1H), 8.45 (d, J=8.8 Hz, 1H), 8.27 (dd, J=8.7, 2.1 Hz, 1H), 7.69-7.74 (m, 2H), 7.48-7.59 (m, 3H), 3.55 (br. s., 2H), 2.39 (br. s., 2H), 2.23 (br. s., 4H), 1.28-1.45 (m, 6H).

4-[2-(dimethylamino)ethoxy]-7-fluoro-3-phenylisoquinolin-1(2H)-one (cmpd. 84) (I, L=CH$_2$CH$_2$, R$_2$=F, R$_3$=H, R=R$_1$=methyl, R$_4$=phenyl)

$^1$H NMR (DMSO-d$_6$) δ (ppm): 11.37 (s, 1H), 8.02 (dd, J=5.25, 8.91 Hz, 1H), 7.89 (dd, J=2.69, 9.40 Hz, 1H), 7.64-7.76 (m, 4H), 7.34-7.55 (m, 4H), 3.53 (t, J=5.74 Hz, 2H), 2.35-2.45 (m, 2H), 2.07 (s, 6H).

Tert-butyl 4-[(7-fluoro-1-oxo-3-phenyl-1,2-dihydroisoquinolin-4-yl)oxy]piperidine-1-carboxylate (I, L taken together with the nitrogen to which it is bonded=piperidin-4-yl, R$_2$=F, R$_3$=H, R=tert-butoxycarbonyl, R$_4$=phenyl)

$^1$H NMR (DMSO-d$_6$) δ (ppm): 11.39 (s, 1H), 7.87-7.96 (m, 1H), 7.63-7.74 (m, 1H), 7.43-7.53 (m, 1H), 4.82 (dt, J=4.26, 8.21 Hz, 1H), 4.14 (dd, J=3.30, 5.74 Hz, 1H), 3.56-3.64 (m, 1H), 3.14-3.22 (m, 1H).

3-(3-Methoxy-phenyl)-4-(3-piperidin-1-yl-propoxy)-2H-isoquinolin-1-one (cmpd. 10) (I, L=CH$_2$—CH$_2$—CH$_2$, R$_2$=R$_3$=H, R and R$_1$ together=piperidino and R$_4$=3-methoxyphenyl)

To a suspension of 766 mg (2.86 mmol) of 4-hydroxy-3-(3-methoxy-phenyl)-2H-isoquinolin-1-one in methanol (29 mL), 1.45 g (5.73 mmol) of 1-(3-Chloro-propyl)-piperidine hydrochloride, 1.58 g (11.5 mmol) of potassium carbonate and 47 mg (0.286 mmol) of potassium iodide were added and the mixture was submitted to microwaves at 85° C. with contemporary cooling for 15 min. The solvent was concentrated in vacuo and the mixture was worked-up with dichloromethane and sodium hydrogenocarbonate saturated solution. The organic layer was washed with brine and then evaporated to dryness. The crude was purified by flash chromatography (eluant: dichloromethane/methanol 96/4) to afford 456 mg of the title compound (41%).

$^1$H NMR (DMSO-d$_6$) δ (ppm): 11.19 (s, 1H), 8.23 (dd, J=7.9, 0.6 Hz, 1H), 7.90 (d, J=7.9 Hz, 1H), 7.80 (ddd, J=8.2, 7.0, 1.3 Hz, 1H), 7.56 (ddd, J=8.0, 7.0, 1.1 Hz, 1H), 7.40 (t, J=7.9 Hz, 1H), 7.27 (dt, J=7.9, 1.1 Hz, 1H), 7.23 (dd, J=2.5, 1.5 Hz, 1H), 7.02 (ddd, J=8.2, 2.6, 0.7 Hz, 1H), 3.83 (s, 3H), 3.55 (t, J=6.2 Hz, 2H), 2.22 (br. s., 6H), 1.68 (br. s., 2H), 1.45 (br. s., 4H), 1.37 (br. s., 2H).

According to this same methodology, but employing suitably substituted starting materials, the following compounds were prepared:

3-(3-Methoxy-phenyl)-4-(2-piperidin-1-yl-ethoxy)-2H-isoquinolin-1-one (cmpd. 9) (I, L=CH$_2$—CH$_2$, R$_2$=R$_3$=H, R and R$_1$ together=piperidino and R$_4$=3-methoxyphenyl)

$^1$H NMR (DMSO-d$_6$) δ (ppm): 1.29-1.39 (m, 2H) 1.39-1.50 (m, 4H) 2.24 (br. s., 4H) 2.44 (t, J=4.82 Hz, 2H) 3.57 (t, J=5.42 Hz, 2H) 3.84 (s, 3H) 7.03 (ddd, J=8.29, 2.56, 0.85 Hz, 1H) 7.25 (dd, J=2.38, 1.52 Hz, 1H) 7.29 (ddd, J=7.68, 1.34, 0.98 Hz, 1H) 7.41 (t, J=7.92 Hz, 1H) 7.56 (td, J=7.56, 1.10 Hz, 1H) 7.81 (ddd, J=8.17, 7.07, 1.34 Hz, 1H) 7.56 (ddd, J=7.98, 7.13, 1.10 Hz, 1H) 8.23 (ddd, J=8.05, 1.22, 0.49 Hz, 1H) 11.17 (s, 1H).

3-(4-Methoxy-phenyl)-4-(3-piperidin-1-yl-propoxy)-2H-isoquinolin-1-one (cmpd. 23) (I, L=CH$_2$—CH$_2$—CH$_2$, R$_2$=R$_3$=H, R and R$_1$ together=piperidino and R$_4$=4-methoxyphenyl)

$^1$H NMR (DMSO-d$_6$) δ (ppm): 1.40 (br. s., 2H) 1.51 (br. s., 4H) 1.76 (br. s., 2H) 2.35 (s, 6H) 3.53 (t, J=6.10 Hz, 2H) 3.83 (s, 3H) 7.06 (d, J=8.79 Hz, 2H) 7.54 (ddd, J=8.15, 6.93, 1.04 Hz, 1H) 7.63 (d, J=8.79 Hz, 2H) 7.79 (ddd, J=8.06, 7.05, 1.10 Hz, 1H) 7.85 (d, J=8.06 Hz, 1H) 8.22 (d, J=7.81 Hz, 1H) 11.17 (br. s., 1H).

3-Phenyl-4-(3-piperidin-1-yl-propoxy)-2H-isoquinolin-1-one trifluoroacetate (cmpd. 5) (I, L=CH$_2$—CH$_2$—CH$_2$, R$_2$=R$_3$=H, R and R$_1$ together=piperidino and R$_4$=phenyl)

$^1$H NMR (400 MHz, DMSO-d$_6$) δ (ppm): 1.36 (qt, J=12.80, 3.29 Hz, 1H) 1.80 (d, J=14.14 Hz, 2H) 1.89 (dq, J=10.80, 5.80 Hz, 2H) 2.72-2.85 (m, 2H) 2.87-2.98 (m, 2H) 3.55 (t, J=5.91 Hz, 2H) 7.56-7.62 (m, 1H) 7.83 (d, J=3.66 Hz, 2H) 8.26 (d, J=7.92 Hz, 1H) 8.92 (br. s., 1H) 11.29 (s, 1H).

4-[3-(1-Oxo-3-phenyl-1,2-dihydro-isoquinolin-4-yloxy)-propyl]-piperazine-1-carboxylic acid tert-butyl ester (I, L=CH$_2$—CH$_2$—CH$_2$, R$_2$=R$_3$=H, R and R$_1$ together=N-t-butoxycarbonyl-piperazino and R$_4$=phenyl)

$^1$H NMR (DMSO-d$_6$) δ (ppm): 1.39 (s, 9H) 1.65 (quin, J=6.43 Hz, 2H) 2.18 (t, J=4.20 Hz, 4H) 2.23 (t, J=6.89 Hz, 2H) 3.23 (t, J=4.50 Hz, 4H) 3.53 (t, J=6.16 Hz, 2H) 7.56 (ddd, J=8.17, 7.19, 1.22 Hz, 1H) 7.65-7.70 (m, 2H) 7.81 (ddd, J=7.80, 7.30, 1.22 Hz, 1H) 7.88 (ddd, J=8.00, 1.10, 0.60 Hz, 1H) 8.23 (ddd, J=8.05, 1.22, 0.50 Hz, 1H) 11.21 (s, 1H).

6-Nitro-3-phenyl-4-(3-piperidin-1-yl-propoxy)-2H-isoquinolin-1-one (cmpd. 34) (I, L=CH$_2$—CH$_2$—CH$_2$, R$_2$=H, R$_3$=6-nitro, R and R$_1$ together=piperidino and R$_4$=phenyl)

$^1$H NMR (DMSO-d$_6$) δ (ppm): 11.69 (br. s., 1H), 8.52 (d, J=2.2 Hz, 1H), 8.46 (d, J=8.8 Hz, 1H), 8.27 (dd, J=8.7, 2.3 Hz, 1H), 7.70 (dd, J=7.9, 1.6 Hz, 2H), 7.46-7.58 (m, 3H), 3.56 (t, J=6.2 Hz, 2H), 2.25 (br. s., 6H), 1.69 (br. s., 2H), 1.45 (br. s., 4H), 1.36 (br. s., 2H).

7-Nitro-3-phenyl-4-(3-piperidin-1-yl-propoxy)-2H-isoquinolin-1-one (cmpd. 35) (I, L=CH$_2$—CH$_2$—CH$_2$, R$_2$=H, R$_3$=7-nitro, R and R$_1$ together=piperidino and R$_4$=phenyl)

$^1$H NMR (DMSO-d$_6$) δ (ppm): 11.77 (br. s., 1H), 8.91 (d, J=2.3 Hz, 1H), 8.49 (dd, J=9.0, 2.5 Hz, 1H), 8.06 (d, J=9.0 Hz, 1H), 7.62-7.71 (m, 2H), 7.48-7.56 (m, 3H), 3.51 (t, J=6.2 Hz, 2H), 2.04-2.91 (m, 6H), 1.32-1.74 (m, 8H)

7-Chloro-3-phenyl-4-(3-piperidin-1-yl-propoxy)-2H-isoquinolin-1-one (cmpd. 37) (I, L=CH$_2$—CH$_2$—CH$_2$, R$_2$=7-Cl, R$_3$=H, R and R$_1$ together=piperidino and R$_4$=phenyl)

$^1$H NMR (DMSO-d$_6$) δ (ppm): 11.42 (s, 1H), 8.17 (d, J=2.0 Hz, 1H), 7.93 (d, J=8.5 Hz, 1H), 7.82 (dd, J=8.7, 2.3 Hz, 1H), 7.67 (dd, J=8.1, 1.6 Hz, 2H), 7.43-7.55 (m, 3H), 3.51 (t, J=6.3 Hz, 2H), 2.18 (br. s., 6H), 1.62 (quin, J=6.7 Hz, 2H), 1.42 (br. s., 4H), 1.28-1.38 (m, 2H).

7-Fluoro-3-phenyl-4-(3-piperidin-1-yl-propoxy)-2H-isoquinolin-1-one (cmpd. 38) (I, L=CH$_2$—CH$_2$—CH$_2$, R$_2$=7-F, R$_3$=H, R and R$_1$ together=piperidino and R$_4$=phenyl)

$^1$H NMR (DMSO-d$_6$) δ (ppm): 11.37 (s, 1H), 7.97 (dd, J=8.9, 5.2 Hz, 1H), 7.89 (dd, J=9.4, 2.8 Hz, 1H), 7.69 (td, J=8.7, 2.8 Hz, 1H), 7.67 (dd, J=8.1, 1.5 Hz, 2H), 7.42-7.53 (m, 3H), 3.51 (t, J=6.2 Hz, 2H), 2.22 (br. s., 6H), 1.64 (quin, J=6.4 Hz, 2H), 1.43 (br. s., 4H), 1.35 (br. s., 2H).

3-(3-Chloro-phenyl)-4-(3-piperidin-1-yl-propoxy)-2H-isoquinolin-1-one (cmpd. 44) (I, L=CH$_2$—CH$_2$—CH$_2$, R$_2$=R$_3$=H, R and R$_1$ together=piperidino and R$_4$=3-chlorophenyl)

$^1$H NMR (DMSO-d$_6$) δ (ppm): 11.29 (s, 1H), 8.24 (ddd, J=7.9, 1.2, 0.5 Hz, 1H), 7.91 (ddd, J=8.1, 1.1, 0.6 Hz, 1H), 7.81 (ddd, J=8.2, 7.0, 1.3 Hz, 1H), 7.73 (td, J=1.6, 0.9 Hz, 1H), 7.64 (tt, J=3.7, 1.7 Hz, 1H), 7.58 (ddd, J=8.0, 7.0, 1.2 Hz, 1H), 7.51-7.54 (m, 2H), 3.55 (t, J=6.2 Hz, 2H), 2.19 (t, J=7.0 Hz, 6H), 1.65 (quin, J=6.6 Hz, 2H), 1.43 (quin, J=5.4 Hz, 4H), 1.30-1.39 (m, 2H).

Methyl-[3-(1-oxo-3-phenyl-1,2-dihydro-isoquinolin-4-yloxy)-propyl]-carbamic acid tert-butyl ester (I, L=CH$_2$—CH$_2$—CH$_2$, R=Methyl, R$_1$=t-butoxycarbonyl, R$_2$=R$_3$=H, and R$_4$=phenyl)

MS calculated: 408.2049. MS found: 408.2046
ESI(+) MS: m/z 409 (MH$^+$).

4-(3-Diethylamino-propoxy)-3-phenyl-2H-isoquinolin-1-one hydrochloride (cmpd. 18) (I, L=CH$_2$—CH$_2$—CH$_2$, R=R$_1$=ethyl, R$_2$=R$_3$=H, and R$_4$=phenyl)

$^1$H NMR (DMSO-d$_6$) δ (ppm): 1.09 (br. s., 6H) 1.80 (br. s., 2H) 3.57 (t, J=5.85 Hz, 2H) 7.47-7.55 (m, 3H) 7.58 (ddd, J=8.02, 6.55, 1.52 Hz, 1H) 7.68 (dd, J=7.99, 1.52 Hz, 2H) 7.82 (td, J=8.05, 1.10 Hz, 1H) 8.25 (d, J=7.93 Hz, 1H) 8.91 (br. s., 1H) 11.27 (br. s., 1H).

3-Phenyl-4-(2-pyrrol-1-yl-ethoxy)-2H-isoquinolin-1-one (cmpd. 13) (I, L=CH$_2$—CH$_2$, R$_2$=R$_3$=H, R and R$_1$ together=pyrrole and R$_4$=phenyl)

$^1$H NMR (DMSO-d$_6$) δ (ppm): 3.65 (t, J=5.12 Hz, 2H) 4.04 (t, J=5.12 Hz, 2H) 6.06 (t, J=2.13 Hz, 2H) 6.75 (t, J=2.07 Hz, 2H) 7.23 (d, J=8.05 Hz, 1H) 7.44-7.49 (m, 2H) 7.49-7.54 (m, 1H) 7.59-7.65 (m, 1H) 7.65-7.70 (m, 2H) 8.20 (dd, J=7.93, 0.73 Hz, 1H) 11.21 (s, 1H).

3-Phenyl-4-(3-pyrrol-1-yl-propoxy)-2H-isoquinolin-1-one (cmpd. 15) (I, L=CH$_2$—CH$_2$—CH$_2$, R$_2$=R$_3$=H, R and R$_1$ together=pyrrole and R$_4$=phenyl)

$^1$H NMR (DMSO-d$_6$) δ (ppm): 1.90 (quin, J=6.60 Hz, 2H) 3.50 (t, J=5.97 Hz, 2H) 3.80 (t, J=7.13 Hz, 2H) 5.91 (t, 2H) 6.55 (t, J=2.07 Hz, 2H) 7.56 (dd, J=8.05, 4.15 Hz, 1H) 7.65-7.71 (m, 2H) 7.80 (d, J=3.54 Hz, 2H) 8.24 (dt, J=7.93, 0.91 Hz, 1H) 11.23 (s, 1H).

3-Phenyl-4-(3-pyrrolidin-1-yl-propoxy)-2H-isoquinolin-1-one (cmpd. 21) (I, L=CH$_2$—CH$_2$—CH$_2$, R$_2$=R$_3$=H, R and R$_1$ together=pyrrolidino and R$_4$=phenyl)

$^1$H NMR (DMSO-d$_6$) δ (ppm): 1.74 (br. s., 6H) 2.63 (br. s., 6H) 3.55 (t, J=6.10 Hz, 2H) 7.57 (ddd, J=8.05, 6.89, 1.28 Hz, 1H) 7.68 (dd, J=8.05, 1.46 Hz, 1H) 7.81 (ddd, J=8.17, 6.95, 1.22 Hz, 1H) 7.87 (dd, J=8.20, 1.20 Hz, 1H) 8.24 (d, J=7.56 Hz, 1H) 11.24 (s, 1H).

7-Fluoro-3-(3-methoxy-phenyl)-4-(3-piperidin-1-yl-propoxy)-2H-isoquinolin-1-one hydrochloride (cmpd. 43) (I, L=CH$_2$—CH$_2$—CH$_2$, R$_2$=H, R$_3$=7-F, R and R$_1$ together=piperidino and R$_4$=3-methoxyphenyl)

$^1$H NMR (DMSO-d$_6$) δ (ppm): 11.41 (s, 1H), 9.43 (br. s., 1H), 7.91 (dd, J=9.2, 4.9 Hz, 1H), 7.91 (dd, J=9.5, 2.8 Hz, 1H), 7.72 (td, J=8.7, 2.8 Hz, 1H), 7.44 (t, J=8.0 Hz, 1H), 7.26 (dt, J=7.9, 1.0 Hz, 1H), 7.21 (dd, J=2.4, 1.6 Hz, 1H), 7.06 (ddd, J=8.3, 2.6, 0.9 Hz, 1H), 3.84 (s, 3H), 3.57 (t, J=5.9 Hz, 2H), 3.24-3.39 (m, 2H), 2.92 (td, J=8.1, 5.1 Hz, 2H), 2.70-2.83 (m, 2H), 1.94 (dq, J=11.0, 5.8 Hz, 2H), 1.57-1.83 (m, 4H), 1.26-1.70 (m, 2H).

4-(2-Chloro-ethoxy)-3-phenyl-2H-isoquinolin-1-one

To a suspension of 180 mg (0.76 mmol) of 4-hydroxy-3-phenyl-2H-isoquinolin-1-one in methanol (6 mL), 315 mg (2.28 mmol) of potassium carbonate and 190 L (2.28 mmol) of 1-bromo-2-chloroethane were added and the mixture was submitted to microwaves at 120° C. for 10 min. The solvent was concentrated under reduced pressure and the resulting crude was purified by flash chromatography (eluant: ethyl acetate/hexane 1/2) affording 100 mg of the title compound (44%).

$^1$H NMR (DMSO-d$_6$) δ (ppm): 11.21 (br. s., 1H), 8.23 (dd, J=7.9, 0.7 Hz, 1H), 7.94 (d, J=7.7 Hz, 1H), 7.81 (ddd, J=8.2, 7.0, 1.4 Hz, 1H), 7.66-7.72 (m, 2H), 7.55 (ddd, J=8.0, 7.1, 1.2 Hz, 1H), 7.42-7.52 (m, 3H), 3.55 (t, J=5.9 Hz, 2H), 2.55 (t, J=5.9 Hz, 2H), 2.25-2.35 (m, 4H), 1.62 (dt, 4H)

Tert-butyl {3-[(7-fluoro-1-oxo-3-phenyl-1,2-dihydroisoquinolin-4-yl)oxy]propyl}carbamate (I, L=CH$_2$CH$_2$CH$_2$, R$_2$=F, R$_3$=R=H, R$_1$=tert-butoxycarbonyl, R$_4$=phenyl)

To a solution of 0.45 g (1.76 mmol) of 7-Fluoro-4-hydroxy-3-phenyl-2H-isoquinolin-1-one in N,N-dimethylformammide (18 mL), 0.38 g (1.58 mmol) of (3-Bromo-propyl)-carbamic acid tert-butyl ester and 0.084 g (3.56 mmol) of sodium hydride were added and the resulting mixture was stirred at room temperature for 2 hours under argon. Water was added to the reaction mixture and this was extracted twice with ethyl acetate. The combined organic layers were washed at least three times with water and then evaporated to dryness. The crude was purified by flash chromatography (eluant: ethyl acetate/hexane 4/6) to afford 0.4 g of the title compound (55%).

$^1$H NMR (DMSO-d$_6$) δ (ppm): 11.37 (s, 1H), 7.85-7.95 (m, 2H), 7.61-7.72 (m, 3H), 7.41-7.54 (m, 3H), 6.65 (br. s., 1H), 3.48 (t, J=6.16 Hz, 2H), 2.86-2.95 (m, 2H), 1.60 (t, J=6.77 Hz, 2H), 1.34-1.37 (m, 8H).

According to this same methodology, but employing suitably substituted starting materials, the following compounds were prepared:

7-fluoro-3-phenyl-4-[2-(tetrahydro-2H-pyran-2-yloxy)ethoxy]isoquinolin-1(2H)-one $^1$H NMR (DMSO-d$_6$) δ (ppm): 11.36 (s, 1H), 8.08 (dd, J=5.25, 8.91 Hz, 1H), 7.89 (dd, J=2.75, 9.34 Hz, 1H), 7.66-7.74 (m, 3H), 7.41-7.54 (m, 3H), 4.47 (t, J=2.50 Hz, 1H).tep 6

4-(2-Morpholin-4-yl-ethoxy)-3-phenyl-2H-isoquinolin-1-one (cmpd. 54) (I, L=CH$_2$—CH$_2$, R$_2$=R$_3$=H, R and R$_1$ together=morpholino and R$_4$=phenyl)

To a suspension of 20 mg (0.07 mmol) of 4-(2-chloroethoxy)-3-phenyl-2H-isoquinolin-1-one in acetonitrile (0.35 mL), 11 mg (0.08 mmol) of potassium carbonate and 7 L (0.08 mmol) of morpholine were added and the mixture was submitted to microwaves at 120° C. for 1 hour. The solvent was concentrated under reduced pressure and the resulting crude was purified by preparative HPLC affording 7 mg of the title compound (28%).

$^1$H NMR (DMSO-d$_6$) δ (ppm): 11.22 (br. s., 1H), 8.24 (d, J=7.7 Hz, 1H), 8.00 (d, J=7.8 Hz, 1H), 7.80-7.86 (m, 1H), 7.67-7.71 (m, 2H), 7.57 (t, J=7.6 Hz, 1H), 7.43-7.53 (m, 3H), 3.54-3.60 (m, 2H), 3.51 (br. s., 4H), 2.42-2.48 (m, 2H), 2.25 (br. s., 4H)

According to this same methodology, but employing suitably substituted derivatives, the following compounds were prepared:

3-Phenyl-4-(2-piperidin-1-yl-ethoxy)-2H-isoquinolin-1-one (cmpd. 51) (I, L=CH$_2$—CH$_2$, R$_2$=R$_3$=H, R and R$_1$ together=piperidino and R$_4$=phenyl)

$^1$H NMR (DMSO-d$_6$) δ (ppm): 11.19 (br. s., 1H), 8.23 (ddd, J=7.9, 1.3, 0.7 Hz, 1H), 8.01 (ddd, J=8.1, 1.0, 0.4 Hz, 1H), 7.80 (ddd, J=8.2, 7.0, 1.3 Hz, 1H), 7.66-7.70 (m, 2H), 7.55 (ddd, J=8.0, 7.1, 1.1 Hz, 1H), 7.43-7.52 (m, 3H), 3.53 (t, J=5.5 Hz, 2H), 2.40 (t, J=5.5 Hz, 2H), 2.21 (t, J=4.9 Hz, 4H), 1.42 (quin, J=5.4 Hz, 4H), 1.33 (q, J=5.6 Hz, 2H).

4-(2-Diethylamino-ethoxy)-3-phenyl-2H-isoquinolin-1-one (cmpd. 52) (I, L=CH$_2$—CH$_2$, R=R$_1$=ethyl, R$_2$=R$_3$=H and R$_4$=phenyl)

$^1$H NMR (DMSO-d$_6$) δ (ppm): 11.20 (br. s., 1H), 8.23 (ddd, J=8.1, 1.3, 0.5 Hz, 1H), 7.98 (ddd, J=8.2, 1.1, 0.6 Hz, 1H), 7.81 (ddd, J=8.2, 7.0, 1.3 Hz, 1H), 7.66-7.71 (m, 2H), 7.56 (ddd, J=8.1, 7.0, 1.2 Hz, 1H), 7.43-7.53 (m, 3H), 3.50 (t, J=6.3 Hz, 2H), 2.51-2.54 (m, 2H), 2.36 (q, J=7.1 Hz, 4H), 0.85 (t, J=7.1 Hz, 6H).

3-Phenyl-4-(2-pyrrolidin-1-yl-ethoxy)-2H-isoquinolin-1-one (cmpd. 53) (I, L=CH$_2$—CH$_2$—, R$_2$=R$_3$=H, R and R$_1$ together=pyrrolidino and R$_4$=phenyl)

$^1$H NMR (DMSO-d$_6$) δ (ppm): 11.21 (br. s., 1H), 8.23 (dd, J=7.9, 0.7 Hz, 1H), 7.94 (d, J=7.7 Hz, 1H), 7.81 (ddd, J=8.2, 7.0, 1.4 Hz, 1H), 7.66-7.72 (m, 2H), 7.55 (ddd, J=8.0, 7.1, 1.2 Hz, 1H), 7.42-7.52 (m, 3H), 3.55 (t, J=5.9 Hz, 2H), 2.55 (t, J=5.9 Hz, 2H), 2.25-2.35 (m, 4H), 1.62 (dt, 4H).

4-[3-(benzylamino)propoxy]-7-fluoro-3-phenylisoquinolin-1(2H)-one (cmpd. 87) (I, L=CH$_2$CH$_2$CH$_2$, R$_2$=F, R$_3$=R=H, R$_1$=benzyl, R$_4$=phenyl)

To a suspension of 50 mg (0.14 mmol) of 4-(3-aminopropoxy)-7-fluoro-3-phenylisoquinolin-1(2H)-one hydrochloride in methanol (1 mL), 23 mg (0.28 mmol) of sodium acetate, 10.5 mg (1.12 mmol) of zinc chloride and 21 l (0.21 mmol) of benzaldehyde were added and the resulting mixture was stirred at room temperature for 18 hours. Then, 10.5 mg (0.28 mmol) of sodium cyanoborohydride were added and the reaction was stirred for 4 hours. The solvent was removed under reduced pressure and the resulting solid residue was diluted with ethyl acetate and washed twice with water. The combined organic layers were evaporated to dryness and the crude was purified by flash chromatography (eluant: dichloromethane/methanol 9/1) to afford 32 mg of the title compound (57%).

$^1$H NMR (DMSO-d$_6$) δ (ppm): 11.17 (s, 1H), 7.83-7.95 (m, 2H), 7.61-7.70 (m, 3H), 7.39-7.49 (m, 3H), 7.26-7.34 (m, 5H), 7.18-7.26 (m, 1H), 3.64 (s, 2H), 3.55 (t, J=6.16 Hz, 2H), 1.66 (quin, J=6.16 Hz, 2H).

4-[2-(diethylamino)ethoxy]-7-fluoro-3-phenylisoquinolin-1(2H)-one trifluoroacetate (cmpd. 88) (I, L=CH$_2$CH$_2$, R$_2$=F, R$_3$=H, R=R$_1$=ethyl, R$_4$=phenyl)

To a solution of 20 mg (0.048 mmol) of 7-fluoro-4-(2-iodoethoxy)-3-phenylisoquinolin-1(2H)-one in N,N-dimethylformammide (1 mL), 13.5 mg (0.097 mmol) of potassium carbonate and 0.01 ml (0.097 mmol) of diethylamine were added. The mixture was heated at 100° C. for 3 hours. The solvent was removed under reduced pressure and the residue was diluted with dichloromethan and washed twice with water. The combined organic layers were evaporated to dryness and the crude was purified by reverse phase chromatography to afford 2 mg of the title compound (3%).

$^1$H NMR (DMSO-d$_6$) δ (ppm): 0.85 (t, J=7.1 Hz, 6H), 2.32-2.40 (m, 4H), 2.52-2.55 (m, 2H), 3.48 (t, J=6.1 Hz, 2H), 7.44-7.52 (m, 3H), 7.65-7.70 (m, 2H), 7.71 (ddd, J=8.8, 8.8, 2.7 Hz, 1H), 7.89 (dd, J=9.3, 2.7 Hz, 1H), 8.07 (dd, J=8.8, 5.2 Hz, 1H), 8.32 (broad signal. 1H).

According to this same methodology, but employing suitably substituted derivatives, the following compounds were prepared:

7-fluoro-4-[2-(4-methylpiperazin-1-yl)ethoxy]-3-phenylisoquinolin-1(2H)-one trifluoroacetate (cmpd. 89) (I, L=CH$_2$CH$_2$, R$_2$=F, R$_3$=H, R and R$_1$ together=4-methylpiperazin-1-yl, R$_4$=phenyl)

$^1$H NMR (DMSO-d$_6$) δ (ppm): 11.40 (s, 1H), 8.05 (dd, J=5.31, 8.97 Hz, 1H), 7.91 (dd, J=2.75, 9.34 Hz, 1H), 7.75 (td, J=2.81, 8.79 Hz, 1H), 7.64-7.71 (m, 2H), 7.43-7.56 (m, 3H).

7-fluoro-3-phenyl-4-[2-(phenylamino)ethoxy]iso-
quinolin-1(2H)-one trifluoroacetate (cmpd. 90) (I,
L=CH$_2$CH$_2$, R$_2$=F, R$_3$=R=H, and
R$_1$=R$_4$=phenyl)

MS+1 calculated: 375.1504; MS+1 found: 375.1504
ESI(+) MS: m/z 375 (MH$^+$).
$^1$H NMR (DMSO-d$_6$) δ (ppm): 11.39 (s, 1H), 7.98 (dd, J=5.13, 9.03 Hz, 1H), 7.88 (dd, J=2.75, 9.34 Hz, 1H), 7.67-7.73 (m, 2H), 7.61 (td, J=2.81, 8.73 Hz, 1H), 7.44-7.53 (m, 3H), 6.99-7.06 (m, 2H), 6.48-6.54 (m, 1H), 6.45 (dd, J=1.04, 8.61 Hz, 2H), 5.43-5.50 (m, 1H), 3.59 (t, J=5.92 Hz, 2H), 3.13-3.22 (m, 2H).

Example 2

4-(3-aminopropoxy)-7-fluoro-3-phenylisoquinolin-1
(2H)-one hydrochloride (cmpd. 86) (I,
L=CH$_2$CH$_2$CH$_2$, R$_2$=F, R$_3$=R=R$_1$=H,
R$_4$=phenyl)

A solution of 620 mg (1.5 mmol) of tert-butyl {3-[(7-fluoro-1-oxo-3-phenyl-1,2-dihydroisoquinolin-4-yl)oxy]propyl}carbamate in 4M hydrochloric acid in dioxane (7 mL) was stirred for 4 hours at room temperature. Solvent was evaporated to dryness and the solid residue was treated with diethyl ether until precipitation of the hydrochloride salt occurred. The product was collected by filtration, washed with diethyl ether, affording 490 mg of the title compound (95%) as a white solid.
$^1$H NMR (DMSO-d$_6$) δ (ppm): 11.42 (s, 1H), 7.87-7.94 (m, 2H), 7.72 (td, J=2.81, 8.73 Hz, 4H), 7.64-7.68 (m, 2H), 7.44-7.55 (m, 3H), 3.52-3.60 (m, 2H), 2.67-2.75 (m, 2H), 1.72-1.83 (m, 2H).

According to this same methodology, but employing suitably substituted starting materials, the following compounds were prepared:

7-fluoro-3-phenyl-4-(piperidin-4-yloxy)isoquinolin-
1(2H)-one hydrochloride (cmpd. 85) (I, L taken
together with the nitrogen to which it is
bonded=piperidin-4-yl, R$_2$=F, R$_3$=R=H,
R$_4$=phenyl)

$^1$H NMR (DMSO-d$_6$) δ (ppm): 11.43 (s, 1H), 8.22-8.55 (m, 2H), 7.92 (dd, J=2.81, 9.28 Hz, 1H), 7.84-7.89 (m, 1H), 7.72 (td, J=2.81, 8.73 Hz, 1H), 7.61-7.68 (m, 2H), 7.44-7.55 (m, 4H), 3.80-3.92 (m, 1H), 2.86 (br. s., 2H), 2.67 (dt, J=1.85, 3.75 Hz, 2H), 1.79 (br. s., 2H), 1.52 (br. s., 2H).

Example 3

Conversion A 4-(2-Amino-ethoxy)-3-(3-methoxy-phenyl)-2H-iso-
quinolin-1-one hydrochloride (cmpd. 11) (I,
L=CH$_2$—CH$_2$—, R=R$_1$=R$_2$=R$_3$=H and R$_4$=3-
methoxyphenyl)

To a solution of 3.2 g (7.8 mmol) of {2-[3-(3-Methoxy-phenyl)-1-oxo-1,2-dihydro-isoquinolin-4-yloxy]-ethyl}-carbamic acid tert-butyl ester in methanol (10 mL), 4M hydrochloric acid in dioxane (10 mL) was added and the mixture was stirred for 4 hours at room temperature under argon atmosphere. Solvent was evaporated to dryness and the solid residue was treated with methanol and then diethyl ether until precipitation of the hydrochloride salt occurred. The product was collected by filtration, washed with diethyl ether, affording 2.62 g of the title compound (97%) as a white solid.
$^1$H NMR (DMSO-d$_6$) δ (ppm): 11.27 (s, 1H), 8.25 (dd, J=8.0, 0.8 Hz, 1H), 8.11 (br. s., 3H), 7.98 (d, J=7.8 Hz, 1H), 7.83 (ddd, J=8.1, 7.1, 1.3 Hz, 1H), 7.59 (ddd, J=8.0, 7.1, 1.1 Hz, 1H), 7.43 (t, J=7.9 Hz, 1H), 7.33 (dt, J=7.8, 1.0 Hz, 1H), 7.24 (dd, J=2.3, 1.8 Hz, 1H), 7.05 (ddd, 1H), 3.84 (s, 3H), 3.72 (t, J=5.5 Hz, 2H), 2.96 (sxt, J=5.5 Hz, 2H).

According to this same methodology, but employing suitably substituted starting materials, the following compounds were prepared:

4-(2-Amino-ethoxy)-3-phenyl-2H-isoquinolin-1-one
hydrochloride (cmpd. 1) (I, L=CH$_2$—CH$_2$,
R=R$_1$=R$_2$=R$_3$=H, and R$_4$=phenyl)

$^1$H NMR (DMSO-d$_6$) δ (ppm): 2.95 (sxt, J=5.36 Hz, 2H) 3.68 (t, J=5.42 Hz, 2H) 7.59 (ddd, J=8.02, 7.04, 1.16 Hz, 1H) 7.83 (ddd, J=8.17, 7.07, 1.34 Hz, 1H) 7.96 (d, J=8.17 Hz, 1H) 7.98 (br. s., 3H) 8.26 (ddd, J=8.05, 1.22, 0.50 Hz, 1H) 11.30 (s, 1H).

4-(3-Amino-propoxy)-3-phenyl-2H-isoquinolin-1-
one hydrochloride (cmpd. 3) (I, L=CH$_2$—CH$_2$—
CH$_2$, R=R$_1$=R$_2$=R$_3$=H, and R$_4$=phenyl)

$^1$H NMR (DMSO-d$_6$) δ (ppm): 1.74-1.85 (m, 2H) 2.67-2.77 (m, 2H) 3.57 (t, J=6.10 Hz, 2H) 7.58 (ddd, J=8.11, 4.88, 3.35 Hz, 1H) 7.67 (dd, J=7.92, 1.58 Hz, 2H) 7.70 (br. s., 3H) 8.25 (d, J=7.92 Hz, 1H) 11.27 (s, 1H).

4-(3-Methylamino-propoxy)-3-phenyl-2H-isoquino-
lin-1-one hydrochloride (cmpd. 12) (I, L=CH$_2$—
CH$_2$—CH$_2$, R=methyl, R$_1$=R$_2$=R$_3$=H, and
R$_4$=phenyl)

$^1$H NMR (DMSO-d$_6$) δ (ppm): 1.77-1.87 (m, 2H) 2.49 (t, J=5.49 Hz, 3H) 2.73-2.83 (m, 2H) 3.57 (t, J=6.04 Hz, 2H) 7.58 (dt, J=8.05, 4.15 Hz, 1H) 7.67 (dd, J=7.99, 1.52 Hz, 2H) 7.83 (d, J=3.66 Hz, 2H) 8.25 (d, J=8.05 Hz, 1H) 8.48 (br. s., 2H) 11.28 (s, 1H).

4-(4-Amino-butoxy)-3-phenyl-2H-isoquinolin-1-one
hydrochloride (cmpd. 22) (I, L=CH$_2$—CH$_2$—CH$_2$—
CH$_2$, R=R$_1$=R$_2$=R$_3$=H, and R$_4$=phenyl)

$^1$H NMR (DMSO-d$_6$) δ (ppm): 1.57 (br. s., 4H) 2.69 (br. s., 2H) 3.49 (br. s., 2H) 7.58 (dt, J=7.99, 4.18 Hz, 1H) 7.73 (br. s., 3H) 7.69 (dd, J=8.05, 1.34 Hz, 2H) 7.83 (d, J=3.66 Hz, 2H) 8.26 (d, J=7.93 Hz, 1H) 8.73 (br. s., 1H) 11.26 (s, 1H).

3-Phenyl-4-(2-piperazin-1-yl-ethoxy)-2H-isoquino-
lin-1-one di-hydrochloride (cmpd. 6) (I, L=CH$_2$—
CH$_2$, R$_2$=R$_3$=H, R and R$_1$ together=piperazino and
R$_4$=phenyl)

$^1$H NMR (DMSO-d$_6$) δ (ppm): 3.66-3.73 (m, 2H) 3.77 (br. s., 2H) 7.59 (ddd, J=8.05, 7.07, 1.10 Hz, 1H) 7.66-7.72 (m, 2H) 7.83 (ddd, J=8.11, 7.13, 1.34 Hz, 1H) 7.96 (d, J=8.05 Hz, 1H) 8.25 (dd, J=7.92, 0.73 Hz, 1H) 9.43 (br. s., 3H) 11.30 (s, 1H).

4-(2-Amino-ethoxy)-3-(4-methoxy-phenyl)-2H-iso-
quinolin-1-one hydrochloride (cmpd. 24) (I,
L=CH$_2$—CH$_2$, R=R$_1$=R$_2$=R$_3$=H and R$_4$=4-
methoxyphenyl)

$^1$H NMR (DMSO-d$_6$) δ (ppm): 2.97 (sxt, J=5.54 Hz, 2H) 3.68 (t, J=5.43 Hz, 2H) 3.84 (s, 3H) 7.02-7.09 (m, 2H) 7.52-

7.60 (m, 1H) 7.66-7.72 (m, 2H) 7.81 (td, J=7.63, 1.34 Hz, 1H) 7.95 (d, J=7.81 Hz, 1H) 8.06-8.14 (m, 3H) 8.24 (dd, J=7.93, 0.73 Hz, 1H) 11.22 (s, 1H).

3-Phenyl-4-(3-piperazin-1-yl-propoxy)-2H-isoquinolin-1-one di-hydrochloride (cmpd. 14) (I, L=CH$_2$—CH$_2$—CH$_2$, R$_2$=R$_3$=H, R and R$_1$ together=piperazino and R$_4$=phenyl)

$^1$H NMR (DMSO-d$_6$) δ (ppm): 1.94 (br. s., 2H) 3.57 (t, J=5.79 Hz, 2H) 7.58 (ddd, J=8.02, 6.49, 1.71 Hz, 1H) 7.65-7.72 (m, 2H) 7.82 (ddd, J=8.05, 7.02, 1.22 Hz, 1H) 7.86 (dd, J=8.20, 1.22 Hz, 0H) 8.25 (d, J=7.93 Hz, 1H) 9.37 (br. s., 2H) 11.28 (s, 1H) 11.44 (br. s., 1H).

4-(2-Amino-ethoxy)-7-fluoro-3-phenyl-2H-isoquinolin-1-one hydrochloride (cmpd. 39) (I, L=CH$_2$—CH$_2$, R=R$_1$=R$_3$=H, R$_2$=7-F and R$_4$=phenyl)

$^1$H NMR (DMSO-d$_6$) δ (ppm): 11.46 (br. s., 1H), 8.07 (dd, J=9.1, 5.2 Hz, 1H), 8.07 (br. s., 3H), 7.92 (dd, J=9.3, 2.7 Hz, 1H), 7.66-7.77 (m, 3H), 7.40-7.57 (m, 3H), 3.67 (t, J=5.2 Hz, 2H), 2.94 (t, J=5.4 Hz, 2H).

4-(2-Amino-ethoxy)-7-fluoro-3-(4-methoxy-phenyl)-2H-isoquinolin-1-one hydrochloride (cmpd. 25) (I, L=CH$_2$—CH$_2$, R=R$_1$=R$_3$=H, R$_2$=7-F and R$_4$=4-methoxyphenyl)

$^1$H NMR (DMSO-d$_6$) δ (ppm): 11.38 (s, 1H), 8.02 (dd, J=8.9, 5.2 Hz, 1H), 7.98 (br. s., 3H), 7.90 (dd, J=9.3, 2.8 Hz, 1H), 7.71 (td, J=8.7, 2.8 Hz, 1H), 7.67 (d, J=8.8 Hz, 2H), 7.06 (d, J=8.9 Hz, 2H), 3.83 (s, 3H), 3.65 (t, J=5.4 Hz, 2H), 2.98 (sxt, J=5.4 Hz, 2H).

4-(2-Amino-ethoxy)-7-fluoro-3-(3-methoxy-phenyl)-2H-isoquinolin-1-one hydrochloride (cmpd. 46) (I, L=CH$_2$—CH$_2$, R=R$_1$=R$_3$=H, R$_2$=7-F and R$_4$=3-methoxyphenyl)

$^1$H NMR (DMSO-d$_6$) δ (ppm): 11.42 (s, 1H), 8.05 (dd, J=8.8, 5.2 Hz, 1H), 7.99 (br. s., 3H), 7.92 (dd, J=9.3, 2.7 Hz, 1H), 7.73 (td, J=8.7, 2.8 Hz, 1H), 7.43 (t, J=8.0 Hz, 1H), 7.29-7.33 (m, 1H), 7.21-7.25 (m, 1H), 7.05 (ddd, J=8.3, 2.6, 0.9 Hz, 1H), 3.84 (s, 3H), 3.69 (t, J=5.4 Hz, 2H), 2.92-3.04 (m, 2H).

4-(2-Amino-ethoxy)-3-(3-chloro-phenyl)-2H-isoquinolin-1-one hydrochloride (cmpd. 48) (I, L=CH$_2$—CH$_2$, R=R$_1$=R$_2$=R$_3$=H and R$_4$=3-chlorophenyl)

$^1$H NMR (DMSO-d$_6$) δ (ppm): 11.34 (s, 1H), 8.23 (ddd, J=7.9, 1.2, 0.5 Hz, 1H), 7.97 (br. s., 3H), 7.94 (d, J=8.1 Hz, 1H), 7.82 (ddd, J=8.1, 7.1, 1.3 Hz, 1H), 7.72 (t, J=1.8 Hz, 1H), 7.67 (dt, J=6.4, 2.0 Hz, 1H), 7.59 (ddd, J=8.0, 7.1, 1.0 Hz, 1H), 7.48-7.55 (m, 2H), 3.68 (t, J=5.4 Hz, 2H), 2.89-3.02 (m, 2H).

4-(2-Amino-ethoxy)-5-methyl-3-phenyl-2H-isoquinolin-1-one hydrochloride (cmpd. 49) (I, L=CH$_2$—CH$_2$, R=R$_1$=R$_3$=H, R$_2$=5-methyl and R$_4$=phenyl)

$^1$H NMR (DMSO-d$_6$) δ (ppm): 11.33 (br. s., 1H), 8.16 (ddd, J=7.9, 1.4, 0.5 Hz, 1H), 7.74 (br. s., 3H), 7.70 (dd, J=7.8, 1.8 Hz, 2H), 7.59 (ddd, J=7.3, 1.4, 0.7 Hz, 1H), 7.47-7.56 (m, 3H), 7.44 (t, J=7.6 Hz, 1H), 3.54 (t, J=6.0 Hz, 2H), 2.76 (s, 3H), 2.68 (t, J=6.0 Hz, 2H).

4-(2-Amino-ethoxy)-3-(3-chloro-phenyl)-7-fluoro-2H-isoquinolin-1-one hydrochloride (cmpd. 50) (I, L=CH$_2$—CH$_2$, R=R$_1$=R$_3$=H, R$_2$=7-F and R$_4$=3-chlorophenyl)

$^1$H NMR (DMSO-d$_6$) δ (ppm): 11.51 (s, 1H), 8.05 (dd, J=9.0, 5.2 Hz, 1H), 7.98 (br. s., 3H), 7.93 (dd, J=9.3, 2.7 Hz, 1H), 7.74 (t, J=1.7 Hz, 1H), 7.74 (td, J=8.8, 2.8 Hz, 2H), 7.69 (dt, J=6.7, 1.8 Hz, 1H), 7.57 (dt, J=7.9, 1.9 Hz, 1H), 7.54 (t, J=8.1 Hz, 1H), 3.69 (t, J=5.3 Hz, 2H), 2.98 (br. s., 1H).

4-(2-Amino-ethoxy)-3-thiophen-3-yl-2H-isoquinolin-1-one hydrochloride (cmpd. 29) (I, L=CH$_2$—CH$_2$, R=R$_1$=R$_2$=R$_3$=H and R$_4$=thiophenyl)

$^1$H NMR (DMSO-d$_6$) δ (ppm): 3.13-3.20 (m, 2H) 3.79 (t, J=5.25 Hz, 2H) 7.54-7.61 (m, 2H) 7.69-7.74 (m, 2H) 7.82 (td, J=7.63, 1.34 Hz, 2H) 7.95 (d, J=8.18 Hz, 2H) 8.13 (br. s., 3H) 8.18 (t, J=2.07 Hz, 1H) 8.24 (dd, J=7.93, 0.73 Hz, 1H) 11.18 (s, 1H).

Example 4

Conversion B

7-Fluoro-3-(3-hydroxy-phenyl)-4-(3-piperidin-1-yl-propoxy)-2H-isoquinolin-1-one hydrochloride (cmpd. 45) (I, L=CH$_2$—CH$_2$—CH$_2$, R and R$_1$ together=piperidino, R$_3$=H, R$_2$=7-F and R$_4$=3-hydroxyphenyl)

To a solution of 68 mg (0.166 mmol) of 7-fluoro-3-(3-methoxy-phenyl)-4-(3-piperidin-1-yl-propoxy)-2H-isoquinolin-1-one hydrochloride (cmpd. 43) in anhydrous dichloromethane (1 mL), boron tribromide (1M in dichloromethane) (1 mL, 1 mmol) was added and the mixture was stirred overnight at room temperature under argon atmosphere. The solvent was concentrated under reduced pressure and the crude was purified by flash chromatography (eluant: starting with dichloromethane/methanol/acetone/7N ammonia in methanol: 93/3/3/1 to 88/6/5/1) to afford the free base, which was then converted into the hydrochloride salt according to common chemical procedures (58 mg of the title compound, 81%).

$^1$H NMR (DMSO-d$_6$) δ (ppm): 11.35 (s, 1H), 9.73 (s, 1H), 9.49 (br. s., 1H), 7.88-7.92 (m, 2H), 7.71 (td, J=8.8, 2.7 Hz, 1H), 7.32 (t, J=8.1 Hz, 1H), 7.05-7.08 (m, 2H), 6.89 (ddd, J=8.1, 2.3, 1.0 Hz, 1H), 3.56 (t, J=5.8 Hz, 2H), 2.90 (dt, J=10.6, 5.3 Hz, 2H), 2.70-2.82 (m, J=12.3, 12.3, 9.2, 3.5 Hz, 2H), 1.87-2.01 (m, 2H), 1.60-1.81 (m, 6H), 1.29-1.42 (m, 2H)

According to this same methodology, but employing suitably substituted starting material, the following compounds were prepared:

4-(2-Amino-ethoxy)-7-fluoro-3-(3-hydroxy-phenyl)-2H-isoquinolin-1-one (cmpd. 47) (I, L=CH$_2$—CH$_2$, R=R$_1$=R$_3$=H, R$_2$=7-F and R$_4$=3-hydroxyphenyl)

$^1$H NMR (DMSO-d$_6$) δ (ppm): 11.35 (s, 1H), 9.70 (s, 1H), 8.03 (dd, J=8.9, 5.2 Hz, 1H), 7.99 (br. s., 3H), 7.90 (dd, J=9.3, 2.7 Hz, 1H), 7.72 (td, J=8.7, 2.8 Hz, 1H), 7.31 (t, J=7.8 Hz, 1H), 7.12 (dt, J=7.9, 1.4 Hz, 1H), 7.09 (t, J=2.0 Hz, 1H), 6.88 (ddd, J=8.1, 2.4, 0.7 Hz, 1H), 3.69 (t, J=5.4 Hz, 2H), 2.98 (sxt, J=5.4 Hz, 2H).

4-(2-Amino-ethoxy)-7-fluoro-3-(4-hydroxy-phenyl)-2H-isoquinolin-1-one hydrobromide (cmpd. 28) (I, L=$CH_2$—$CH_2$, R=$R_1$=$R_3$=H, $R_2$=7-F and $R_4$=4-hydroxyphenyl)

$^1$H NMR (DMSO-$d_6$) δ (ppm): 3.00 (br. s., 2H) 3.65 (t, J=5.37 Hz, 2H) 6.88 (d, J=8.67 Hz, 2H) 7.55 (d, J=8.67 Hz, 2H) 7.70 (td, J=8.73, 2.81 Hz, 1H) 7.90 (br. s., 3H) 7.89 (dd, J=9.28, 2.81 Hz, 2H) 8.00 (dd, J=8.97, 5.31 Hz, 1H) 9.85 (s, 1H) 11.30 (s, 1H).

3-(3-Hydroxy-phenyl)-4-(3-piperidin-1-yl-propoxy)-2H-isoquinolin-1-one (cmpd. 33) (I, L=$CH_2$—$CH_2$—$CH_2$, R and $R_1$ together=piperidino, $R_2$=$R_3$=H and $R_4$=3-hydroxyphenyl)

$^1$H NMR (DMSO-$d_6$) δ (ppm): 11.10 (s, 1H), 9.57 (s, 1H), 8.22 (dd, J=8.0, 0.8 Hz, 1H), 7.89 (d, J=7.9 Hz, 1H), 7.79 (ddd, J=8.1, 7.0, 1.3 Hz, 1H), 7.54 (ddd, J=8.0, 7.0, 1.1 Hz, 1H), 7.28 (t, J=8.1 Hz, 1H), 7.08 (t, J=1.7 Hz, 1H), 7.07 (dt, J=6.6, 1.2 Hz, 1H), 6.84 (ddd, J=8.1, 2.4, 0.9 Hz, 1H), 3.53 (t, J=6.2 Hz, 2H), 2.22 (t, J=7.0 Hz, 6H), 1.66 (quin, J=6.7 Hz, 2H), 1.43 (quin, J=5.1 Hz, 4H), 1.28-1.39 (m, J=5.3, 5.3, 5.3, 5.3, 4.8 Hz, 2H).

3-(4-Hydroxy-phenyl)-4-(3-piperidin-1-yl-propoxy)-2H-isoquinolin-1-one (cmpd. 27) (I, L=$CH_2$—$CH_2$—$CH_2$, R and $R_1$ together=piperidino, $R_2$=$R_3$=H and $R_4$=4-hydroxyphenyl)

$^1$H NMR (DMSO-$d_6$) δ (ppm): 1.31-1.40 (m, 2H) 1.40-1.52 (m, 4H) 1.67 (quin, J=6.59 Hz, 2H) 2.24 (br. s., 6H) 3.51 (t, J=6.23 Hz, 2H) 6.85 (d, J=8.79 Hz, 2H) 7.51 (ddd, J=8.00, 7.08, 1.28 Hz, 3H) 7.51 (d, J=8.67 Hz, 2H) 7.77 (ddd, J=8.18, 7.02, 1.28 Hz, 1H) 7.86 (d, J=7.95 Hz, 1H) 8.20 (ddd, J=7.93, 1.10, 0.49 Hz, 1H) 9.75 (s, 1H) 11.05 (s, 1H).

4-(2-Amino-ethoxy)-3-(3-hydroxy-phenyl)-2H-isoquinolin-1-one hydrochloride (cmpd. 32) (I, L=$CH_2$—$CH_2$, R=$R_1$=$R_2$=$R_3$=H and $R_4$=3-hydroxyphenyl)

$^1$H NMR (DMSO-$d_6$) δ (ppm): 11.19 (s, 1H), 9.72 (s, 1H), 8.24 (dd, J=8.1, 0.7 Hz, 1H), 8.08 (br. s., 3H), 7.96 (d, J=8.1 Hz, 1H), 7.82 (td, J=7.6, 1.3 Hz, 1H), 7.58 (dd, J=15.1, 1.1 Hz, 1H), 7.31 (t, J=7.9 Hz, 1H), 7.09-7.15 (m, 2H), 6.88 (ddd, J=8.1, 2.2, 1.0 Hz, 1H), 3.72 (t, J=5.4 Hz, 2H), 2.91-3.05 (m, 2H).

4-(2-Amino-ethoxy)-3-(4-hydroxy-phenyl)-2H-isoquinolin-1-one (cmpd. 26) (I, L=$CH_2$—$CH_2$, R=$R_1$=$R_2$=$R_3$=H and $R_4$=4-hydroxyphenyl)

$^1$H NMR (DMSO-$d_6$) δ (ppm): 2.64 (t, J=5.74 Hz, 2H) 3.46 (t, J=5.74 Hz, 2H) 6.81-6.89 (m, 2H) 7.48-7.56 (m, 3H) 7.78 (td, J=7.60, 1.28 Hz, 1H) 7.90 (d, J=7.93 Hz, 1H) 8.20 (dd, J=8.12, 0.67 Hz, 1H).

Example 5

Conversion C

7-Amino-3-phenyl-4-(3-piperidin-1-yl-propoxy)-2H-isoquinolin-1-one (cmpd. 36) (I, L=$CH_2$—$CH_2$—$CH_2$, R and $R_1$ together=piperidino, $R_2$=7-amino, $R_3$=H and $R_4$=phenyl)

To a suspension of 575 mg (1.41 mmol) of 7-nitro-3-phenyl-4-(3-piperidin-1-yl-propoxy)-2H-isoquinolin-1-one (cmpd. 35) in dioxane (15 mL), cyclohexene (5 mL, 49.4 mmol) and 250 mg of palladium on carbon (10 wt. % loading) were added and the mixture was heated at 100° C. under argon atmosphere for 3 hours. The mixture was cooled to room temperature and filtered through a celite pad, which was then washed with dioxane. The solvent was concentrated under reduced pressure and the resulting crude was purified by flash chromatography (eluant: dichloromethane/methanol/acetone/7N ammonia in methanol: 90/5/5/1) to afford 210 mg of the title compound (39%).

$^1$H NMR (DMSO-$d_6$) δ (ppm): 10.75 (s, 1H), 7.64 (dd, J=7.3, 1.3 Hz, 2H), 7.61 (d, J=8.5 Hz, 1H), 7.45 (t, J=7.4 Hz, 2H), 7.38 (t, J=7.3 Hz, 1H), 7.35 (d, J=2.4 Hz, 1H), 7.07 (dd, J=8.5, 2.4 Hz, 1H), 5.63 (s, 2H), 3.49 (t, J=6.2 Hz, 2H), 2.24 (br. s., 6H), 1.64 (br. s., 2H), 1.45 (br. s., 4H), 1.36 (br. s., 2H).

According to this same methodology, but employing suitably substituted starting material, the following compound was prepared:

6-Amino-3-phenyl-4-(3-piperidin-1-yl-propoxy)-2H-isoquinolin-1-one (cmpd. 40) (I, L=$CH_2$—$CH_2$—$CH_2$, R and $R_1$ together=piperidino, $R_2$=6-amino, $R_3$=H and $R_4$=phenyl)

$^1$H NMR (DMSO-$d_6$) δ (ppm): 10.54 (br. s., 1H), 7.88 (d, J=8.7 Hz, 1H), 7.63 (d, J=7.7 Hz, 2H), 7.46 (t, J=7.4 Hz, 2H), 7.41 (t, J=7.3 Hz, 1H), 6.79 (d, J=2.2 Hz, 1H), 6.74 (dd, J=8.7, 2.2 Hz, 1H), 5.97 (s, 2H), 3.45 (t, J=6.5 Hz, 2H), 2.16 (br. s., 4H), 2.12 (t, J=7.4 Hz, 2H), 1.61 (quin, J=6.9 Hz, 2H), 1.39 (quin, J=5.3 Hz, 4H), 1.26-1.36 (m, 2H).

Example 6

Conversion D

6-Chloro-3-phenyl-4-(3-piperidin-1-yl-propoxy)-2H-isoquinolin-1-one (cmpd. 41) (I, L=$CH_2$—$CH_2$—$CH_2$, R and $R_1$ together=piperidino, $R_2$=6-chloro, $R_3$=H and $R_4$=phenyl)

To a suspension of 34 mg (0.25 mmol) of copper(II) chloride in acetonitrile (1 mL), 37 L (0.316 mmol) of tert-butyl nitrite were added dropwise. The mixture was cooled with an ice bath and a suspension of 80 mg (0.21 mmol) of 6-amino-3-phenyl-4-(3-piperidin-1-yl-propoxy)-2H-isoquinolin-1-one (cmpd. 40) in acetonitrile (1.5 mL) was added. The reaction mixture was stirred at room temperature under argon atmosphere overnight and then worked-up with water and dichloromethane. The separated organic layer was once washed with sodium hydrogenocarbonate saturated solution, then concentrated under reduced pressure and the resulting crude was purified by flash chromatography (eluant: dichloromethane/methanol/acetone/7N ammonia in methanol: 90/5/5/1) to yield 32 mg of the title compound (38%).

$^1$H NMR (DMSO-$d_6$) δ (ppm): 11.37 (s, 1H), 8.22 (d, J=8.7 Hz, 1H), 7.84 (d, J=2.0 Hz, 1H), 7.67 (dd, J=8.0, 1.5 Hz, 2H), 7.57 (dd, J=8.5, 2.1 Hz, 1H), 7.43-7.54 (m, 3H), 3.51 (t, J=6.2 Hz, 2H), 2.20 (t, J=6.8 Hz, 6H), 1.61 (quin, J=6.6 Hz, 2H), 1.44 (quin, J=5.4 Hz, 4H), 1.28-1.38 (m, 2H)

6-Fluoro-3-phenyl-4-(3-piperidin-1-yl-propoxy)-2H-isoquinolin-1-one (cmpd. 42) (I, L=$CH_2$—$CH_2$—$CH_2$, R and $R_1$ together=piperidino, $R_2$=6-fluoro, $R_3$=H and $R_4$=phenyl)

To a suspension of 67 mg (0.57 mmol) of nitrosonium tetrafluoroborate in dichloromethane (1 mL), a suspension of 145 mg (0.38 mmol) of 6-amino-3-phenyl-4-(3-piperidin-1-yl-propoxy)-2H-isoquinolin-1-one (cmpd. 40) in dichloromethane (1 mL) was added at 0° C. under stirring and argon atmosphere. The reaction mixture was then stirred at room temperature overnight. 1,2-dichlorobenzene (1 mL) was added and the mixture was heated at 170° C. for 30 min. The solvent was concentrated under reduced pressure and the reaction was worked-up with water and dichloromethane. The separated organic layer was concentrated under reduced pressure and the resulting crude was purified by flash chromatography (eluant: dichloromethane/methanol/acetone/7N ammonia in methanol: 95/2/2/1) to yield 25 mg of the title compound (17%).

$^1$H NMR (DMSO-d$_6$) δ (ppm): 11.30 (s, 1H), 8.29 (dd, J=8.8, 5.9 Hz, 1H), 7.67 (dd, J=8.0, 1.5 Hz, 2H), 7.62 (dd, J=10.2, 2.5 Hz, 1H), 7.44-7.54 (m, 3H), 7.39 (td, J=8.8, 2.6 Hz, 1H), 3.51 (d, J=12.2 Hz, 2H), 2.22 (br. s., 6H), 1.63 (quin, J=6.6 Hz, 2H), 1.45 (quin, J=5.2 Hz, 4H), 1.29-1.40 (m, 2H).

Example 7

Conversion E 4-(2-Methylamino-ethoxy)-3-phenyl-2H-isoquinolin-1-one (cmpd. 16) (I, L=CH$_2$—CH$_2$, R=methyl, R$_1$=R$_2$=R$_3$=H and R$_4$=phenyl)

To a solution of 25 mg (0.079 mmol) of 4-(2-aminoethoxy)-3-phenyl-2H-isoquinolin-1-one hydrochloride (cmpd. 1) in formic acid (0.1 mL), 8 μL (0.08 mmol) of formaldehyde (37% in water) were added and the mixture was refluxed for 1 hour. The solvent was concentrated under reduced pressure and the resulting crude was purified by preparative HPLC affording 12 mg of the title compound (51%).

$^1$H NMR (DMSO-d$_6$) δ (ppm): 2.18 (s, 3H) 2.63 (t, 2H) 3.58 (t, J=5.43 Hz, 2H) 7.57 (ddd, 1H) 7.70 (dd, J=8.05, 1.46 Hz, 2H) 7.82 (ddd, J=8.14, 7.04, 1.28 Hz, 1H) 7.92 (d, J=7.80 Hz, 1H) 8.24 (ddd, J=8.05, 1.22, 0.40 Hz, 1H)

According to this same methodology, but employing suitably substituted starting material, the following compounds were prepared:

4-(2-Dimethylamino-ethoxy)-3-phenyl-2H-isoquinolin-1-one (cmpd. 17) (I, L=CH$_2$—CH$_2$, R=R$_1$=methyl, R$_2$=R$_3$=H and R$_4$=phenyl)

$^1$H NMR (DMSO-d$_6$) δ (ppm): 2.08 (s, 6H) 2.43 (br. s., 2H) 3.54 (t, J=5.73 Hz, 2H) 7.56 (ddd, J=8.02, 7.04, 1.16 Hz, 1H) 7.69 (dd, J=8.05, 1.46 Hz, 2H) 7.81 (ddd, J=8.14, 7.04, 1.28 Hz, 1H) 7.93 (d, J=7.80 Hz, 1H) 8.23 (ddd, J=8.05, 1.10, 0.50 Hz, 1H) 11.22 (s, 1H)

4-[2-(4-Methyl-piperazin-1-yl)-ethoxy]-3-phenyl-2H-isoquinolin-1-one dihydrochloride (cmpd. 19) (I, L=CH$_2$—CH$_2$, R$_2$=R$_3$=H, R and R$_1$ together=N-methyl-piperazino and R$_4$=phenyl)

$^1$H NMR (DMSO-d$_6$) δ (ppm): 2.78 (br. s., 3H) 7.49 (t, J=7.40 Hz, 1H) 7.53 (t, J=7.40 Hz, 2H) 7.59 (ddd, J=8.05, 7.13, 0.79 Hz, 1H) 7.69 (d, J=7.90 Hz, 2H) 7.84 (ddd, J=8.11, 7.13, 1.10 Hz, 1H) 7.96 (d, J=8.05 Hz, 1H) 8.25 (d, J=7.44 Hz, 1H) 11.29 (br. s., 1H).

4-[3-(4-Methyl-piperazin-1-yl)-propoxy]-3-phenyl-2H-isoquinolin-1-one dihydrochloride (cmpd. 20) (I, L=CH$_2$—CH$_2$—CH$_2$, R$_2$=R$_3$=H, R and R$_1$ together=N-methyl-piperazino and R$_4$=phenyl)

$^1$H NMR (DMSO-d$_6$) δ (ppm): 1.89 (br. s., 2H) 2.79 (br. s., 3H) 3.56 (t, J=5.85 Hz, 2H) 7.48 (t, J=7.40 Hz, 1H) 7.53 (t, J=7.50 Hz, 2H) 7.58 (ddd, J=8.02, 6.43, 1.89 Hz, 1H) 7.69 (d, J=7.70 Hz, 2H) 7.82 (td, J=8.05, 0.98 Hz, 1H) 7.85 (dd, J=8.05, 1.50 Hz, 1H) 8.25 (d, J=7.93 Hz, 1H) 11.27 (br. s., 1H).

Example 8

Conversion F

N-[3-(1-Oxo-3-phenyl-1,2-dihydro-isoquinolin-4-yloxy)-propyl]-acetamide (cmpd. 4) (I, L=CH$_2$—CH$_2$—CH$_2$, R=acetyl, R$_1$=R$_2$=R$_3$=H and R$_4$=phenyl)

To a solution of 150 mg (0.45 mmol) of 4-(2-aminoethoxy)-3-phenyl-2H-isoquinolin-1-one (cmpd. 1) dichloromethane (6 mL), triethylamine (190 L, 1.36 mmol) and acetyl chloride (39.3 L, 0.55 mmol) were added under argon atmosphere at 0° C. and the mixture was stirred at room temperature overnight. The reaction mixture was then washed with water, the layers were separated and the aqueous layer was extracted with dichloromethane. The combined organic layers were dried over sodium sulfate, concentrated under reduced pressure and the resulting crude was purified by flash chromatography (dichloromethane:methanol, 97:3) affording 64 mg of the title compound (42%).

$^1$H NMR (DMSO-d$_6$) δ (ppm): 2.18 (s, 3H) 2.63 (t, 2H) 3.58 (t, J=5.43 Hz, 2H) 7.57 (ddd, 1H) 7.70 (dd, J=8.05, 1.46 Hz, 2H) 7.82 (ddd, J=8.14, 7.04, 1.28 Hz, 1H) 7.92 (d, J=7.80 Hz, 1H) 8.24 (ddd, J=8.05, 1.22, 0.40 Hz, 1H).

According to this same methodology, but employing suitably substituted starting material, the following compounds were prepared:

N-[2-(1-Oxo-3-phenyl-1,2-dihydro-isoquinolin-4-yloxy)-ethyl]-acetamide (cmpd. 2) (I, L=CH$_2$—CH$_2$, R=acetyl, R$_1$=R$_2$=R$_3$=H and R$_4$=phenyl)

$^1$H NMR (DMSO-d$_6$) δ (ppm): 1.78 (s, 3H) 3.19 (q, J=5.70 Hz, 2H) 3.46 (t, J=5.61 Hz, 2H) 7.56 (ddd, 1H) 7.81 (ddd, J=8.29, 7.02, 1.30 Hz, 1H) 7.88 (ddd, J=8.29, 0.91, 0.51 Hz, 1H) 7.94 (t, J=5.67 Hz, 1H) 8.24 (ddd, J=8.05, 1.22, 0.49 Hz, 1H) 11.22 (s, 1H).

4-[2-(4-Acetyl-piperazin-1-yl)-ethoxy]-3-phenyl-2H-isoquinolin-1-one (cmpd. 7) (I, L=CH$_2$—CH$_2$, R$_2$=R$_3$=H, R and R$_1$ together=N-acetyl-piperazino and R$_4$=phenyl)

$^1$H NMR (DMSO-d$_6$) δ (ppm): 1.98 (s, 3H) 2.20 (t, J=4.69 Hz, 2H) 2.27 (t, J=4.40 Hz, 2H) 2.49 (t, J=5.25 Hz, 2H) 3.58 (t, J=5.30 Hz, 1H) 7.57 (ddd, J=7.95, 7.10, 0.67 Hz, 1H) 7.69 (dd, J=8.11, 1.40 Hz, 2H) 7.83 (ddd, J=8.14, 7.10, 1.22 Hz, 1H) 8.00 (d, J=8.05 Hz, 1H) 8.24 (d, J=7.56 Hz, 1H) 11.22 (s, 1H).

N-[3-(1-Oxo-3-phenyl-1,2-dihydro-isoquinolin-4-yloxy)-propyl]-benzamide (cmpd. 8) (I, L=CH$_2$—CH$_2$—CH$_2$, R=benzoyl, R$_1$=R$_2$=R$_3$=H and R$_4$=phenyl)

$^1$H NMR (DMSO-d$_6$) δ (ppm): 1.78 (quin, J=6.64 Hz, 2H) 3.26 (q, J=6.50 Hz, 2H) 3.56 (t, J=6.28 Hz, 2H) 7.55 (ddd, J=8.01, 7.04, 1.04 Hz, 1H) 7.69 (d, J=7.80 Hz, 2H) 7.86 (d, J=7.90 Hz, 1H) 8.23 (ddd, J=7.98, 1.20, 0.60 Hz, 1H) 8.32 (t, J=5.42 Hz, 1H) 11.22 (s, 1H).

Preparation of 7-fluoro-4-(2-hydroxyethoxy)-3-phenylisoquinolin-1(2H)-one

To a solution of 590 mg (1.54 mmol) of 7-fluoro-3-phenyl-4-[2-(tetrahydro-2H-pyran-2-yloxy)ethoxy]isoquinolin-1 (2H)-one in methanol (12 mL), 88 mg of p-toluenesuphonic acid (0.46 mmol) were added and the resulting mixture was heated at 55° C. for 2 hours. The solvent was removed under reduced pressure and the residue was diluted with dichloromethane and washed twice with aqueous sodium hydrogencarbonate saturated solution. The combined organic layer were dried over sodium sulphate and concentrated under reduced pressure to afford 438 mg of the title compound (95%).

$^1$H NMR (DMSO-$d_6$) δ (ppm): 11.36 (s, 1H), 8.08 (dd, J=5.25, 8.91 Hz, 1H), 7.89 (dd, J=2.75, 9.34 Hz, 1H), 7.66-7.74 (m, 3H), 7.41-7.54 (m, 3H), 4.47 (t, J=2.50 Hz, 1H).

Preparation of 7-fluoro-4-(2-iodoethoxy)-3-phenylisoquinolin-1(2H)-one To a solution of 100 mg (0.33 mmol) of 7-fluoro-4-(2-hydroxyethoxy)-3-phenylisoquinolin-1(2H)-one in acetonitrile (10 mL), 350 mg (1.33 mmol) of triphenylphosphine, 90 mg (1.33 mmol) of imidazole and 251 mg (0.99 mmol) of iodide were added and the mixture was stirred at room temperature for 18 hours under argon. The mixture was filtered over celite and the filtrate was concentrated under reduce pressure. Purification of the residue by flash chromatography (hexane/ethyl acetate: 6/4) afforded 57 mg of the title compound (42%).

$^1$H NMR (DMSO-$d_6$) δ (ppm): 11.41 (s, 1H), 8.06 (dd, J=5.13, 9.03 Hz, 1H), 7.90 (dd, J=2.62, 9.34 Hz, 1H), 7.64-7.76 (m, 3H), 7.43-7.56 (m, 4H), 3.70 (t, J=6.16 Hz, 2H), 3.22-3.27 (m, 2H).

Example 9

Step i

2-Methylamino-N-(6-oxo-5,6-dihydro-phenanthridin-2-yl)-acetamide

To a stirred suspension of 150 mg of 2-chloro-N-(6-oxo-5,6-dihydro-phenanthridin-2-yl)-acetamide (XV) (0.52 mmol) in N,N-dimethylformamide (1.4 mL), 9 mL of a 33% solution of methylamine in ethanol were added (mM). The reaction mixture was stirred at room temperature for 3 hours. The ethanol was then evaporated under reduced pressure and the mixture was diluted with diethyl ether and filtered. A light-yellow solid was then collected, washed with ether then with cold water and dried. The title compound was obtained in moderate yield (100 mg, 68%).

$^1$H NMR (DMSO-$d_6$) δ (ppm): 11.68 (s, 1H), 10.33 (br. s., 1H), 8.61 (d, J=2.1 Hz, 1H), 8.34 (dd, J=7.9, 1.1 Hz, 1H), 8.26 (d, J=8.2 Hz, 1H), 7.89 (ddd, J=8.2, 7.1, 1.4 Hz, 1H), 7.70 (dd, J=8.7, 2.2 Hz, 1H), 7.67 (ddd, J=7.9, 7.2, 0.7 Hz, 1H), 7.35 (d, J=8.8 Hz, 1H), 3.68 (s, 2H), 2.54 (s, 3H).

Step ia (3-{[(6-Oxo-5,6-dihydro-phenanthridin-2-ylcarbamoyl)-methyl]-amino}-propyl)-carbamic acid tert-butyl ester To a stirred suspension of 50 mg of 2-chloro-N-(6-oxo-5, 6-dihydro-phenanthridin-2-yl)-acetamide (XV) (0.17 mmol) in N,N-dimethylformamide (3 mL), 0.09 mL of (3-aminopropyl)-carbamic acid tert-butyl ester (0.51 mmol) and 0.036 mL of triethylamine (0.26 mmol) were added. The reaction mixture was stirred at room temperature overnight, evaporated to dryness and then purified through preparative HPLC on a Waters X Terra RP 18 (19×250 mm, 5 m) column. Mobile phase A was 0.05% ammonia/acetonitrile:95/5 and mobile phase B was acetonitrile/water:95/5. Gradient from 10 to 75% B in 15 min. Fractions containing the desired compound were dried, affording 32 mg (44% yield) of the title compound.

$^1$H NMR (DMSO-$d_6$) δ (ppm): 11.65 (s, 1H), 10.09 (br. s., 1H), 8.63 (d, J=2.0 Hz, 1H), 8.33 (dd, J=7.9, 1.2 Hz, 1H), 8.28 (d, J=8.2 Hz, 1H), 8.12-8.12 (m, 1H), 7.88 (ddd, J=8.2, 7.1, 1.4 Hz, 1H), 7.72 (dd, J=8.8, 2.0 Hz, 1H), 7.66 (ddd, J=8.0, 7.1, 0.7 Hz, 1H), 7.33 (d, J=8.8 Hz, 1H), 6.83 (t, J=5.7 Hz, 1H), 3.47 (br. s., 2H), 3.02 (q, J=6.8 Hz, 2H), 2.68 (t, J=7.3 Hz, 2H), 1.63 (quin, J=6.9 Hz, 2H), 1.37 (s, 9H).

(6-{[(6-Oxo-5,6-dihydro-phenanthridin-2-ylcarbamoyl)-methyl]-amino}-hexyl)-carbamic acid tert-butyl ester To a stirred suspension of 65 mg of 2-chloro-N-(6-oxo-5, 6-dihydro-phenanthridin-2-yl)-acetamide (XV) (0.23 mmol) in N,N-dimethylformamide (2 mL), 175 mg of (6-aminohexyl)-carbamic acid tert-butyl ester hydrochloride (0.69 mmol) and 0.097 mL of triethylamine (0.69 mmol) were added. The reaction mixture was stirred at room temperature overnight, diluted with dichloromethane, and the resulting solution was washed first with water then with brine, dried over sodium sulfate and evaporated to dryness. The crude was purified by preparative HPLC on Waters X Terra RP 18 (19×250 mm, 5 m) column. Mobile phase A was 0.05% ammonia/acetonitrile:95/5 and mobile phase B was acetonitrile/water:95/5. Gradient from 10 to 75% B in 15 min. Fractions containing the desired compound were dried, affording 50 mg (47% yield) of the title compound.

$^1$H NMR (DMSO-$d_6$) δ (ppm): 11.62 (br. s., 1H), 9.90 (br. s., 1H), 8.65 (d, J=1.7 Hz, 1H), 8.33 (dd, J=8.5, 1.2 Hz, 1H), 8.30 (d, J=8.0 Hz, 1H), 7.88 (ddd, J=8.3, 7.1, 1.1 Hz, 1H), 7.74 (dd, J=8.7, 1.9 Hz, 1H), 7.65 (t, J=7.6 Hz, 1H), 7.31 (d, J=8.7 Hz, 1H), 6.73 (t, J=5.5 Hz, 1H), 3.27-3.33 (m, 2H), 2.89 (q, J=6.5 Hz, 2H), 2.55 (t, J=7.0 Hz, 2H), 1.97-2.61 (m, 1H), 1.17-1.51 (m, 8H), 1.36 (s, 9H).

Step ib 2-(3-Amino-propylamino)-N-(6-oxo-5,6-dihydrophenanthridin-2-yl)-acetamide hydrochloride 32 mg of (3-{[(6-oxo-5,6-dihydro-phenanthridin-2-ylcarbamoyl)-methyl]-amino}-propyl)-carbamic acid tert-butyl ester (0.075 mmol) were dissolved in dichloromethane (1 mL) and 4N hydrochloric acid in dioxane (1 mL) was added. The reaction mixture was stirred at room temperature overnight and then evaporated, affording 32 mg (97% yield) of the title compound.

$^1$H NMR (DMSO-$d_6$) δ (ppm): 11.72 (s, 1H), 10.90 (s, 1H), 9.29 (d, J=0.6 Hz, 2H), 8.62 (d, J=2.0 Hz, 1H), 8.35 (dd, J=7.9, 1.2 Hz, 1H), 8.22 (d, J=8.2 Hz, 1H), 7.98 (br. s., 3H), 7.91 (ddd, J=8.2, 7.1, 1.3 Hz, 1H), 7.69 (dd, J=8.8, 2.2 Hz, 1H), 7.68 (ddd, J=7.9, 7.2, 0.9 Hz, 1H), 7.38 (d, J=8.8 Hz, 1H), 4.00 (t, J=4.5 Hz, 2H), 3.11 (br. s., 2H), 2.92 (sxt, J=6.4 Hz, 2H), 2.00 (quin, J=7.6 Hz, 2H).

2-(6-Amino-hexylamino)-N-(6-oxo-5,6-dihydro-phenanthridin-2-yl)-acetamide trifluoroacetate 45 mg of (6-{[(6-oxo-5,6-dihydro-phenanthridin-2-ylcarbamoyl)-methyl]-amino}-hexyl)-carbamic acid tert-butyl ester (0.097 mmol) were dissolved in dichloromethane (5 mL) and trifluoroacetic acid (1.5 mL) was added. The reaction mixture was stirred at room temperature overnight, evaporated, taken up with diethyl ether, filtered and the collected solid was dried under vacuum to afford 30 mg (65% yield) of the title compound as a light-yellow solid.

$^1$H NMR (DMSO-$d_6$) δ (ppm): 11.72 (s, 1H), 10.67 (s, 1H), 8.93 (dt, J=10.7, 5.4 Hz, 2H), 8.58 (d, J=2.1 Hz, 1H), 8.35 (dd, J=8.1, 1.2 Hz, 1H), 8.22 (d, J=8.2 Hz, 1H), 7.91 (ddd, J=8.2, 7.1, 1.4 Hz, 1H), 7.69 (ddd, J=7.9, 7.2, 0.7 Hz, 1H), 7.65 (dd, J=9.0, 2.3 Hz, 1H), 7.67 (br. s., 3H), 7.38 (d, J=8.7 Hz, 1H), 3.99 (t, J=5.4 Hz, 2H), 2.95-3.06 (m, 2H), 2.72-2.85 (m, 2H), 1.64 (quin, J=7.1 Hz, 2H), 1.53 (quin, J=7.0 Hz, 2H), 1.33 (dt, J=6.9, 3.4 Hz, 4H).

Step ii

9-Dimethylamino-11,11-dimethyl-1-(3-{methyl-[(6-oxo-5,6-dihydro-phenanthridin-2-ylcarbamoyl)-methyl]-carbamoyl}-propyl)-2,3,4,11-tetrahydro-naphtho[2,3-g]quinolinium trifluoroacetate (cmpd. P1, $X^-$=$CF_3CO_2^-$, $R_{13}$=methyl, m=0)

To a stirred solution of 3.65 mg of 2-methylamino-N-(6-oxo-5,6-dihydro-phenanthridin-2-yl)-acetamide (0.013 mmol) in N,N-dimethylformamide (0.3 mL), 0.0067 mL of diisopropylethylamine (0.039 mmol) and 5 mg of ATTO 610 NHS ester perchlorate (XVIII) (0.0085 mmol) were added under nitrogen, and the reaction was stirred at room temperature for 3 hours. The mixture was then evaporated, and the resulting crude was purified by preparative HPLC on Hypersil (21×250 mm, 5 μm) column. Mobile phase A was 0.1% trifluoroacetic acid/acetonitrile:95/5 and mobile phase B was acetonitrile/water:95/5. Gradient from 0 to 70% B in 20 min. Fractions containing the desired compound were dried, affording 1.6 mg of the title compound.

MS calculated: 654.3444. MS found: 654.3447.
ESI(+) MS: m/z 654 (M$^+$).

According to this same methodology, but employing the suitable starting materials, the following compounds were prepared:

9-Dimethylamino-11,11-dimethyl-1-[3-(3-{[(6-oxo-5,6-dihydro-phenanthridin-2-ylcarbamoyl)-methyl]-amino}-propylcarbamoyl)-propyl]-2,3,4,11-tetrahydro-naphtho[2,3-g]quinolinium trifluoroacetate (cmpd. P2, $X^-$=$CF_3CO_2^-$, $R_{13}$=H, m=1, B=$(CH_2)_3$—NH—)

MS calculated: 697.3866. MS found: 697.3864.
ESI(+) MS: m/z 697 (M$^+$).

9-Dimethylamino-11,11-dimethyl-1-[3-(6-{[(6-oxo-5,6-dihydro-phenanthridin-2-ylcarbamoyl)-methyl]-amino}-hexylcarbamoyl)-propyl]-2,3,4,11-tetrahydro-naphtho[2,3-g]quinolinium trifluoroacetate (cmpd. P3, $X^-$=$CF_3CO_2^-$, $R_{13}$=H, m=1, B=$(CH_2)_6$—NH—)

MS calculated: 739.4337. MS found: 739.4333.
ESI(+) MS: m/z 739 (M$^+$).

The invention claimed is:
1. A compound of formula (I):

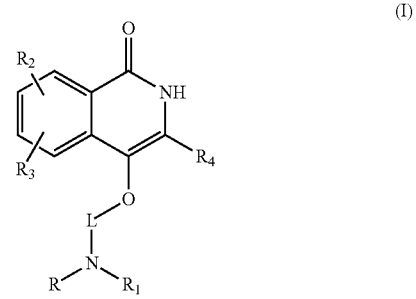

wherein L is an optionally substituted linear or branched $C_2$-$C_6$ alkyl, $C_3$-$C_7$ cycloalkyl group or, by including the nitrogen atom to which it is bonded, an optionally substituted heterocyclyl or heterocyclyl $C_1$-$C_6$ alkyl;

R and $R_1$ are independently hydrogen atom, an optionally substituted linear or branched $C_1$-$C_6$ alkyl, $C_3$-$C_7$ cycloalkyl, heterocyclyl, aryl, heteroaryl or $COR_5$ group or, taken together with the nitrogen atom to which they are bonded, form an optionally substituted heterocyclyl or heteroaryl group;

$R_2$ and $R_3$ are independently hydrogen or halogen atom; a cyano, nitro, $NHCOR_5$, $COR_5$, $NR_6R_7$, $NR_6COR_5$, $OR_8$, $SR_8$, $SOR_{11}$, $SO_2R_{11}$, $NHSOR_{11}$, $NHSO_2R_{11}$, $R_9R_{10}N$—$C_1$-$C_6$ alkyl, $R_9O$—$C_1$-$C_6$ alkyl group, or an optionally substituted linear or branched $C_1$-$C_6$ alkyl, $C_2$-$C_6$ alkenyl, $C_2$-$C_6$ alkynyl, $C_3$-$C_7$ cycloalkyl, heterocyclyl, aryl, or heteroaryl group;

$R_4$ is an optionally substituted linear or branched $C_1$-$C_6$ alkyl, $C_3$-$C_7$ cycloalkyl, $C_2$-$C_6$ alkenyl, $C_2$-$C_6$ alkynyl, aryl, aryl $C_1$-$C_6$ alkyl, aryl $C_3$-$C_7$ cycloalkyl, aryl $C_2$-$C_6$ alkenyl, aryl $C_2$-$C_6$ alkynyl, heterocyclyl, heterocyclyl $C_1$-$C_6$ alkyl, heterocyclyl $C_3$-$C_7$ cycloalkyl, heterocyclyl $C_2$-$C_6$ alkenyl, heterocyclyl $C_2$-$C_6$ alkynyl, heteroaryl, heteroaryl $C_1$-$C_6$ alkyl, heteroaryl $C_3$-$C_7$ cycloalkyl, heteroaryl $C_2$-$C_6$ alkenyl, heteroaryl $C_2$-$C_6$ alkynyl;

$R_5$ is hydrogen atom or $NR_6R_8$, $OR_8$, $SR_8$, $R_9R_{10}N$—$C_1$-$C_6$ alkyl, $R_9O$—$C_1$-$C_6$ alkyl, or an optionally substituted linear or branched $C_1$-$C_6$ alkyl, $C_2$-$C_6$ alkenyl, $C_2$-$C_6$ alkynyl, $C_3$-$C_7$ cycloalkyl, heterocyclyl, aryl or heteroaryl group;

$R_6$ and $R_7$ are independently hydrogen atom, an optionally substituted linear or branched $C_1$-$C_6$ alkyl, $C_2$-$C_6$ alkenyl, $C_2$-$C_6$ alkynyl, $C_3$-$C_7$ cycloalkyl, $R_9R_{10}N$—$C_2$-$C_6$ alkyl, $R_9O$—$C_2$-$C_6$ alkyl, heterocyclyl, aryl or heteroaryl group, or $R_6$ and $R_7$, taken together with the nitrogen atom to which they are bonded, may form an optionally substituted heterocyclyl group;

$R_8$ is hydrogen, a $COR_6$, $SOR_{11}$, $SO_2R_{11}$, $R_9R_{10}N$—$C_2$-$C_6$ alkyl or $R_9O$—$C_2$-$C_6$ alkyl group, or an optionally substituted linear or branched $C_1$-$C_6$ alkyl, $C_2$-$C_6$ alkenyl, $C_2$-$C_6$ alkynyl, $C_3$-$C_7$ cycloalkyl, heterocyclyl, aryl or heteroaryl group, wherein $R_6$ is as defined above;

$R_9$ and $R_{10}$ are independently hydrogen, $COR_5$, or an optionally substituted linear or branched $C_1$-$C_6$ alkyl, $C_2$-$C_6$ alkenyl, $C_7$-$C_6$ alkynyl, $C_3$-$C_7$ cycloalkyl, heterocyclyl, aryl or heteroaryl group, or $R_9$ and $R_{10}$, taken together with the nitrogen atom to which they are bonded, may form an optionally substituted heterocyclyl group, wherein $R_5$ is as defined above;

$R_{11}$ is hydrogen atom, $NR_6R_7$, $OR_8$, $R_9R_{10}N$—$C_1$-$C_6$ alkyl, $R_9O$—$C_1$-$C_6$ alkyl, or an optionally substituted linear or branched $C_1$-$C_6$ alkyl, $C_2$-$C_6$ alkenyl, $C_2$-$C_6$ alkynyl, $C_3$-$C_7$ cycloalkyl, heterocyclyl, aryl or heteroaryl group, wherein $R_6$, $R_7$, $R_8$, $R_9$ and $R_{10}$ are as defined above;

or a pharmaceutically acceptable salt thereof.

2. The compound according to claim 1, wherein L represents an optionally substituted linear or branched $C_2$-$C_6$ alkyl or, by including the nitrogen atom to which it is bonded, an optionally substituted heterocyclyl or heterocyclyl $C_1$-$C_6$ alkyl;

R and $R_1$ are independently hydrogen atom, an optionally substituted linear or branched $C_1$-$C_6$ alkyl or $COR_5$ group or, taken together with the nitrogen atom to which they are bonded, form an optionally substituted heterocyclyl or heteroaryl group;

$R_2$ and $R_3$ are independently hydrogen or halogen atom; a nitro, amino, hydroxy, $COR_5$, or an optionally substituted linear or branched $C_1$-$C_6$ alkyl group;

$R_4$ is an optionally substituted aryl or heteroaryl group;

$R_5$ is an optionally substituted linear or branched $C_1$-$C_6$ alkyl;

or a pharmaceutically acceptable salt thereof.

3. The compound according to claim 2, wherein L represents an optionally substituted linear or branched $C_2$-$C_4$ alkyl group or, by including the nitrogen atom to which it is bonded, an optionally substituted heterocyclyl;

R and $R_1$ are independently hydrogen atom, an optionally substituted linear or branched $C_1$-$C_4$ alkyl or $COR_5$ group or, taken together with the nitrogen atom to which they are bonded, form an optionally substituted piperidinyl, pyrrolidinyl, piperazinyl, or pyrrolyl group;

$R_2$ and $R_3$ are independently hydrogen, chlorine or fluorine atom; or a nitro, amino, hydroxy, $COR_5$, or an optionally substituted linear or branched $C_1$-$C_4$ alkyl group;

$R_4$ is an optionally substituted phenyl or thienyl group;

$R_5$ is an optionally substituted linear or branched $C_1$-$C_4$ alkyl group;

or a pharmaceutically acceptable salt thereof.

4. The compound according to claim 1, selected from the group consisting of:

4-(2-Amino-ethoxy)-3-phenyl-2H-isoquinolin-1-one,
N-[2-(1-Oxo-3-phenyl-1,2-dihydro-isoquinolin-4-yloxy)-ethyl]-acetamide,
4-(3-Amino-propoxy)-3-phenyl-2H-isoquinolin-1-one,
N-[3-(1-Oxo-3-phenyl-1,2-dihydro-isoquinolin-4-yloxy)-propyl]-acetamide,
3-Phenyl-4-(3-piperidin-1-yl-propoxy)-2H-isoquinolin-1-one,
3-Phenyl-4-(2-piperazin-1-yl-ethoxy)-2H-isoquinolin-1-one,
4-[2-(4-Acetyl-piperazin-1-yl)-ethoxy]-3-phenyl-2H-isoquinolin-1-one,
N-[3-(1-Oxo-3-phenyl-1,2-dihydro-isoquinolin-4-yloxy)-propyl]-benzamide,
3-(3-Methoxy-phenyl)-4-(2-piperidin-1-yl-ethoxy)-2H-isoquinolin-1-one,
3-(3-Methoxy-phenyl)-4-(3-piperidin-1-yl-propoxy)-2H-isoquinolin-1-one,
4-(2-Amino-ethoxy)-3-(3-methoxy-phenyl)-2H-isoquinolin-1-one,
4-(3-Methylamino-propoxy)-3-phenyl-2H-isoquinolin-1-one,
3-Phenyl-4-(2-pyrrol-1-yl-ethoxy)-2H-isoquinolin-1-one,
3-Phenyl-4-(3-piperazin-1-yl-propoxy)-2H-isoquinolin-1-one,
3-Phenyl-4-(3-pyrrol-1-yl-propoxy)-2H-isoquinolin-1-one,
4-(2-Methylamino-ethoxy)-3-phenyl-2H-isoquinolin-1-one,
4-(2-Dimethylamino-ethoxy)-3-phenyl-2H-isoquinolin-1-one,
4-(3-Diethylamino-propoxy)-3-phenyl-2H-isoquinolin-1-one,
4-[2-(4-Methyl-piperazin-1-yl)-ethoxy]-3-phenyl-2H-isoquinolin-1-one,
4-[3-(4-Methyl-piperazin-1-yl)-propoxy]-3-phenyl-2H-isoquinolin-1-one,
3-Phenyl-4-(3-pyrrolidin-1-yl-propoxy)-2H-isoquinolin-1-one,
4-(4-Amino-butoxy)-3-phenyl-2H-isoquinolin-1-one,
3-(4-Methoxy-phenyl)-4-(3-piperidin-1-yl-propoxy)-2H-isoquinolin-1-one,
4-(2-Amino-ethoxy)-3-(4-methoxy-phenyl)-2H-isoquinolin-1-one,
4-(2-Amino-ethoxy)-7-fluoro-3-(4-methoxy-phenyl)-2H-isoquinolin-1-one,
4-(2-Amino-ethoxy)-3-(4-hydroxy-phenyl)-2H-isoquinolin-1-one,
3-(4-Hydroxy-phenyl)-4-(3-piperidin-1-yl-propoxy)-2H-isoquinolin-1-one,
4-(2-Amino-ethoxy)-7-fluoro-3-(4-hydroxy-phenyl)-2H-isoquinolin-1-one,
4-(2-Amino-ethoxy)-3-thiophen-3-yl-2H-isoquinolin-1-one,
7-Acetyl-3-phenyl-4-(2-piperidin-1-yl-ethoxy)-2H-isoquinolin-1-one,
6-Nitro-3-phenyl-4-(2-piperidin-1-yl-ethoxy)-2H-isoquinolin-1-one,
4-(2-Amino-ethoxy)-3-(3-hydroxy-phenyl)-2H-isoquinolin-1-one,
3-(3-Hydroxy-phenyl)-4-(3-piperidin-1-yl-propoxy)-2H-isoquinolin-1-one,
6-Nitro-3-phenyl-4-(3-piperidin-1-yl-propoxy)-2H-isoquinolin-1-one,
7-Nitro-3-phenyl-4-(3-piperidin-1-yl-propoxy)-2H-isoquinolin-1-one,
7-Amino-3-phenyl-4-(3-piperidin-1-yl-propoxy)-2H-isoquinolin-1-one,
7-Chloro-3-phenyl-4-(3-piperidin-1-yl-propoxy)-2H-isoquinolin-1-one,
7-Fluoro-3-phenyl-4-(3-piperidin-1-yl-propoxy)-2H-isoquinolin-1-one,
4-(2-Amino-ethoxy)-7-fluoro-3-phenyl-2H-isoquinolin-1-one,
6-Amino-3-phenyl-4-(3-piperidin-1-yl-propoxy)-2H-isoquinolin-1-one,
6-Chloro-3-phenyl-4-(3-piperidin-1-yl-propoxy)-2H-isoquinolin-1-one,
6-Fluoro-3-phenyl-4-(3-piperidin-1-yl-propoxy)-2H-isoquinolin-1-one,
7-Fluoro-3-(3-methoxy-phenyl)-4-(3-piperidin-1-yl-propoxy)-2H-isoquinolin-1-one,
3-(3-Chloro-phenyl)-4-(3-piperidin-1-yl-propoxy)-2H-isoquinolin-1-one,
7-Fluoro-3-(3-hydroxy-phenyl)-4-(3-piperidin-1-yl-propoxy)-2H-isoquinolin-1-one,
4-(2-Amino-ethoxy)-7-fluoro-3-(3-methoxy-phenyl)-2H-isoquinolin-1-one,
4-(2-Amino-ethoxy)-7-fluoro-3-(3-hydroxy-phenyl)-2H-isoquinolin-1-one,
4-(2-Amino-ethoxy)-3-(3-chloro-phenyl)-2H-isoquinolin-1-one, 4-(2-Amino-ethoxy)-5-methyl-3-phenyl-2H-isoquinolin-1-one,
4-(2-Amino-ethoxy)-3-(3-chloro-phenyl)-7-fluoro-2H-isoquinolin-1-one,
3-Phenyl-4-(2-piperidin-1-yl-ethoxy)-2H-isoquinolin-1-one,
4-(2-Diethylamino-ethoxy)-3-phenyl-2H-isoquinolin-1-one,
3-Phenyl-4-(2-pyrrolidin-1-yl-ethoxy)-2H-isoquinolin-1-one,
4-(2-Morpholin-4-yl-ethoxy)-3-phenyl-2H-isoquinolin-1-one,
5-Methyl-3-phenyl-4-(3-piperidin-1-yl-propoxy)-2H-isoquinolin-1-one,
4-(2-Amino-ethoxy)-7-fluoro-5-methyl-3-phenyl-2H-isoquinolin-1-one
7-Fluoro-5-methyl-3-phenyl-4-(3-piperidin-1-yl-propoxy)-2H-isoquinolin-1-one,
4-(2-Amino-ethoxy)-3-(3-chlor)-phenyl)-5-methyl-2H-isoquinolin-1-one,
3-(3-Chloro-phenyl)-5-methyl-4-(3-piperidin-1-yl-propoxy)-2H-isoquinolin-1-one,
4-(2-Amino-ethoxy)-3-(3-chloro-phenyl)-7-fluoro-5-methyl-2H-isoquinolin-1-one,
3-(3-Chloro-phenyl)-7-fluoro-5-methyl-4-(3-piperidin-1-yl-propoxy)-2H-isoquinolin-1-one,
4-(2-Amino-ethoxy)-7-fluoro-3-(4-methoxy-phenyl)-5-methyl-2H-isoquinolin-1-one,
7-Fluoro-3-(4-methoxy-phenyl)-5-methyl-4-(3-piperidin-1-yl-propoxy)-2H-isoquinolin-1-one,
4-(2-Amino-ethoxy)-7-fluoro-3-(3-methoxy-phenyl)-5-methyl-2H-isoquinolin-1-one,
7-Fluoro-3-(3-methoxy-phenyl)-5-methyl-4-(3-piperidin-1-yl-propoxy)-2H-isoquinolin-1-one,
4-(2-Amino-ethoxy)-3-(4-chloro-3-methoxy-phenyl)-7-fluoro-5-methyl-2H-isoquinolin-1-one,
3-(4-Chloro-3-methoxy-phenyl)-7-fluoro-5-methyl-4-(3-piperidin-1-yl-propoxy)-2H-isoquinolin-1-one,
4-(2-Amino-ethoxy)-3-(3-chloro-4-methoxy-phenyl)-7-fluoro-5-methyl-2H-isoquinolin-1-one,
3-(3-Chloro-4-methoxy-phenyl)-7-fluoro-5-methyl-4-(3-piperidin-1-yl-propoxy)-2H-isoquinolin-1-one,
4-(2-Amino-ethoxy)-3-(3-chloro-4-methoxy-phenyl)-5-methyl-2H-isoquinolin-1-one,
3-(3-Chloro-4-methoxy-phenyl)-5-methyl-4-(3-piperidin-1-yl-propoxy)-2H-isoquinolin-1-one,
4-(2-Amino-ethoxy)-3-(4-chloro-3-methoxy-phenyl)-5-methyl-2H-isoquinolin-1-one,
3-(4-(Chloro-3-methoxy-phenyl)-5-methyl-4-(3-piperidin-1-yl-propoxy)-2H-isoquinolin-1-one,
4-(2-Amino-ethoxy)-3-(3-methoxy-phenyl)-5-methyl-2H-isoquinolin-1-one,
3-(3-Methoxy-phenyl)-5-methyl-4-(3-piperidin-1-yl-propoxy)-2H-isoquinolin-1-one,
4-(2-Amino-ethoxy)-3-(4-methoxy-phenyl)-5-methyl-2H-isoquinolin-1-one,
3-(4-Methoxy-phenyl)-5-methyl-4-(3-piperidin-1-yl-propoxy)-2H-isoquinolin-1-one,
4-(2-Amino-ethoxy)-7-fluoro-3-(4-phenoxy-phenyl)-2H-isoquinolin-1-one,
7-Fluoro-3-(4-phenoxy-phenyl)-4-(3-piperidin-1-yl-propoxy)-2H-isoquinolin-1-one,
4-(2-Amino-ethoxy)-3-benzyl-7-fluoro-2H-isoquinolin-1-one,
3-Benzyl-7-fluoro-4-(3-piperidin-1-yl-propoxy)-2H-isoquinolin-1-one,
4-(2-Amino-ethoxy)-8-fluoro-3-phenyl-2H-isoquinolin-1-one,
8-Fluoro-3-phenyl-4-(3-piperidin-1-yl-propoxy)-2H-isoquinolin-1-one,
4-[2-(dimethylamino)ethoxy]-7-fluoro-3-phenylisoquinolin-1(2H)-one,
7-fluoro-3-phenyl-4-(piperidin-4-yloxy)isoquinolin-1(2H)-one,
4-(3-aminopropoxy)-7-fluoro-3-phenylisoquinolin-1(2H)-one,
4-[3-(benzylamino)propoxy]-7-fluoro-3-phenylisoquinolin-1(2H)-one,
4-[2-(diethylamino)ethoxy]-7-fluoro-3-phenylisoquinolin-1(2H)-one,
7-fluoro-4-[2-(4-methylpiperazin-1-yl)ethoxy]-3-phenylisoquinolin-1(2H)-one and
7-fluoro-3-phenyl-4-[2-(phenylamino)ethoxy]isoquinolin-1(2H)-one.

5. A process for the preparation of compounds of formula (I) as defined in claim 1, which process comprises:

either step 1) alkylating a compound of formula (III):

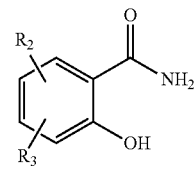

wherein $R_2$ and $R_3$ are as defined in claim 1, with a compound of formula (IV):

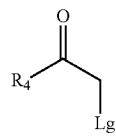

wherein $R_4$ is as defined in claim 1 and Lg represents a suitable leaving group;

step 2) cyclodehydrating the resultant compound of formula (V):

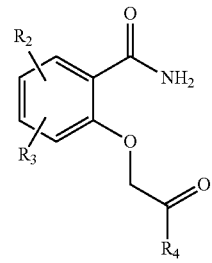

wherein $R_2$, $R_3$ and $R_4$ are as defined above;

step 3) rearranging the resultant compound of formula (VI):

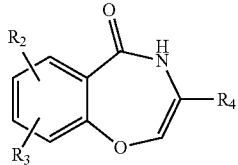

VI wherein $R_2$, $R_3$ and $R_4$ are as defined above, so as to obtain a compound of formula (VII):

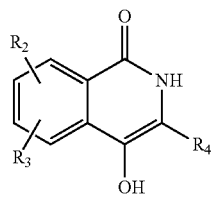

VII wherein $R_2$, $R_3$ and $R_4$ are as defined above;
or
step 4) reacting a compound of formula (VIII) with compound of formula (IX):

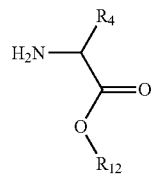

VIII

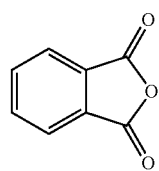

IX wherein $R_4$ is as defined above and $R_{12}$ is a $C_1$-$C_6$ alkyl or an aryl $C_1$-$C_6$ alkyl group,
step 3a) rearranging the resultant compound of formula (X):

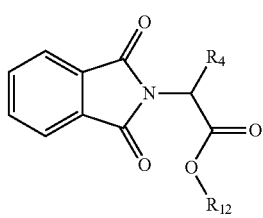

X wherein $R_4$ and $R_{12}$ is as defined above, so as to obtain a compound of formula (VII) as above defined wherein $R_2$ and $R_3$ are both hydrogen atoms;
and
step 5) alkylating a compound of formula (VII) as defined above with
either a compound of formula (XI):

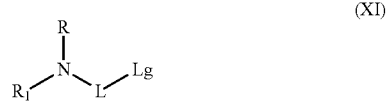

(XI)

wherein L is as defined in claim 1 and R, $R_1$, and Lg are as defined above, so as to obtain a compound of formula (I) as defined in claim 1;
or with a compound of formula (XII) X'-L-Lg wherein L is an optionally substituted linear or branched $C_2$-$C_6$ alkyl or $C_3$-$C_7$ cycloalkyl group, Lg is as defined above and X' represents a suitable leaving group;
step 6) reacting the resultant compound of formula (XIII):

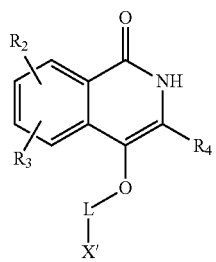

XIII wherein $R_2$, $R_3$, $R_4$, and X' are as defined above, L is an optionally substituted linear or branched $C_2$-$C_6$ alkyl or $C_3$-$C_7$ cycloalkyl group, with a compound of formula (XIV): R—NH—$R_1$ wherein R and $R_1$ are as defined above so as to obtain a compound of formula (I) as defined above; optionally converting a compound of formula (I) into a different compound of formula (I); and/or, if desired, converting a compound of formula (I) into a pharmaceutically acceptable salt thereof or converting a salt into a free compound of formula (I).

6. A pharmaceutical composition comprising a therapeutically effective amount of a compound of formula (I), as defined in claim 1, and at least one pharmaceutically acceptable carrier and/or diluent.

7. A compound of formula (I), as defined in claim 1, for use as a medicament.

8. The pharmaceutical composition according to claim 6 further comprising one or more chemotherapeutic agents.

9. A product comprising a compound of formula (I) as defined in claim 1 or a pharmaceutical composition thereof comprising a therapeutically effective amount of said compound and at least one pharmaceutically acceptable carrier and/or diluent, and one or more chemotherapeutic agents, as a combined preparation for simultaneous, separate or sequential use in anticancer therapy.

* * * * *